（12) United States Patent
Petkovich et al.

US010493084B2

(10) Patent No.: US 10,493,084 B2
(45) Date of Patent: *Dec. 3, 2019

(54) ADJUNCTIVE THERAPY WITH 25-HYDROXYVITAMIN D AND ARTICLES THEREFOR

(71) Applicant: OPKO IRELAND GLOBAL HOLDINGS, LTD., Grand Cayman (KY)

(72) Inventors: P. Martin Petkovich, Kingston (CA); Joel Z. Melnick, Evanston, IL (US); Jay A. White, Newmarket (CA); Samir P. Tabash, Whitby (CA); Charles W. Bishop, Miami Beach, FL (US); Susan Peers, Toronto (CA); Stephen A. Strugnell, Bay Harbor Islands, FL (US)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,549

(22) Filed: Jan. 9, 2019

(65) Prior Publication Data

US 2019/0142847 A1  May 16, 2019

Related U.S. Application Data

(60) Division of application No. 14/866,155, filed on Sep. 25, 2015, now Pat. No. 10,220,047, which is a continuation-in-part of application No. PCT/EP2015/068219, filed on Aug. 6, 2015.

(60) Provisional application No. 62/034,604, filed on Aug. 7, 2014.

(51) Int. Cl.
| | |
|---|---|
| *A61K 31/593* | (2006.01) |
| *A61K 31/592* | (2006.01) |
| *A61K 9/00* | (2006.01) |
| *A61K 47/26* | (2006.01) |
| *A61K 9/48* | (2006.01) |
| *A61K 31/675* | (2006.01) |
| *A61K 31/135* | (2006.01) |
| *A61K 31/663* | (2006.01) |
| *A61K 47/44* | (2017.01) |
| *A61K 31/137* | (2006.01) |
| *A61K 45/06* | (2006.01) |
| *A61K 47/06* | (2006.01) |
| *A61K 47/14* | (2017.01) |
| *A61K 47/38* | (2006.01) |

(52) U.S. Cl.
CPC .......... *A61K 31/593* (2013.01); *A61K 9/0019* (2013.01); *A61K 9/0053* (2013.01); *A61K 9/4825* (2013.01); *A61K 9/4875* (2013.01); *A61K 31/135* (2013.01); *A61K 31/137* (2013.01); *A61K 31/592* (2013.01); *A61K 31/663* (2013.01); *A61K 31/675* (2013.01); *A61K 45/06* (2013.01); *A61K 47/06* (2013.01); *A61K 47/14* (2013.01); *A61K 47/26* (2013.01); *A61K 47/38* (2013.01); *A61K 47/44* (2013.01)

(58) Field of Classification Search
CPC .. A61K 31/593; A61K 31/675; A61K 31/663; A61K 47/44; A61K 9/4825; A61K 31/137; A61K 9/0053; A61K 47/06; A61K 47/14; A61K 47/38; A61K 45/06; A61K 9/0019; A61K 47/26; A61K 31/592; A61K 9/4875; A61K 31/135
See application file for complete search history.

(56) References Cited

U.S. PATENT DOCUMENTS

| | | | |
|---|---|---|---|
| 3,565,924 A | 2/1971 | Luca et al. |
| 3,833,622 A | 9/1974 | Babcock et al. |
| 3,880,894 A | 4/1975 | De et al. |
| 4,004,003 A | 1/1977 | Babcock et al. |
| 4,230,701 A | 10/1980 | Holick et al. |
| 4,335,120 A | 6/1982 | Holick et al. |
| 4,442,093 A | 4/1984 | Maeda et al. |
| 4,448,721 A | 5/1984 | Deluca et al. |
| 4,555,364 A | 11/1985 | Deluca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |

(Continued)

FOREIGN PATENT DOCUMENTS

| | | |
|---|---|---|
| CA | 2241205 A1 | 7/1997 |
| CN | 101668517 A | 3/2010 |

(Continued)

OTHER PUBLICATIONS

Sensipar package insert (Year: 2004).*

(Continued)

*Primary Examiner* — Aradhana Sasan
*Assistant Examiner* — Quanglong N Truong
(74) *Attorney, Agent, or Firm* — Marshall, Gerstein & Borun LLP

(57) ABSTRACT

Methods, compositions, and kits for adjunctive therapy using 25-hydroxyvitamin D are disclosed. The 25-hydroxyvitamin D may be administered with an agent that increases the risk of hypocalcemia, such as cinacalcet or a salt thereof, and/or an anticancer agent. The adjunctive therapy is effective to treat and prevent iatrogenic hypocalcemia and/or secondary hyperparathyroidism, as well as delay cancer progression and the time to a post-treatment skeletal related event.

22 Claims, No Drawings

(56) References Cited

U.S. PATENT DOCUMENTS

| | | |
|---|---|---|
| 4,729,895 A | 3/1988 | Makino et al. |
| 4,755,544 A | 7/1988 | Makino et al. |
| 4,892,821 A | 1/1990 | Omura et al. |
| 4,997,824 A | 3/1991 | Popovtzer et al. |
| 5,026,559 A | 6/1991 | Eichel et al. |
| 5,160,742 A | 11/1992 | Mazer et al. |
| 5,328,903 A | 7/1994 | Ishii et al. |
| 5,342,626 A | 8/1994 | Winston et al. |
| 5,354,743 A | 10/1994 | Thys-Jacobs |
| 5,403,831 A | 4/1995 | Deluca et al. |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,872,113 A | 2/1999 | Nestor et al. |
| 5,888,994 A | 3/1999 | Hennessy et al. |
| 5,919,986 A | 7/1999 | Barbier et al. |
| 5,939,408 A | 8/1999 | Batcho et al. |
| 5,958,451 A | 9/1999 | Chen |
| 5,976,784 A | 11/1999 | Deluca et al. |
| 6,001,884 A | 12/1999 | Nemeth et al. |
| 6,011,068 A | 1/2000 | Nemeth et al. |
| 6,031,003 A | 2/2000 | Nemeth et al. |
| 6,034,075 A | 3/2000 | Thys-Jacobs |
| 6,051,567 A | 4/2000 | Abrahamson et al. |
| 6,096,876 A | 8/2000 | St-Arnaud et al. |
| 6,121,469 A | 9/2000 | Norman et al. |
| 6,133,250 A | 10/2000 | Knutson et al. |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | Van Lengerich |
| 6,190,695 B1 | 2/2001 | Hoshino et al. |
| 6,211,244 B1 | 4/2001 | Van et al. |
| 6,214,376 B1 | 4/2001 | Gennadios |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |
| 6,288,849 B1 | 9/2001 | Teramoto |
| 6,313,146 B1 | 11/2001 | Van et al. |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | Deluca et al. |
| 6,491,950 B1 | 12/2002 | Gutierrez-Rocca et al. |
| 6,503,893 B2 | 1/2003 | Bishop et al. |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,627,622 B2 | 9/2003 | Deluca et al. |
| 6,645,527 B2 | 11/2003 | Oshlack et al. |
| 6,770,295 B1 | 8/2004 | Kreilgaard et al. |
| 6,887,493 B2 | 5/2005 | Shefer et al. |
| 6,893,658 B1 | 5/2005 | Iida et al. |
| 6,903,083 B2 | 6/2005 | Knutson et al. |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,166,585 B2 | 1/2007 | Posner et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,528,122 B2 | 5/2009 | Deluca et al. |
| 7,632,518 B2 | 12/2009 | Tritsch et al. |
| 7,648,826 B1 | 1/2010 | Albertson et al. |
| 7,807,194 B2 | 10/2010 | Modliszewski et al. |
| 7,816,341 B2 | 10/2010 | Sewall et al. |
| 7,829,595 B2 | 11/2010 | Lawrence et al. |
| 7,846,475 B2 | 12/2010 | Shiraishi et al. |
| 7,973,024 B2 | 7/2011 | Posner et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 | 6/2012 | Tabash et al. |
| 8,231,896 B2 | 7/2012 | Tanner et al. |
| 8,268,352 B2 | 9/2012 | Vaya et al. |
| 8,293,270 B2 | 10/2012 | Sukuru |
| 8,329,677 B2 | 12/2012 | Bishop et al. |
| 8,361,488 B2 | 1/2013 | Bishop et al. |
| 8,377,470 B2 | 2/2013 | Tanner et al. |
| 8,426,391 B2 | 4/2013 | Bishop et al. |
| 8,592,401 B2 | 11/2013 | Petkovich et al. |
| 8,759,328 B2 | 6/2014 | Deluca et al. |
| 8,778,373 B2 | 7/2014 | Bishop et al. |
| 8,906,410 B2 | 12/2014 | Bishop et al. |
| 8,962,239 B2 | 2/2015 | Petkovich et al. |
| 8,992,971 B2 | 3/2015 | Yang |
| 9,017,720 B2 | 4/2015 | Andersen et al. |
| 9,125,823 B2 | 9/2015 | Selva et al. |
| 9,402,855 B2 | 8/2016 | Bishop et al. |
| 9,408,858 B2 | 8/2016 | Bishop et al. |
| 9,498,486 B1 | 11/2016 | Bishop et al. |
| 9,500,661 B2 | 11/2016 | Petkovich et al. |
| 9,913,852 B2 | 3/2018 | Bishop et al. |
| 10,220,047 B2 * | 3/2019 | Petkovich ............ A61K 31/135 |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0044968 A1 | 4/2002 | Van Lengerich |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1 | 12/2002 | Mazess et al. |
| 2003/0059471 A1 | 3/2003 | Compton et al. |
| 2003/0129194 A1 | 7/2003 | Mazess et al. |
| 2003/0138482 A1 | 7/2003 | Fonkwe et al. |
| 2003/0152629 A1 | 8/2003 | Shefer et al. |
| 2003/0157560 A1 | 8/2003 | Cantor |
| 2003/0195171 A1 | 10/2003 | Daifotis et al. |
| 2004/0043971 A1 | 3/2004 | Mazess et al. |
| 2004/0101554 A1 | 5/2004 | Kirschner et al. |
| 2004/0132695 A1 | 7/2004 | Posner et al. |
| 2004/0224930 A1 | 11/2004 | Posner et al. |
| 2005/0014211 A1 | 1/2005 | Armbruster et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |
| 2005/0106233 A1 | 5/2005 | Andersen et al. |
| 2005/0124591 A1 | 6/2005 | Tian et al. |
| 2005/0143358 A1 | 6/2005 | Deluca et al. |
| 2005/0147669 A1 | 7/2005 | Lawrence et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0208055 A1 | 9/2005 | Chuang et al. |

(56) References Cited

U.S. PATENT DOCUMENTS

| | | |
|---|---|---|
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0027120 A1 | 2/2007 | Whitehouse et al. |
| 2007/0032461 A1 | 2/2007 | Adorini et al. |
| 2007/0122477 A1 | 5/2007 | Bishop et al. |
| 2007/0155664 A1 | 7/2007 | Ranklove et al. |
| 2007/0190146 A1 | 8/2007 | Roger et al. |
| 2007/0207488 A1 | 9/2007 | Trump et al. |
| 2008/0109983 A1 | 5/2008 | Davis |
| 2008/0134937 A1 | 6/2008 | Yang |
| 2008/0199534 A1 | 8/2008 | Goldberg et al. |
| 2008/0317764 A1 | 12/2008 | Huber et al. |
| 2009/0004284 A1 | 1/2009 | Cheng et al. |
| 2009/0069389 A1 | 3/2009 | Choi et al. |
| 2009/0137536 A1 | 5/2009 | Mazess et al. |
| 2009/0155355 A1 | 6/2009 | Heuer et al. |
| 2009/0176748 A1 | 7/2009 | Tabash et al. |
| 2009/0209501 A1 | 8/2009 | Bishop et al. |
| 2009/0262685 A1 | 10/2009 | Schuringa et al. |
| 2009/0311316 A1 | 12/2009 | Bishop et al. |
| 2010/0120728 A1 | 5/2010 | Petkovich et al. |
| 2010/0144684 A1 | 6/2010 | Bishop |
| 2010/0227889 A1 | 9/2010 | Gerspacher et al. |
| 2010/0291191 A1 | 11/2010 | Shoichet et al. |
| 2010/0291197 A1 | 11/2010 | Schwab |
| 2011/0039810 A1 | 2/2011 | Buck et al. |
| 2011/0039811 A1 | 2/2011 | Buck et al. |
| 2011/0105444 A1 | 5/2011 | Deluca et al. |
| 2011/0118218 A1 | 5/2011 | Buck et al. |
| 2011/0130370 A1 | 6/2011 | Briault et al. |
| 2011/0171298 A1 | 7/2011 | Cao |
| 2011/0182986 A1 | 7/2011 | Speirs et al. |
| 2011/0256230 A1 | 10/2011 | Haeusler et al. |
| 2011/0300210 A1 | 12/2011 | Swanson et al. |
| 2011/0318321 A1 | 12/2011 | Selva et al. |
| 2011/0319503 A1 | 12/2011 | Muller et al. |
| 2012/0015916 A1 | 1/2012 | Tabash et al. |
| 2012/0135103 A1 | 5/2012 | Walsh et al. |
| 2013/0085121 A1 | 4/2013 | Wang et al. |
| 2013/0137663 A1 | 5/2013 | Messner et al. |
| 2013/0178451 A1 | 7/2013 | Bishop et al. |
| 2013/0189522 A1 | 7/2013 | Fujii et al. |
| 2013/0216618 A1 | 8/2013 | Muller et al. |
| 2013/0302309 A1 | 11/2013 | Yang |
| 2014/0088202 A1 | 3/2014 | Cade et al. |
| 2014/0248400 A1 | 9/2014 | Phonchareon et al. |
| 2014/0274977 A1 | 9/2014 | Bishop et al. |
| 2014/0349979 A1 | 11/2014 | White et al. |
| 2014/0357603 A1 | 12/2014 | Bishop et al. |
| 2015/0079165 A1 | 3/2015 | Bishop et al. |
| 2015/0119472 A1 | 4/2015 | Shuai et al. |
| 2015/0119473 A1 | 4/2015 | Shuai et al. |
| 2017/0119677 A1 | 5/2017 | Bishop et al. |
| 2018/0021354 A1* | 1/2018 | Petkovich ............ A61K 31/135 424/463 |

FOREIGN PATENT DOCUMENTS

| | | |
|---|---|---|
| EP | 0227836 A1 | 7/1987 |
| EP | 0413828 A1 | 2/1991 |
| EP | 0508756 A1 | 10/1992 |
| EP | 0387808 B1 | 5/1993 |
| EP | 0629405 A1 | 12/1994 |
| EP | 1208843 A1 | 5/2002 |
| EP | 1165061 B1 | 10/2005 |
| EP | 1980255 A1 | 10/2008 |
| EP | 2037936 A2 | 3/2009 |
| EP | 2148661 B1 | 12/2012 |
| JP | 55-139320 | 10/1980 |
| JP | 57-188520 | 11/1982 |
| JP | 58-032823 | 2/1983 |
| JP | 58-206524 A | 12/1983 |
| JP | 64-031722 | 2/1989 |
| JP | 02-229115 A | 9/1990 |
| JP | 04-198129 A | 7/1992 |
| JP | 04-208225 A | 7/1992 |
| JP | 04-288016 A | 10/1992 |
| JP | 07-242550 A | 9/1995 |
| JP | 08-092098 A | 4/1996 |
| JP | 10-158171 A | 6/1998 |
| JP | 11-158074 A | 6/1999 |
| JP | 2001-512418 A | 8/2001 |
| JP | 2002-302447 A | 10/2002 |
| JP | 2004-175750 A | 6/2004 |
| JP | 2005-513419 A | 5/2005 |
| JP | 2005-531532 A | 10/2005 |
| JP | 2006-523221 A | 10/2006 |
| JP | 2007-525472 A | 9/2007 |
| JP | 2010-506520 A | 2/2010 |
| JP | 2010-525079 A | 7/2010 |
| JP | 2011-512343 A | 4/2011 |
| JP | 2012-515738 A | 7/2012 |
| KR | 10-2012-0005228 A | 1/2012 |
| WO | 91/12807 A1 | 9/1991 |
| WO | 91/16899 A1 | 11/1991 |
| WO | 92/09271 A1 | 6/1992 |
| WO | 94/00128 A1 | 1/1994 |
| WO | 96/00074 A1 | 1/1996 |
| WO | 96/01621 A1 | 1/1996 |
| WO | 96/31215 A1 | 10/1996 |
| WO | 97/11053 A1 | 3/1997 |
| WO | 98/18610 A1 | 5/1998 |
| WO | 98/29105 A2 | 7/1998 |
| WO | 99/11272 A1 | 3/1999 |
| WO | 99/49027 A1 | 9/1999 |
| WO | 00/21504 A1 | 4/2000 |
| WO | 00/35419 A2 | 6/2000 |
| WO | 00/60109 A1 | 10/2000 |
| WO | 00/61123 A2 | 10/2000 |
| WO | 01/37808 A1 | 5/2001 |
| WO | 01/72286 A1 | 10/2001 |
| WO | 03/09572 A1 | 1/2003 |
| WO | 03/39521 A1 | 5/2003 |
| WO | 03/39572 A1 | 5/2003 |
| WO | 03/45381 | 6/2003 |
| WO | 03/47595 A1 | 6/2003 |
| WO | 03/88976 A1 | 10/2003 |
| WO | WO-03/086415 A1 | 10/2003 |
| WO | 03/93459 A1 | 11/2003 |
| WO | 2003/106411 A1 | 12/2003 |
| WO | 2004/028515 A1 | 4/2004 |
| WO | 2004/054968 A2 | 7/2004 |
| WO | 2004/058235 A2 | 7/2004 |
| WO | 2004/080467 A2 | 9/2004 |
| WO | 2004/098617 A2 | 11/2004 |
| WO | 2004/101554 A1 | 11/2004 |
| WO | 2004/110381 A2 | 12/2004 |
| WO | 2004/110391 A2 | 12/2004 |
| WO | 2005/000268 A2 | 1/2005 |
| WO | 2005/003358 A1 | 1/2005 |
| WO | 2005/011652 A2 | 2/2005 |
| WO | 2005/123120 A1 | 12/2005 |
| WO | 2006/052452 A1 | 5/2006 |
| WO | 2006/059180 A2 | 6/2006 |
| WO | 2006/113505 A2 | 10/2006 |
| WO | 2007/039193 A1 | 4/2007 |
| WO | 2007/039569 A2 | 4/2007 |
| WO | 2007/047327 A2 | 4/2007 |
| WO | 2007/050724 A2 | 5/2007 |
| WO | 2007/050975 A2 | 5/2007 |
| WO | 2007/053608 A2 | 5/2007 |
| WO | 2007/068287 A1 | 6/2007 |
| WO | 2007/092221 A2 | 8/2007 |
| WO | 2007/092755 A2 | 8/2007 |

(56) References Cited

FOREIGN PATENT DOCUMENTS

| WO | 2007/146004 A1 | 12/2007 |
|---|---|---|
| WO | 2008/008608 A2 | 1/2008 |
| WO | 2008/043449 A1 | 4/2008 |
| WO | 2008/097646 A1 | 8/2008 |
| WO | 2008/116113 A1 | 9/2008 |
| WO | 2008/116133 A1 | 9/2008 |
| WO | 2008/134512 A1 | 11/2008 |
| WO | 2008/134523 A1 | 11/2008 |
| WO | WO-2008/134518 A2 | 11/2008 |
| WO | 2009/047644 A2 | 4/2009 |
| WO | 2009/101132 A1 | 8/2009 |
| WO | 2009/101137 A1 | 8/2009 |
| WO | WO-2009/101135 A1 | 8/2009 |
| WO | 2009/124210 A1 | 10/2009 |
| WO | 2010/011906 A1 | 1/2010 |
| WO | 2010/034342 A1 | 4/2010 |
| WO | 2011/031621 A2 | 3/2011 |
| WO | 2011/063952 A1 | 6/2011 |
| WO | 2011/095388 A1 | 8/2011 |
| WO | 2011/123476 A1 | 10/2011 |
| WO | 2012/018329 A1 | 2/2012 |
| WO | 2012/076429 A1 | 6/2012 |
| WO | 2012/091569 A1 | 7/2012 |
| WO | 2012/117236 A1 | 9/2012 |
| WO | 2012/145491 A2 | 10/2012 |
| WO | 2014/029953 A1 | 2/2014 |
| WO | 2014/143941 A1 | 9/2014 |
| WO | 2014/202754 A1 | 12/2014 |
| WO | WO-2014/193255 A1 | 12/2014 |
| WO | 2016/020508 A2 | 2/2016 |

OTHER PUBLICATIONS

Parise et al., CYP24, the enzyme that catabolizes the antiproliferative agent vitamin D, is increased in lung cancer, Int. J. Cancer, 119(8):1819-28 (2006).
Parfitt et al., "Calcitriol But No Other Metabolite of Vitamin D is Essential for Normal Bone Growth and Development in the Rat," J. Clin. Invest., 73:576-586 (1984).
Pak et al., "Treatment of Vitamin D-Resistant Rickets With 25-Hydroxycholecalciferol," Arch Intern Med, 129:894-899 (1972).
Package insert for Zemplar (paricalcitol) Capsules, Abbott (2011).
Package insert for Hectorol (doxercalciferol capsules), Genzyme (2011).
Olmos et al., Effects of 25-hydroxyvitamin D3 therapy on bone turnover markers and PTH levels in postmenopausal osteoporotic women treated with alendronate, J. Clin. Endocrinol. Metab., 97(12):4491-7 (2012).
Oksa et al., "Effects of long-term cholecalciferol supplementation on mineral metabolism and calciotropic hormones in chronic kidney disease," Kidney Blood Press Res., 31: 322-329 (2008).
Office Action (with English translation), Japanese patent application No. 2014-031369, dated Mar. 9, 2015.
Notice of allowance dated Jul. 10, 2012, in EPO application 08746908.6.
Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
National Kidney Foundation Guidelines, NKF, Am. J. Kidney Dis., 42(4,Suppl 3):S1-S202 (2003).
Nakanishi et al., "The Roles of Vitamin D in Secondary Hyperparathyroidism," [journal in Japanese] 52:1107-1112 (2004).
Naik et al., "Effects of Vitamin D Metabolites and Analogues on Renal Function," Nephron, 28:17-25 (1981).
Muindi Caplet et al., "Phamacokinetics of Liquid Calcitriol Formulation in Advanced Solid Tumor Patients: Comparison with Formulation," Cancer Chemother. Pharmacol., 56:492-496 (2005).
Motellon et al., Parathyroid hormone-related protein, parathyroid hormone, and vitamin D in hypercalcemia of malignancy, Clin. Chim. Acta, 290(2):189-97 (2000).
Morris, "Vitamin D: A Hormone for All Seasons—How Much is Enough?" Clin. Biochem. Rev., 26:21-32 (2005).
Morris, (2002). "Cats Discriminate Between Cholecalciferol and Ergocalciferol," J. Anim. Physiol. a. Anim. Nutr., 86:229-238.
Moe et al., "Safety and Efficacy of Pulse and Daily Calcitriol in Patients on CAPD: A Randomized Trial," Nephrol. Dial. Transplant., 13:1234-1241 (1998).
Moe et al., "A randomized trial of cholecalciferol versus doxercalciferol for lowering parathyroid hormone in chronic Kidney disease," Clin.J.Am.Soc.Nephrol. 5: 299-306 (2010).
Modern Pharmaceutics 4th ed., Marcel Dekker, Inc., New York, NY, p. 16-21 (2002).
Mimori et al., Clinical significance of the overexpression of the candidate oncogene CYP24 in esophageal cancer, Ann. Oncol., 15(2):236-41 (2004).
Messa et al., "Direct In Vivo Assessment of Parathyroid Hormone-Calcium Relationship Curve in Renal Patients," Kidney Int., 46:1713-1720 (1994).
Menon et al., "Vitamin D insufficiency and hyperparathyroidism in children with chronic kidney disease," Pedaitr Nephrol, 23:1831-1836 (2008).
Memmos et al., "Response of uremic osteoid to vitamin D," Kidney Int, 21(Suppl. 11): S50-S54 (1982).
Melanie S Joy PharMD FCCP et al: "Outcomes of Secondary Hyperparathyroidism in Chronic Kidney Disease and the Direct Costs of Treatment", Journal of Managed Care Pharmacy, Academy of , Managed Care Pharmacy, Alexandria, VA, vol. 13, No. 5, Jan. 1, 2007 (Jan. 1, 2007), pp. 397-411.
Mazur, "Effects of 25-OHD3 on Renal Function in Pediatric Patients with Chronic Renal Failure," Mineral Electrolyte Metab. 10:351-358 (1984).
Mazouz et al., "Risk factors of renal failure progression two years prior to dialysisis" Clinical Nephrology 51(6):355-366 (1999).
Matsushita et al., "Clinical effects of 25-hydroxycholecalciferol in patients with chronic renal failure," J Nutr Sci Vitaminol, 23:257-261 (1977).
Martin et al., "19-Nor-1-alpha-25-Dihydroxyvitamin D2 (Paricalcitol) Safely and Effectively Reduces the Levels of Intact Parathyroid Hormone in Patients on Hemodialysis," J. Am. Soc. Nephrol., 9:1427-1432 (1998).
Manni et al., "Oral Calcitriol: Comparison Between the Same Weekly Dose Administered as a Single vs. Two Divided Pulsed Doses in Secondary Hyperparathyroidism of Chronic Renal Failure," Ital. J Mineral Electrolyte Metab., 11:61-64 (1997).
Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).
Luo et al., 24-Hydroxylase in cancer: impact on vitamin D-based anticancer therapeutics, J. Steroid Biochem. Mol. Biol., 136:252-7 (2013).
Lund et al., "Serum 1,25-Dihydroxycholecalciferol in Anephric. Haemodialyzed and Kidney-transplanted Patients," Nephron, 25:30-33 (1980).
Lomonte et al., "Are Low Plasma Levels of 25-(OH) Vitamin D a Major Risk Factor for Hyperparathyroidism Independent of Calcitriol in Renal Transplant Patients?" J. Nephrol., 18:96-101 (2005).
Lo et al., Vitamin D absorption in healthy subjects and in patients with intestinal malabsorption syndromes, Am. J. Clin. Nutr., 42(4):644-9 (1985).
Lips (A Global Study of Vitamin D Status and Parathyroid Function in Postmenopausal Women with Osteoporosis: Baseline Data from the Muliple outcomes of Raloxifen Evaluation Clinical Trial, The Journal of Clinical Endocrinology & Metabolism, 2000, vol. 86, No. 3, pp. 1212-1221).
Letteri et al., "Effects of 25-Hydroxycholecalciferol on Calcium Metabolism in Chronic Renal Failure" Adv. Exp. Med. Biol. 81:591-601 (1977).
Lehmann et al., "Coating of Tablets and Small Particles with Acrylic Resins by Fluid Bed Technology," Int. J. Pharm. Tech. & Prod. Mfr., 2:31-43 (1981).

(56) References Cited

OTHER PUBLICATIONS

Lee et al., Comparison between calcitriol and calcitriol plus low-dose cinacalcet for the treatment of moderate to severe secondary hyperparathyroidism in chronic dialysis patients, Nutrients, 5(4):1336-48 (2013).
Lau et al., "Vitamin D Therapy of Osteoporosis: Plain Vitamin D Therapy Versus Active Vitamin D Analog (D-Hormone) Therapy," Calcif. Tissue Int., 65:295-306 (1999).
Larrosa M. et al., "Long-Term Treatment of Hypovitaminosis D. Calcidol or Cholecalciferol" Annals of the Rheumatic Diseases, vol. 64, No. Suppl. 3, Jul. 2005, p. 366.
Langman et al., "25-Hydroxyvitamin D3 (Calcifediol) Therapy of Juvenile Renal Osteodystrophy: Beneficial Effect on Linear Growth Velocity," J. Pediatrics, 100:815-820 (1982).
Lambrey, "Possible Link Between Changes in Plasma 24,25-Dihydroxyvitamin D and Healing of Bone Resorption in Dialysis Osteodrstrophy" Metab. Bone Dis. & Rel. Res. 4:25-30 (1982).
Lambrey et al., "24, 25 Dihydroxycalciferol: Assay in Non-Anephric Patients on Chronic Haemodialysis and Assessment of it's Possible Pathophysiological Role in Renal Osteodystrophy" Proc Eur Dial Transplant Assoc. 17:548-556 (1980).
Lambert et al., "Evidence for Extranrenal Production of 1-alpha,25-Dihydroxyvitamin D in Man," J. Clin. Invest., 69:722-725 (1982).
Lafage et al., "Ketodiet, physiological calcium intake and native vitamin D improve renal osteodystrophy" Kidney International 42:1217-1225 (1992).
LaClair et al., "Prevalence of Calcidiol Deficiency in CKD: A Cross-Sectional Study Across Latitudes in the United States," Am. J. Kidney Dis., 45:1026-1033 (2005).
Kuro-O, Klotho in chronic kidney disease—what's new?, Nephrol. Dial. Transplant., 4 pp. (2009).
Krishnan et al., The role of vitamin D in cancer prevention and treatment, Rheum. Dis. Clin. North Am., 38(1):161-78 (2012).
Kovesdy et al., Association of activated vitamin D treatment and mortality in chronic kidney disease, Arch. Intern. Med., 168(4):397-403 (Feb. 2008).
Koshikawa et al., "Clinical effect of intravenous calcitrol administration on secondary hyperparathyroidism. A double-blind study among 4 doses", Nephron, 90:413-423 (2002).
Kooienga et al., "The effect of combined calcium and vitamin D3 supplementation on serum intact parathyroid hormone in moderate CKD," Am.J.Kidney Dis,. 53: 408-416 (2009).
Kobayashi et al., "Variation of 25-Hydroxyvitamin D3 and 25-Hydroxyvitamin D2 Levels in Human Plasma Obtained from 758 Japanese Healthy Subjects," J. Nutr. Sci. Vitaminol (Tokyo), 29(3):271-281 (1983). Abstract Only.
Kobayashi et al., "2.beta.-(3-Hydroxyproxy)-.alpha.,25-Dihydroxyvitamin D3 (ED-71), Preventive and Therapeutic Effects on Bone Mineral Loss in Ovariectomized Rats," Bioorganic & Medicinal Chemistry Letters, 3(9):1815-1819 (1993).
Kleinman et al., "Effects of Calcifediol on Calcified Tissue in Uremia," Arch Intern Med, 138: 864-865 (1978).
Kinoshita et al., "1,25-Dihydroxyvitamin D Suppresses Circulating Levels of Parathyroid Hormone in a Patient with Primary Hyperparathyroidism and Coexistent Sarcoidosis," J. Clin. Endo. & Metabol., 90(12):6727-6731 (2005).
Kim, Advanced Pharmaceutics: Physicochemical Principles, pp. 362-392, Boca Raton, Fla: CRC Press (2004).
Kidney Disease Outcomes Quality Initiative (K/DOQI) Clinical Practice Guidelines for Bone Metabolism and Disease in Chronic Kidney Disease, Am. J. Kidney Dis .. 42:S1-S202 (2003).
Kidney Disease Improving Global Outcomes (KDIGO) Clinical Practice Guidelines for Diagnosis, Evaluation, Prevention, and Treatment of Chronic Kidney Disease-Mineral and Bone Disorder (CKD-MBD), Kidney International Supplement, 113:S1-130 (2009).
Kidney Disease Improving Global Outcomes (KDIGO) 2017 Clinical Practice Guideline Update for the Diagnosis, Evaluation, Prevention, and Treatment of Chronic Kidney Disease-Mineral and Bone Disorder (CKD-MBD). Kidney Int Suppl. 2017;7(11:1-59.

Khachane et al., "Novel Suatained Release Drug Delivery System: Review," IJPRD, 3(12):1-14 (2012).
KDOQI Clinical practice guidelines 2004. National Kidney Foundation.
Kazama et al., Role of circulating fibroblast growth factor 23 in the development of secondary hyperparathyroidism, Ther. Apher. Dial., 9:328-30 (2005).
Kaufmann et al., Clinical utility of simultaneous quantitation of 25-hydroxyvitamin D and 24,25-dihydroxyvitamin D by LC-MS/MS involving derivatization with DMEQ-TAD, J. Clin. Endocrinol. Metab., 99(7):2567-74 (Jul. 2014).
Kanis et al., "Rate of Reversal of Hypercalcaemia and Hypercalciuria Induced by Vitamin D and Its 1-alpha-Hydroxylated Derivatives," BMJ, 1:78-81 (1977).
Kalantar-Zadeh et al., "Clinical Outcomes with Active versus Nutritional Vitamin D Compounds in Chronic Kidney Disease" Clin J Am Soc Nephrol. 4(9):1529-1539 (2009).
Kajihara et al., "Novel Method to Control Release of Lipophilic Drugs with High Potency from Silicone," Chem. Pharm. Bull., 51:11-14 (2003).
Joy et al., Outcomes of secondary hyperparathyroidism in chronic kidney disease and the direct costs of treatment, J. Managed Care Pharm., 13:397-411 (2007).
Jones., "Expanding the Role for Vitamin D in Chronic Kidney Disease: Importance of Blood 25-OH-D Levels and Extra-Renal 1?-Hydroxyase in the Classical and Nonclassical Actions of 1?, 25-Dihydroxyvitamin D3," Seminars in Dialysis, 20(4)316-324 (2007).
Jones, "Why dialysis patients need combination therapy with both cholecalciferol and a calcitriol analogs," Seminars in Di alysis, pp. 1-5 (2010).
Jones, "Pharmacokinetics of vitamin D toxicity," Am. J. Clin. Nutr. 88(suppl): 582S-6S (2008).
Jones et al., Cytochrome P450-mediated metabolism of vitamin D, J. Lipid Res., 55(1):13-31 (2014).
Jean et al., "Monthly cholecalciferol administration in heamodialysis patients: a simple and efficient strategy for vitamin D supplementation" Nephrol. Dial. Transplant 24(12):3799-3805 (2009).
Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" Nephron. Clin. Pract. 110:c58-c65 (2008).
Jean et al., "Daily oral 25-hydroxycholecalciferol supplementation for vitamin D deficiency in haemodialysis patients: effects on mineral metabolism and bone markers" Nephrol. Dial. Transplant 23(11):3670-3676 (2008).
Jara et al., "Effect of Calcitriol Treatment and Withdrawal on Hyperparathyroidism in Haemodialysis Patients with Hypocalcaemia," Nephrol. Dial. Transplant., 16:1009-1016 (2001).
Japanese patent application No. 2016-502712, Office Action (English translation), dated Dec. 18, 2017.
Japanese Office Action for Application No. 2008-553520, dated Jul. 24, 2011.
Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," Kidney Int., 55:1019-1027 (1999).
International Search Report for corresponding international application No. PCT/US2007/071791 (dated Feb. 5, 2008).
International Search Report for Application No. PCT/US2007/061521, dated Jul. 17, 2007.
International Search Report for Application No. PCT/IB2008/003480, dated Mar. 31, 2009.
International Search Report and Written Opinion, International Application No. PCT/EP2016/052866, dated Jun. 9, 2016.
International Search Report and Written Opinion, International Application No. PCT/EP2015/068219, dated Jan. 29, 2016.
International Search Report and Written Opinion for PCT/US2008/061579 dated Aug. 21, 2008 (5 pages).
International Search Report and Written Opinion for International Application No. PCT/US08/61594 (dated Jul. 28, 2008).

(56) References Cited

OTHER PUBLICATIONS

International Search Report and Written Opinion for corresponding international application No. PCT/US11/30404, dated May 25, 2011.
International Search Report and Written Opinion for corresponding International Application No. PCT/US09/39355, dated Jun. 17, 2009.
International Search Report and Written Opinion for Application No. PCT/US2007/061521, dated Jul. 17, 2007.
International Preliminary Report on Patentability of PCT/US2008/061579 dated Oct. 27, 2009.
International Preliminary Report on Patentability for corresponding international application No. PCT/US2011/030404, dated Oct. 2, 2012.
International Preliminary Report on Patentability for corresponding International Application No. PCT/US09/39355, dated Oct. 5, 2010.
International Application No. PCT/EP2017/057282, International Search Report and Written Opinion, dated Sep. 8, 2017.
International Application No. PCT/EP2017/057282, International Preliminary Report on Patentability, dated Oct. 2, 2018.
Inoue et al., Role of the vitamin D receptor in FGF23 action on phosphate metabolism, Biochem. J., 399:325-31 (2005).
Ibrahim et al., Serum fibroblast growth factor-23 levels in chronic haemodialysis patients, Int. Urol. Nephrol., 41:163-9 (2009).
Hussar, "New Drugs of 1999," J. Am. Pharmacist. Assoc. 40(2):181-229 (2000).
Hunt, et al., "A Comparison of the Toxicity of Ergocalciferol and Cholecalciferol in Rhesus Monkeys (Macaca mulatta)," J. Nutrition, 102:975-986 (1972).
Houghton et al., "The Case Against Ergocalciferol (Vitamin D2) as a Vitamin Supplement," Am. J. Clin. Nutr., 84:694-697 (2006).
Hottelart et al., "Osteodystrophie renale (2): son traitement chez l'insuffisant renal avant la dialyse" Nephrologie 21(6):275-282 (2000) [reference in French].
Fournier et al., "The Approach to the Treatment of Secondary Hyperparathyroidism in Early Renal Failure" Am. J. Nephrol 8:170-172 (1988).
Fournier et al., "Renal Osteodystrophy: Pathophysiology and Treatment" Hormone Res. 20:44-58 (1984).
Fournier et al., "Renal Osteodystrophy in Dialysis Patients: Diagnosis and Treatment," Artificial Organs, 22:530-557 (1998).
Fournier et al., "Preventing renal bone disease in moderate renal failure with CaCO3 and 25 (OH) vitamin D3" Kidney International, 33(24):S178-S179 (1988).
Fournier et al., "Present-Day Concepts in the Treatment of Chronic Renal Failure" Contrib Nephrol. 71:64-80 (1989).
Fournier et al., "Low doses of calcitriol or calcium carbonate for the prevention of hyperparathyroidism in predialysis patients?" Nephrol Dial Transplant 11(7):1493-1495 (1996).
Fournier et al., "Importance of Vitamin D Repletion in Uraemia," Nephrol Dial Transplant, 14(4):819-823 (1999).
Fournier et al., "Impact of calcium and vitamin D therapy on arterial and cardiac disease in young adults with childhood-onset and stage renal disease," Nephrol Dial Transplant, 22:956-957 (2006).
Fournier et al., "Current Status of the Management of Renal Osteodystrophy" Proceedings of the European Dialysis and Transplant Association 15:547-568 (1978).
Fournier et al., "Comparison of 1 alpha-hydroxycholecalciferol and 25-hydroxycholecalciferol in the treatment of renal osteodystrophy: Greater effect of 25-hydroxycholecalciferol on bone mineralization" Kidney International 15:196-204 (1979).
Fournier et al., "Advances in Nephrology from the Necker Hospital" Adv. Nephrol Necker Hosp. 21:237-306 (1992).
Fournier et al., "1-alpha-Hydroxycholecalciferol and 25-Hydroxycholecalciferol in Renal Bone Disease," Calcified Tissues 1975: Proceedings of the 11th European Symposium on Calcified Tissues, 226-235 (1975).
Fournier et al., "1 alpha-hydroxycholecalciferol and 25-hydroxycholecalciferol in Renal Bone Disease" Calcif Tissue Res. 21:226-235 (1976).

Fournier et al., "1 alpha hydroxycholecalciferol and 25 hydroxycholecalciferol in renal bone disease." Proc. Eur. Dial. Transplant. Assoc. 12: 227-236 (1976).
Fliser et al., Fibroblast gowth factor 23 (FGF23) predicts progression of chronic kidney disease: the mild to moderate kidney disease (MMKD) study, J. Am. Soc. Nephrol., 18:2601-8 (2007).
Fernandez et al., "Guidelines for Dosing of Intravenous Calcitriol in Dialysis Patients with Hyperparathyroidism," Nephrol. Dial. Transplant., 11:96-101 (1996).
European Patent Office, Intention to Grant Notification, from corresponding European patent application No. EP 07840277.3 (dated Jan. 9, 2014).
Epps et al., "Vitamin D Metabolism: Implications for Treatment in Oncology," Oncology News, 4:42-44 (2009).
Ennis et al., Current recommended 25-hydroxyvitamin D targets for chronic kidney disease management may be too low, J. Nephrol., 29(1):63-70 (Feb. 2016).
El Abdaimi et al., Reversal of hypercalcemia with the vitamin D analogue EB1089 in a human model of squamous cancer, Cancer Res., 59(14):3325-8 (1999).
Eastwood et al., "The Effect of 25-Hydroxy Vitamin D3 in the Osteomalacia of Chronic Renal Failure," Clin. Sci. Molec. Med., 52:499-508 (1977).
Eastwood et al., "The contrasting effects on bone histology of vitamin D and of calcium carbonate in the osteomalacia of chronic renal failure," Clin Sci Molec Med, 47:23-42 (1974).
Eastwood et al., "Biochemical and histological effects of 1,25 dihydroxycholecalciferol (1,25-DHCC) in the osteomalacia of chronic renal failure," J Urol Nephrol (Paris,) 80(12): 984-985 (1974).
E.W. Martin, "Drug Interactions," in Hazards of Medication, J.B. Lippincott Co. (1978).
Dusso et al., "Extrarenal Production of Calcitrol in Normal and Uremic Humans*," Journal of Clinical Endocrinology and Metabolism, 72(1):157-164 (1991).
Dusso et al., "Extra-renal production of calcitriol in chronic renal failure," Kidney Int., 34:368-375 (1988).
Dusso et al, "Metabolic Clearance Rate and Production Rate of Calcitriol in Uremia," Kidney Int., 35 860-864 (1989).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath DV, Grigoleit HG, Coburn JW, DeLuca HF, Mawer Eb, and Suda T), pp. 791-794. Willem de Gruyter, New York (1979).
Dogan et al., "Effect of depot oral cholecalciferol treatment on secondary hyperparathyroidism in stage 3 and stage 4 chronic kidney diseases patients," Ren Fail., 30: 407-410 (2008).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Disease and Vitamin D, University of California Riverside, retrieved from Internet, <URL: <http://vitamind.ucr.edu/disease.html>> (last update: May 19, 1999).
Dietary Supplement Fact Sheet: Vitamin D, National Institutes of Health, Office of Dietary Supplements (last update: Aug. 5, 2005), retrieved from <URL: http:ods.od.nih.gov/factsheets/vitamind.asp> on Aug. 31, 2007.
Dietary Reference Intakes for Calcium, Phosphorus, Magnesium, Vitamin D, and Fluoride, Standing Committee on the Scientific Evaluation of Dietary Reference Intakes, Food and Nutrition Board, Institute of Medicine, National Academy Press, Washington DC, pp. 250-287 (1997).
DeVille et al., "Effect of Ergocalciferol Supplementation on Serum Parathyroid Hormone and Serum 25-Hydroxyvitamin D in Chronic Kidney Disease," Nephrology, 11:555-559 (2006).
Deroisy et al., "Comparison of the Short-Term Effects of Three Oral Calcium-Vitamin D Formulations and Placebo on Calcium Metabolism," Curr. Ther. Res., 59:370-378 (1998).
DeLuca, "Treatment of renal osteodystrophy with 25-hydroxycholecalciferol," Arch Intern Med, 126(5):896-899 (1970).
DB-Pharma, "Dedrogyl 15 Mg/10ML Calcifediol Oral Drops, Solution," Marketing Authorization No. 317 863.2 (2000).

(56) References Cited

OTHER PUBLICATIONS

Davies, M. et al. "The Absorption and Metabolism of Vitamin D3 from Parenteral Injection Sites", Proceedings of the Workshop on Vitamin D, 4th, Vitam. D: Basic Res. Its Clin. Appl. (1979), abstract.
Daisley-Kydd et al., "Calcitriol in the Management of Secondary Hyperparathyroidism of Renal Failure," Pharmacotherapy., 16:619-630 (1996).
Coyne et al., "Paricalcitol Capsule for the Treatment of Secondary Hyperparathyroidism in Stages 3 and 4 CKD," American Journal of Kidney Diseases, 47(2):263-276 (2006).
Cooke et al., "Vitamin D-Binding Protein (Gc-Globulin): Update 1995," Endocrine Rev., 4:125-128 (1995).
Colodro et al., "Effect of 25-Hydroxy-Vitamin D3 on Intestinal Absorption of Calcium in Normal Man and Patients With Renal Failure," Metabolism, 27(6):745-753 (1978).
Collet et al. "Modified-Release Peroral Dosage Forms," Aulton (ed.), Pharmaceutics: The Science of Dosage Forms, Churchill Livingston, London, pp. 289-305 (2002).
Cohen-Solal et al., "Non-Aluminic Adynamic Bone Disease in Non-Dialyzed Uremic Patients: A New Type of Osteopathy Due to Overtreatment?" Bone, 13:1-5 (1992).
Coen et al., "25-hydroxycholecalciferol in the treatment of renal osteodystrophy in haemodialysed patients," Int J Artificial Organs, 2(6): 278-281 (1979).
Coen et al., "1,25(OH)2D3 and 25-OHD3 in the Treatment of Renal Osteodystrophy: Comparison of Combined Versus 1,25(OH)2D3 Administration Alone," Miner. Electrolyte Metab., 9:19-27 (1983).
Coburn, "An Update on Vitamin D as Related to Nephrology Practice: 2003," Kidney International, vol. 64, Supplement 87, pp. S125-S130 (2003).
Coburn et al., "Use of active Vitamin D sterols in patients with chronic kidney disease, stages 3 and 4," Kidney Int., 63:S49-S53 (2003).
Coburn et al., "Doxercalciferol Safely Suppresses PTH Levels in Patients with Secondary Hyperparathyroidism Associated with Chronic Kidney Disease Stages 3 and 4," Am. J. Kidney Dis., 43(5):877-890 (2004).
Claris-Appiani et al., "Phosphate-Induced PTH Stimulation and Calcitriol Treatment in Children with Early Chronic Renal Insufficiency," J. Bone Miner. Met., 12:S91-S97 (1994).
Chonchol et al., 25-Hydroxyvitamin D, insulin resistance, and kidney function in the Third National Health and Nutrition Examination Survey, Kidney Int., 71(2):134-9 (2007).
Chen et al., Safety of Denosumab Versus Zoledronic Acid in Patients with Bone Metastases: A Meta-Analysis of Randomized Controlled Trials, Oncol. Res. Treat, 39(7-9):453-9 (2016).
Chapuy et al., Biochemical effects of calcium and vitamin D supplementation in elderly, institutionalized, vitamin D-deficient patients, Rev. Rhum. [Engl. Ed. 63 (2), 135-140), Feb. 1996.
Chandra et al., "Cholecalciferol (vitamin D3) therapy and vitamin D insufficiency in patients with chronic kidney disease: a randomized controlled pilot study," Endocr.Pract., 14: 10-17 (2008).
Centorrino et al., "Multiple versus single antipsychotic agents for hospitalized psychiatric patients: case-control study of risks versus benefits," Am J. Psychiatry, 161(4): 700-06 (2004).
Cavalli et al., Biological effects of various regimes of 25-hydroxyvitamin D3 (calcidiol) administration on bone mineral metabolism in postmenopausal women, Clinical Cases in Mineral and Bone Metabolism, 6(2): 169-173 (2009).
Bulla et al., "Renal bone disorders in children: therapy with vitamin D3 or 1,25-dihydroxycholecalciferol," Proc.Eur.Dial.Transplant. Assoc., 16: 644-648 (1979).
Budavari (ed.), Merck Index: an Encyclopedia of Chemicals, Drugs, and Biologicals, 11th Edition, Merck & Co., 9927-9930 (1989).
Buccianti et al., "Effects of Calcifediol Treatment on the Progression of Renal Osteodystrophy during Continuous Ambulatory Peritoneal Dialysis," Nephron, 56:353-356 (1990).
Brown et al., "Vitamin D Analogues for Secondary Hyperparathyroidism," Nephrol Dial Transplant, 17[Suppl. 10]:10-19 (2002).

Brossard et al. "Influence of Glomerular Filtration Rate on Non-(1-84) Parathyroid Hormone (PTH) Detected by Intact PTH Assays," Clinical Chemistry, 46(5):697-703 (2000).
Brodowicz et al., Early identification and intervention matters: A comprehensive review of current evidence and recommendations for the monitoring of bone health in patients with cancer, Cancer Treat Rev., 61:23-34 (2017).
Briese et al., "Arterial and cardiac disease in young adults with childhood-onset end-stage renal disease-impact of calcium and vitamin D therapy," Nephrology Dialysis Transplantation., 21:1906-1914 (2006).
Boxtel et al., "Drug Benefits and Risks, International Textbook of Clinical Pharmacology," p. 75-76 (2001).
Bouillon et al., "Influence of dialysate calcium concentration and vitamin D on serum parathyroid hormone during repetitive dialysis," Kidney Int., 7:422-432 (1975).
Boudville et al., "Renal Function and 25-Hydroxyvitamin D Concentrations Predict Parathyroid Hormone Levels in Renal Transplant Patients," Nephrol Dial Transplant, 21:2621-2624 (2006).
Bordier et al., "Evolution of renal osteodystrophy: Correlation of bone histomorphometry and serum mineral and immunoreactive parathyroid hormone values before and after treatment with calcium carbonate or 25-hydroxycholecalciferol," Kidney Int Suppl, 2:S102-S112 (1975).
Blunt et al., Biological Activity of 25-Hydroxycholecalciferol, A Metabolite of Vitamin D3, Proc. N.A.S., USA, 61(4):1503-6 (1968).
Blair et al., "Prevalence of vitamin D [25(OH)D] deficiency and effects of supplementation with ergocalciferol (vitamin D2) in stage 5 chronic kidney disease patients." J.Ren Nutr., 18: 375-382 (2008).
Bischoff-Ferrari, The 25-hydroxyvitamin D threshold for better health, J. Steroid Biochem. Mol. Biol., 103:614-619 (2007).
Binkley et al., "Laboratory Reporting of 25-Hydroxyvitamin D Results: Potential for Clinical Misinterpretation," Clinical Chemistry, 52(11);2124-2125 (2006).
Bianchi et al., "No Difference in Intestinal Strontium Absorption After an Oral or an Intravenous 1,25(OH)2D3 Bolus in Normal Subjects," J. Bone Miner. Res., 14:1789-1795 (1999).
Bhatia et al., EB1089 inhibits the parathyroid hormone-related protein-enhanced bone metastasis and xenograft growth of human prostate cancer cells, Mol. Cancer Ther., 8(7):1787-98 (2009).
Berruti et al., Prognostic role of serum parathyroid hormone levels in advanced prostate cancer patients undergoing zoledronic acid administration, Oncologist, 17(5):645-52 (2012).
Berg et al., 24,25-Dihydroxyvitamin d3 and vitamin D status of community-dwelling black and white Americans, Clin. Chem., 61(6):877-84 (Jun. 2015).
Belostotsky et al., "A single high dose of ergocalciferol can be used to boost 25-hydroxyvitamin D levels in children with kidney disease," Pediatr Nephrol, 24:625-626 (2009).
Bell et al., "Evidence that 1,25-Dihydroxyvitamin D3 Inhibits the Hepatic Production of 25-Hydroxyvitamin D in Man," J. Clin. Invest., 74:1540-1544 (1984).
Beer et al., "Pharmacokinetics and Tolerability of a Single Dose of DN-101, a New Formulation of Calcitriol, in Patients with Cancer," Clin. Cancer Res., 11:7794-7799 (2005).
Beckman, et al., "Up-Regulation of the Intestinal 1, 25-Dihydroxyvitamin D Receptor During Hypervitaminosis D: A Comparison Between Vitamin D2 and Vitamin D31," Biochemical and Biophysical Research Communications, vol. 169, No. 3, pp. 910-915 (Jun. 29, 1990).
Barreto (25-Hydroxyvitamin D3, the Prohomone of 1, 25-Dihydroxyvitamin D3, Inhibits the Proliferation of Primary Prostatic Epithelial Cell, Cancer Epidemiol Biomarkers Pre 2000, vol. 9, pp. 265-270).
Barger-Lux M.J. et al., "Vitamin D and Its Major Metabolites: Serum Levels After Graded Oral Dosing in Healthy Men" Osteoporosis International, United Kingdom, 8(3):222-230 (1998).
Baird et al., "Steroid Dynamics Under Steady-State Conditions," Recent Prog. Horm. Res., 25:611-664 (1969).
Bailie et al. "Comparative Review of the Pharmacokinetics of Vitamin D Analogues," Seminars in Dialysis, 15(5):352-357 (2000).

(56) References Cited

OTHER PUBLICATIONS

Bagnis et al., "Biochemical and Hormonal Short-Term Effects of 25-hydroxyvitamin D3 in Patients on Continuous Peritoneal Dialysis," Ital. J. Mineral Electrolyte Metab., 12:73-76 (1998).
Baggiolini et al., "Stereocontrolled Total Synthesis of 1 alpha, 25-Dihydroxycholecalciferol 1 and 1 alpha, 25-Dihydroxyergocalciferol," J. Org. Chem. 21: 3098-3108 (1986).
Ashford, Chapter 20: Bioavailability—physicochemical and dosage form factors, pp. 314-333 In: Aulton et al. (eds.), Aulton's Pharmaceutics. The Design and Manufacture of Medicines, Fourth Edition, Elsevier Publishing (2013).
Armas et al., "Vitamin D2 is Much Less Effective than Vitamin D3 in Humans," J. Clin. Endocrinol. Metab., 89:5387-5391 (2004).
Arekat et al., "Dramatic Improvement of BMD Following Vitamin D Therapy in a Bone Marrow Transplant Recipient," J. Clin. Densitometry, 5(3):297-71 (2002).
Andress, "Vitamin D in chronic kidney disease: A systematic role for selective vitamin D receptor activation," Kidney Int., 69:33-43 (2006).
Anderson et al., Quantification of mRNA for the vitamin D metabolizing enzymes CYP27B1 and CYP24 and vitamin D receptor in kidney using real-time reverse transcriptase-polymerase chain reaction, 2003. J. Mol. Endoc 31:123-132.
Anderson et al., Expression of VDR and CYP24A1 mRNA in human tumors, Cancer Chemother. Pharmacol., 57(2):234-40 (2006).
Amin, The impact of improved phosphorus control: use of sevelamer hydrochloride in patients with chronic renal failure, Nephrol Dial Transplant, 17:340-345 (2002).
Alvarez et al., "Vitamin D Supplementation in Pre-Dialysis Chronic Kidney Disease," Dermato-Endocrinology, 4(2):118-127 (2012).
Alfarol (Registered) Capsules 3mg (Package Leaflet, Mar. 2011).
AlfaD3 (Registered) 0.25, 0.5 or 1 microgram Capsules (Alfacalcidol, Package Leaflet, Apr. 2010).
Albertson et al., Quantitative mapping of amplicon structure by array CGH identifies CYP24 as a candidate oncogene, Nat. Genet., 25(2)144-6 (2000).
Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).
"NASMHPD Medical Director's Technical Report on Psychiatric Polypharmacy," Sep. 2001.
"Hidroferol (Registered) (calcifediol): Casos de Hipercalcemia e Hipervitaminosis D," Butlleti de Farmacovigilancia de Catalunya, 9(5):17-20 (2011).
"Guidance for Industry, Nonclinical Safety Evaluation of Drug or Biologic Combinations," U.S. Department of Health and Human Services, Food and Drug Administration (Mar. 2006).
"ACP Formulary and Pocket Guide to Psychopharmacology," Virginia DMHMRSAS, vol. 1, Iss. 1 (2004-2005).
Zuradelli et al., High incidence of hypocalcemia and serum creatinine increase in patients with bone metastases treated with zoledronic acid, Oncologist, 14(5):548-56 (2009).
Zucchelli et al., "Therapeutic effects of 25-hydroxycholecalciferol and sodium etidronate on renal osteodystrophy," Mineral. Electrolyte Metab. 7: 86-96 (1982).
Zisman et al., "Impact of Ergocalciferol Treatment of Vitamin D Deficiency on Serum Parathyroid Hormone Concentrations in Chronic Kidney Disease," Am. J. Nephrol., 27:36-43 (2007).
Zerwekh J. E.: "Blood biomarkers of vitamin D status", The American Journal of Clinical Nutrition, vol. 87Suppl., 2008, pp. 1087S-1091S.
Zerwekh et al., "Extra-Renal Production of 24,25-Dihydroxyvitamin D in Chronic Renal Failure During 25 Hydroxyvitamin D3 Therapy," Kidney Int., 23:401-406 (1983).
Zemplar (Registered) (paricalcitol) Capsules, Final Agreed Upon Label (FDA, May 5, 2009).
Yueh-Ting et al: Comparison between Calcitriol and Caltiriol Plus Low-Dose Cinacalcet for the Treatment of Moderate to Severe Secondary Hyperparathyroidism in Nutrients, vol. 5, No. 4, Apr. 19, 2013 (Apr. 19, 2013), pp. 1336-1348.

Yanoff et al., "The Prevalence of Hypovitaminosis D and Secondary Hyperparathyroidism in Obese Black Americans," Clin. Endocrinol. (Oxf), 64(5):523-529 (2006).
Written Opinion of the International Searching Authority for corresponding international application No. PCT/US2007/071791 (dated Feb. 5, 2008).
Written Opinion for Application No. PCT/US2014/28132, dated Jun. 17, 2014.
Written Opinion for Application No. PCT/US2007/061521, dated Jul. 17, 2007.
Written Opinion for Application No. PCT/IB2008/003480, dated Mar. 31, 2009.
Wootton, "Improving the Measurement of 25-Hydroxyvitamin D," Clin Biochem Rev, 26:33-36 (2005).
Witmer et al., "Effects of 25-hydroxycholecalciferol on bone lesions of children with terminal renal failure" Kidney International 10:395-408 (1976).
Wise (ed.), Handbook of Pharmaceutical Controlled Release Technology, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).
Wagner et al., The ratio of serum 24,25-dihydroxyvitamin D(3) to 25-hydroxyvitamin D(3) is predictive of 25-hydroxyvitamin D(3) response to vitamin D(3) supplementation, J. Steriod Biochem. Mol. Biol., 126(3-5):72-7 (Sep. 2011).
Vieth, "What is the optimal vitamin D status for health?" Prog. Biophys. Mol. Biol., 92:26-32 (2006).
Vieth, "Vitamin D Supplementation, 25-Hydroxyvitamin D Concentrations, and Safety," Am. J. Clin. Nutr., 69:842-856 (1999).
Verberckmoes et al., "Osteodystrophy of Dialysed Patients Treated with Vitamin D," Proc Eur Dial Transplant Assoc., 10(0): 217-226 (1973).
Van Weelden et al., "Apoptotic Regression of MCF-7 Xenografts in Nude Mice Treated with the Vitamin D.sub.3 Analog, EB1089," Endocrinology, 139:2102-2110 (1998).
US FDA Summary of Basis of Approval for Calderol (Registered) calcifediol capsules (believed to be available circa 1980).
US FDA Clinical Review and Evaluation of NDA for Calderol (Registered) calcifediol capsules (believed to be available circa 1983).
Tuohimaa et al., "Both High and Low Levels of Blood Vitamin D are Associated with a Higher Prostate Cancer Risk: A Longitudinal, Nested Case-Control Study in the Nordic Countries," Int. J. Cancer, 108(1):104-108 (2004).
Tsuji, et al. "A New and Convenient Synthesis of 1a,25-Dihydroxyvitamin D2 and It 24R-Epimer," Bull. Chem. Soc. Jpn., 62:10 pp. 3132-3137 (1989).
Trakarnvanich et al., "Effect of high dose ergocalciferol in chronic kidney disease patients with 25-hydroxyvitamin D deficiency," J.Med.Assoc.Thai. 93: 885-891 (2010).
Tomida et al., Serum 25-hydroxyvitamin D as an independent determinant of 1-84 PTH and bone mineral density in non-diabetic predialysis CKD patients, Bone, 44(4):678-83 (Apr. 2009).
Tokmak et al., "High-dose cholecalciferol to correct vitamin D deficiency in haemodialysis patients," Nephrol.Dial.Transplant., 23: 4016-4020 (2008).
Thombre, "Assessment of the feasibility of oral controlled release in an exploratory development setting," Drug Discovery Today, 10(17): 1159-1166 (2005).
Thomas et al., "Hypovitaminosis D in Medical Inpatients," NEJM, 338:777-783 (1998).
Teitelbaum et al., "Tetracycline fluorescence in uremic and primary hyperparathyroid bone," Kidney Int., 12:366-372 (1977).
Teitelbaum et al., "Calcifediol in Chronic Renal Insufficiency" JAMA 235(2):164-167 (1976).
Tebben et al., Elevated fibroblast growth factor 23 in women with malignant ovarian tumors, Mayo Clin. Proc., 80:745-51 (2005).
Taylor, CM, 24,25-Dihydroxyvitamin D in Human Serum. In: Vitamin D. Basic Research and Clinical Applications, pp. 197-203. Walter de Gruyter, New York (1979).
Taylor et al., "The absence of 24,25-dihydroxycholecalciferol in anephric patients," Clin.Sci.Mol.Med.Suppl., 55: 541-547 (1978).

(56) References Cited

OTHER PUBLICATIONS

Taylor et al., "Interrelationship of Serum 25-Hydroxyvitamin D3 and 1,25-Dihydroxyvitamin D in Juvenile Renal Osteodystrophy after Therapy with 25-Hydroxyvitamin D3," Metab. Bone Dis. & Rel. Res., 4:255-261 (1982).
Tamez et al., Vitamin D reduces left atrial volume in patients with left ventricular hypertrophy and chronic kidney disease, Am. Heart J., 164(6):902-9.e2 (Dec. 2012).
Szycher, Szycher's Dictionary of Biomaterials and Medical Devices, pp. 20, 48, 127, Lancaster, Penn: Technomic Publishing Co., Inc. (1992).
Supplementary European Search Report for Application No. 09729007.6, dated Apr. 18, 2011.
Stumpf, "The Dose Makes the Medicine," Drug Discovery Today, 11:550-555 (2006).
Stubbs et al., "Cholecalciferol supplementation alters calcitriol-responsive monocyte proteins and decreases inflammatory cytokines in ESRD," J.Am.Soc.Nephrol., 21: 353-361 (2010).
Stein et al., "An Update on the Therapeutic Potential of Vitamin D Analogues," Expert Opin. Investig. Drugs, 12:825-840 (2003).
Stavroulopoulos et al., Relationship between vitamin D status, parathyroid hormone levels and bone mineral density in patients with chronic kidney disease stages 3 and 4, Nephrology (Carlton), 13(1):63-7 (Feb. 2008).
Stamp, "Intestinal Absorption of 25-hydroxycholecalciferol," The Lancet, 121-123 (1974).
Stamp et al., "Comparison of Oral 25-Hydroxycholecalciferol, Vitamin D, and Ultraviolet Light as Determinants of Circulating 25-Hydroxyvitamin D," The Lancet, 1341-1343 (Jun. 25, 1977).
Sprague et al., Use of Extended-Release Calcifediol to Treat Secondary Hyperparathyroidism in Stages 3 and 4 Chronic Kidney Disease, Am. J. Nephrol., 44(4):316-25 (2016).
Sprague et al., Modified-release calcifediol effectively controls secondary hyperparathyroidism associated with vitamin D insufficiency in chronic kidney disease, Am. J. Nephrol., 40(6):535-45 (2015).
Sprague et al., Modified-Release Calcifediol Effectively Controls Secondary Hyperparathyroidism Associated with Vitamin D Insufficiency in Chronic Kidney Disease, American Journal of Nephrology, vol. 40, No. 6, Jan. 7, 2015 (Jan. 7, 2015), pp. 535-545.
Soyfoo et al., Non-malignant causes of hypercalcemia in cancer patients: a frequent and neglected occurrence, Support Care Cancer, 21(5):1415-9 (2013).
Sosa et al., "The Effect of 25-dihydroxyvitamin D on the Bone Mineral Metabolism of Elderly Women with Hip Fracture," Rheumatology, 39:1263-1268 (2000).
Sommerfeldt et al., "Metabolism of Orally Administered [3H]Ergocalciferol and [3H]Cholecalciferol by Dairy Calves," J. Nutr., 113:2595-2600 (1983).
Somjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," Steroids, 63:340-343 (1998).
Somerville et al., "Resistance to Parathyroid Hormone in Renal Failure: Role of Vitamin D Metabolites," Kidney Int., 14:245-254 (1978).
Slatopolsky et al., "Differential Effects of 19-nor-1,25-(OH)2D2 and 1a-Hydroxyvitamin D2 on Calcium and Phosphorus in Normal and Uremic Rats," Kidney International, 62:1277-1284 (2002).
Skugor M. et al.: Evolution and current state of assays for parathyriod hormone, Biochemia Medica, vol. 20, No. 2, 2010, pp. 221-228.
Skelly et al., In vitro and in vivo testing an correlation for oral controlled/modified-release dosage forms. Pharm. Res., 7(9):975-82 (1990).
Sjoden, et al., "1.alpha.-Hydroxyvitamin D2 is Less Toxic than 1.alpha.-Hydroxyvitamin D3 in the Rat," Society for Experimental Biology and Medicine, 179: 432-436 (1985).
Sitrin et al., Comparison of vitamin D and 25-hydroxyvitamin D absorption in the rat, Am. J. Physiol., 242(4):G326-32 (1982).
Singh et al., "C-3 Epimers Can Account for a Significant Proportion of Total Circulating 25-Hydroxyvitamin D in Infants, Complicating Accurate Measurement and interpretation of Vitamin D Status," J. Clin. Endo. & Metabol., 91(8):3055-3061 (2006).
Sicinski et al., "Synthesis of 1 alpha, 25-Dihydroxyvitamin D2, Its 24 Epimer and Related Isomers, and Their Binding Affinity for the 1, 25-Dihydroxyvitamin D3 Receptor," Bioorganic Chemistry, 13: 158-169 (1985).
Shi et al., "Preparation of Chitosan/Ethylcellulose Complex Microcapsule and its Application in Controlled Release of Vitamin D2," Biomaterials, 23:4469-4473 (2002).
Shah et al., "Prevalence and correction of 25(OH) vitamin D deficiency in peritoneal dialysis patients," Peritoneal Dialysis Int., 25:362-366 ( 2005).
Sensipar (cinacalcet) prescriptioninformation, revised Aug. 2011.
Sekkarie, "The Impact of Over-the-counter Vitamin D Supplementals on Vitamin D and Parathyroid Hormone Levels in Chronic Kidney Disease," Clin. Nephrology, 65:91-96 (2006).
Segersten et al.: Potentiating effects of nonactive/active vitamin D analogues and ketoconazole in parathyroid cells, Clinical Endocrinology., vol. 66, No. 3, Mar. 1, 2007 (Mar. 1, 2007), pp. 399-404.
Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," Metab. Bone Dis. & Rel. Res., 2:217-222 (1980).
Sebert et al., "Effets a Long Terme D'Une Association De 25-Hydroxycholecalciferol et de 1-Alpha-Hydroxycholecalciferol Sur L'Osteodystrophie Des Hemodialyses Chroniques" Rev. Rhum Mal Osteoartic 48(7-9):535-541 (1981).
Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Schmidt, "Measurement of 25-Hydroxyvitamin D Revisited," Clinical Chemistry, 52(12):2304-2305 (2006).
Sato et al., Increased 1,25-(OH)2D2 concentration in a patient with malignancy-associated hypercalcemia receiving intravenous hyperalimentation inadvertently supplemented with vitamin D2, Intern. Med., 32(11):886-90 (1993).
Saseen et al., "Dual calcium-channel blocker therapy in the treatment of hypertension," Ann Pharmacother., 30(7-8): 802-10 (1996).
Sanchez, "Prevention and Treatment of Renal Osteodystrophy in Children With Chronic Renal Insufficiency and End-Stage Renal Disease," Seminars in Nephrology, 21:441-450 (2001).
Saab et al., "Prevalence of Vitamin D Deficiency and the Safety and Effectiveness of Monthly Ergocalciferol in Hemodialysis Patients," Nephron Clin. Pract., 105:c132-c138 (2007).
Rutherford et al., "Effect of 25-Hydroxycholecalciferol on Calcium Absorption in Chronic Renal Disease," Kidney International, 8:320-324 (1975).
Russell et al., "Therapeutic Effects of 25-Hydroxyvitamin D3 on Renal Osteodystrophy," Mineral Electrolyte Metab., 1:129-138 (1978).
Rucker et al., "Vitamin D insufficiency and treatment with oral vitamin D3 in northern-dwelling patients with chronic kidney disease," J.Nephrol. 22: 75-82 (2009).
Rocaltrol (Registered) Complete Product Information, Roche, Jul. 27, 2004.
Rix et al., "Effect of 18 Months of Treatment with Alfacalcidol on Bone in Patients with Mild to Moderate Chronic Renal Failure," Nephrol Dial Transplant, 19:870-876 (2004).
Ritter et al., "25-Hydroxyvitamin D3 suppresses PTH synthesis and secretion by bovine parathyroid cells," Kidney Int., 70:654-659 (2006).
Richard et al., PTHrP gene expression in cancer: do all paths lead to Ets?, Crit. Rev. Eukaryot. Gene Expr., 15(2):115-32 (2005).
Reichel, "Current treatment options in secondary renal hyperparathyroidism," Nephrol Dial Transplant 21:23-28 (2006).
Reichel et al., "Intermittent Versus Continuous Administration of 1,25-dihydroxyvitamin D3 in experimental renal hyperparathyroidism," Kidney Int., 44:1259-1265 (1993).

(56) References Cited

OTHER PUBLICATIONS

Reichel et al., "Calcium Metabolism in Early Chronic Renal Failure: Implications for the Pathogenesis of Hyperparathyroidism," Nephrol. Dial. Transplant., 6:162-169 (1991).
Reddy et al., Abstracts Sixth Annual Scientific Meeting of the American Society for Bone and Mineral Research, 36:524 (1984).
Recker et al., "The Efficacy of Calcifediol in Renal Osteodystrophy," Arch. Intern. Med., 138:857-863 (1978).
Ravani et al., Vitamin D levels and patient outcome in chronic kidney disease, Kidney Int., 75(1):88-95 (Jan. 2009).
Rapuri, P.B. et al., "Effect of Vitamins D2 and D3 Supplement Use on Serum 25-OHD Concentration in Elderly Women in Summer and Winter," Calcified Tissue International, 74(2):150-156 (2004).
Rambeck et al., "Biological Activity of 1alpha,25-Dihydroxyergocalciferol in Rachitic Chicks and in Rats," IZVIAK, 54(2/3):135-139 (1984).
Rabbani, Molecular mechanism of action of parathyroid hormone related peptide in hypercalcemia of malignancy: therapeutic strategies (review), Int. J. Oncol., 16(1):197-206 (2000).
Querfeld et al., Vitamin D deficiency and toxicity in chronic kidney disease: in search of the therapeutic window, Pediatr. Nephrol., 25(12):2413-30 (Dec. 2010).
Prescribing information for Zemplar (Registered) (paricalcitol) Capsules, Abbott (2011).
Prescribing Information for Hectorol (Registered) (doxercalciferol capsules), Genzyme (2011).
Prescribing Information for Calderol (Registered) calcifediol capsules (1988).
Pourgholami et al., "In Vitro Antiproliferative Activity of a Medium-Chain Triglyceride Solution of 1, 25-Dihydroxyvitamin D3 in HepG2 Cells," Anticancer Res., 20:4257-4260 (2000).
Pourgholami et al., "1, 25-Dihydroxyvitamin D3 Dissolved in Lipiodol Produces a Sustained Antiproliferative Effect in the Human Hepatoblastoma Cell Line HepG2," Anticancer Res., 20:723-728 (2000).
Posner et al., "Vitamin D Analogues Targeting CYP24 in Chronic Kidney Disease," J. Steroid Biochem and Mol. Biol., 121:13-19 (2010).
Phadnis et al., "Direct, Rapid Effects of 25-Hydroxyvitamin D3 on Isolated Intestinal Cells," J. Cell. Biochem., 90:287-293 (2003).
Petkovich et al., "CYP24A1 and Kidney Disease," Current Opin. In Nephrology and Hypertension, 20:337-344 (2011).
Perrie, Pharmaceutics: Drug Delivery and Targeting, Second Edition, Chapter 1 (2012).
Peacock et al., "Effect of Calcium or 25OH Vitamin D3 Dietary Supplementation on Bone Loss at the Hip in Men and Women over the Age of 60" The Journal of Clinical Endocrinology & Metabolism, 85(9):3011-3019 (2007).
Patel et al., "Glomerular Filtration Rate is a Major Determinant of the Relationship Between 25-Hydroxyvitamin D and Parathyroid Hormone," Calcif. Tissue Int., 80:221-226 (2007).
Horst et al., "Rat cytochrome P450C24 (CYP24) does not metabolize 1,25-dihydroxyvitamin D2 to calcitroic acid," J. Cell Biochem., 88:282-285 (2003).
Horst et al., "Discrimination in the Metabolism of Orally Dosed Ergocalciferol and Cholecalciferol by the Pig, Rat and Chick," Biochem. J., 204:185-189 (1982).
Horst et al., "A Sensitive Competitive Protein Binding Assay for Vitamin D in Plasma," Steroids, 37:581-592 (1981).
Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).
Hollis, "Circulating 25-Hydroxyvitamin D Levels Indicative of Vitamin D Sufficiency: Implications for Establishing a New Effective Dietary Intake Recommendation for Vitamin D," J. Nutr. 135: 317-322 (2005).
Holick, Vitamin D for health and in chronic kidney disease, Semin. Dial., 18(4):266-75 (2005).
Holick, "Vitamin D: A Millenium Perspective," Journal of Cellular Biochemistry, 88:296-307 (2003).
Holick, "Vitamin D Status: Measurement, Interpretation and Clinical Application," Ann Epidemiol, 19(2):73-78 (2009).
Holick, "Vitamin D Deficiency in CKD: Why Should We Care?" Am. J. Kidney Dis., 45:1119-1121 (2005).
Holick et al., Evaluation, treatment, and prevention of vitamin D deficiency: an Endocrine Society clinical practice guideline, J. Clin. Endocrinol. Metab., 96(7):1911-30 (Jul. 2011).
Holick et al., "Vitamin D2 is as effective as vitamin D3 in maintaining circulating concentrations of 25-dydroxyvitamin D," J Clin Endocrinol Metab., 93(3):677-81 (2008).
Hodson et al., "Treatment of childhood renal osteodystrophy with calcitriol or ergocalciferol," Clin Nephrology, 24(4): 192-200 (1985).
Henry et al., Response of chick parathyroid glands to the vitamin D metabolites, 1,25-dihydroxycholecalciferol and 24,25-dihydroxycholecalciferol, J. Nutr., 107(10):1918-26 (1977).
Helvig et al., Dysregulation of renal vitamin D metabolism in the uremic rat, Kidney Int., 78(5):463-72 (2010).
Hectorol (Registered) (doxercalciferol) Capsules (Label, FDA, 2010).
Hay et al., "Vitamin D2 in Vertebrate Evolution," Comp. Biochem. Physiol. B, 56:375-380 (1977).
Harris R Z et al: "Pharmacokinetics of cinacalcet hydrochloride when administered with ketoconazole", Clinical Pharmacokinetics, Adis International Ltd., Auckland, NZ, vol. 46, No. 6, Jan. 1, 2007 (Jan. 1, 2007), pp. 495-501.
Hari et al., "Vitamin D insufficiency and effect of cholecalciferol in children with chronic kidney disease," Pediatr.Nephrol,. 25: 2483-2488 (2010).
Hannula et al., "Constant, But Not Pulsed Calcitriol Suppresses Hemodialysis Patients' Antigen-Induced Lymphocyte Proliferation," Nephron, 86:139-144 (2000).
Hamida et al., "Hyperparathyroidie secondaire al insuffisance renale" Annales d'Endocrin-ologie 55:147-158 (1994) [reference in French].
Halloran et al., "Plasma Vitamin D Metabolite Concentrations in Chronic Renal Failure: Effect of Oral Administration of 25-Hydroxyvitamin D3," J. Clin. Endocrin. & Metab., 59:1063-1069 (1984).
Haldimann et al., "Effect of an Oral Dose of 25-Hydroxyvitamin D3 on Its Blood Levels in Patients with the Nephrotic Syndrome," J Clin Endocrinology and Metabolism, 50(3): 470-474 (1980).
Haddad, "Vitamin D—Solar Rays, the Milky Way, or Both?" NEJM, 326:1213-1215 (1992).
Haddad, "Traffic, Binding and Cellular Access of Vitamin D Sterols," Bone and Mineral Res., Elsevier, 5:281-308 (1987).
Haddad, "Seasonal Diminution of Vitamin D Stores in the United States: Can Darker Winters Lead to Lighter Bones?" Trends Endocrinol. Metab., 7:209-212 (1996).
Haddad, "Plasma Vitamin D-binding Protein (Gc-Globulin): Multiple Tasks," J. Steroid Biochem. Molec. Biol., 53:579-582 (1995).
Haddad et al., Human serum binding capacity and affinity for 25-hydroxyergocalciferol and 25-hydroxycholecalciferol, J. Clin. Endocrinol. Metab., 43(1):86-91 (1976).
Haddad et al., "Vitamin D Plasma Binding Protein. Turnover and Fate in the Rabbit," J. Clin. Invest., 67(5):1550-1560 (1981).
Haddad et al., "Natural and Synthetic Sources of Circulating 25-Hydroxyvitamin D in Man," Nature, 244:515-517 (1973).
Haddad et al., "Human Serum Binding Capacity and Affinity for 25-Hydroxyergocalciferol and 25-Hydroxycholecalciferol," J. Clin. Endocrinol. Metab., 43:86-91 (1976).
Haddad et al., "Acute Administration of 25-Hydroxycholecalciferol in Man," J. Clin. Endocrinol. Metab., 42:284-289 (1976).
Granja et al., "Studies on the Opening of Dioxanone and Acetal Templates and Application to the Synthesis of 1 alpha, 25-Dihydroxyvitamin D21," J. Org. Chem., 58:124-131 (1993).
Gopinath et al., Disintegrants—A Brief Review, J. Chem. Pharm. Sci., 5(3):105-12 (Jul.-Sep. 2012).
Goodman, Calcimimetic agents and secondary hyperparathyroidism: treatment and prevention, Nephrol Dial Transplant, 17: 204-7 (2002).
Gomez-Alonso et al., "Vitamin D Status and Secondary Hyperparathyroidism: The Importance of 25-Hydroxyvitamin D Cut-Off Levels," Kidney International, 63(Supp. 85):S44-548 (2003).

(56) References Cited

OTHER PUBLICATIONS

Gibson, ed., Product optimisation. Pharmaceutical Preformulation and Formulation: A Practical Guide from Candidate Drug Selection to Commercial Dosage Form, 295-8 (2004).
Ghazali et al., "Is low plasma 25-(OH) vitamin D a major risk factor for hyperparathyroidism and Looser's zones independent of calcitriol?" Kidney International 55:2169-2177 (1999).
Garland et al., Vitamin D for cancer prevention: global perspective, Ann. Epidemiol., 19(7):468-83 (2009).
Gallagher et al., "Comparison of the Histological Effect and Metabolism of 25-(OH)D and 1,25-(OH)2D in Rat Bone," p. 399-401, In: Norman, Vitamin D: Basic Research and its Clinical Application: Proceedings of the Fourth Workshop on Vitamin D, Berlin, West Germany, Feb. 1979.
Gal-Moscovici et al., Role of vitamin D deficiency in chronic kidney disease, Journal of Bone and Mineral Res. 22:V91-V94 (2007).
Fukagawa et al., With or without the kidney: the role of FGF23 in CKD, Nephrol. Dial. Transplant., 20:1295-8 (2005).
Fukagawa et al., FGF23: its role in renal bone disease, Pediatr. Nephrol., 21:1802-6 (2006).
Frost et al., "Histomorphometric Changes in Trabecular Bone of Renal Failure Patients Treated with Calcifediol," Metab. Bone Dis. & Rel. Res., 2:285-295 (1981).
Frohling et al., "Serum 25-hydroxyvitamin D in patients with chronic renal failure on long-term treatment with high doses of vitamin D2." Nephron 26: 116-120 (1980).
Fritsche et al., "Regulation of 25-Hydroxyvitamin D3-1a-Hydroxylase and Production of 1a,25-Dihydroxyvitamin D3 by Human Dendritic Cells," Blood, 102(9):3314-3316 (2003).
Friedrich et al., Analysis of the vitamin D system in cervical carcinomas, breast cancer and ovarian cancer, Recent Results Cancer Res., 164:239-46 (2003).
Friedman et al. "The Role of Vitamin D in Mild to Moderate Chronic Kidney Disease," Trends in Endocrinology & Metab,. 13(5):189-194 (2002).
Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).
Fournier et al., Prevention of secondary hyperparathyroidism in chronic renal failure before dialysis, Contrib. Nephrol., 71:64-80 (1989).
Fournier et al., "Traitement vitaminique D et osteodystrophies renales: indications et modalities" Nephrologie 16(2):165-190 (1995) [journal in French].
Bertoldo et al., Serum 25-hydroxyvitamin D levels modulate the acute-phase response associated with the first nitrogen-containing bisphosphonate infusion, J. Bone Miner. Res., 25(3):447-54 (Mar. 2010).
Charnow, Novel Formulation Corrects Vitamin D, Lowers iPTH, Renal & Urology News (2012).
Japanese Patent Application No. 2017-506724, Office Action, dated May 27, 2019.
Martin-Baez et al., Severe hypocalcaemia post-denosumab, Nefrologia, 33(4):614-5 (2013).
Opko Health Inc., Safety/Efficacy Study of CTAP101 in Chronic Kidney Disease Subjects With Secondary Hyperparathyroidism (SHPT), <https://clinicaltrials.gov/ct2/show/NCT01219855> Oct. 13, 2010.
Wang-Gillam et al., Evaluation of vitamin D deficiency in breast cancer patients on bisphosphonates, Oncologist, 13(7):821-7 (Jul. 2008).

\* cited by examiner

ADJUNCTIVE THERAPY WITH 25-HYDROXYVITAMIN D AND ARTICLES THEREFOR

CROSS-REFERENCE TO RELATED APPLICATIONS

This is a continuation-in-part of International Patent Application No. PCT/EP2015/068219 filed Aug. 6, 2015, which claims the benefit of priority under 35 U.S.C. § 119(e) of U.S. Provisional Patent Application Ser. No. 62/034,604 filed Aug. 7, 2014. The disclosure of each priority application is hereby incorporated herein by reference.

BACKGROUND

The Vitamin D metabolites known as 25-hydroxyvitamin $D_2$ and 25-hydroxyvitamin $D_3$ (collectively referred to as "25-hydroxyvitamin D") are Vitamin D prohormones that contribute to the maintenance of adequate levels of Vitamin D hormones, calcium and phosphorus in the bloodstream. The prohormone 25-hydroxyvitamin $D_2$ is produced from Vitamin $D_2$ (ergocalciferol), and 25-hydroxyvitamin $D_3$ (calcifediol) is produced from Vitamin $D_3$ (cholecalciferol), primarily by one or more enzymes located in the liver. The two prohormones also can be produced outside of the liver from Vitamin $D_2$ and Vitamin $D_3$ (collectively referred to as "Vitamin D") in certain cells, such as enterocytes, which contain enzymes identical or similar to those found in the liver.

The Vitamin D prohormones are further metabolized in the kidneys by the 1α-hydroxylase enzyme CYP27B1 into potent hormones. The prohormone 25-hydroxyvitamin $D_2$ is metabolized into a hormone known as 1α,25-dihydroxyvitamin $D_2$ (ercalcitriol); likewise, 25-hydroxyvitamin $D_3$ is metabolized into 1α,25-dihydroxyvitamin $D_3$ (calcitriol). Production of these hormones from the prohormones also can occur outside of the kidney in cells which contain the required enzyme(s).

The Vitamin D hormones have essential roles in human health which are mediated by intracellular Vitamin D receptors (VDR). The Vitamin D hormones participate in the regulation of cellular differentiation and growth, parathyroid hormone (PTH) secretion by the parathyroid glands, and normal bone formation and metabolism. In particular, the Vitamin D hormones regulate blood calcium levels by controlling the absorption of dietary calcium and phosphorus by the small intestine and the reabsorption of calcium by the kidneys. Under normal conditions, actions of Vitamin D on stimulating intestinal calcium absorption predominate, such that dietary calcium is the main source of serum calcium. However if dietary calcium or vitamin D is insufficient, the parathyroid gland increases secretion of PTH to enhance calcium mobilization from bone to maintain serum calcium levels. Excessive hormone levels, whether transient or prolonged, can lead to abnormally elevated urine calcium (hypercalciuria), blood calcium (hypercalcemia) and blood phosphorus (hyperphosphatemia). Insufficient hormone levels can lead to the opposite syndrome of abnormally low blood calcium levels (hypocalcemia). Vitamin D hormones are also required for the normal functioning of the musculo skeletal, immune and renin-angiotensin systems. Numerous other roles for Vitamin D hormones are being postulated and elucidated, based on the documented presence of intracellular VDR in nearly every human tissue.

Left untreated, inadequate Vitamin D supply can cause serious bone disorders, including rickets and osteomalacia, and may contribute to the development of many other disorders including osteoporosis, non-traumatic fractures of the spine and hip, obesity, diabetes, muscle weakness, immune deficiencies, hypertension, psoriasis, and various cancers.

The Institute of Medicine (IOM) of the National Academy of Sciences has concluded that an Adequate Intake (AI) of Vitamin D for a healthy individual ranges from 200 to 600 IU per day, depending on the individual's age and sex (Standing Committee on the Scientific Evaluation of Dietary Reference Intakes, *Dietary reference intakes: calcium, phosphorus, magnesium, vitamin D, and fluoride*. Washington, D.C.: National Academy Press (1997), incorporated by reference). The AI for Vitamin D was defined primarily on the basis of a serum 25-hydroxyvitamin D level sufficient to prevent Vitamin D deficiency rickets or osteomalacia (or greater than or equal to 11 ng/mL). The IOM also established a Tolerable Upper Intake Level (UL) for Vitamin D of 2,000 IU per day, based on evidence that higher doses are associated with an increased risk of hypercalciuria, hypercalcemia and related sequelae, including cardiac arrhythmias, seizures, and generalized vascular and other soft-tissue calcification.

Currently available oral Vitamin D supplements are far from ideal for achieving and maintaining optimal blood 25-hydroxyvitamin D levels. These preparations typically contain 400 IU to 5,000 IU of Vitamin $D_3$ or 50,000 IU of Vitamin $D_2$ and are formulated for quick or immediate release in the gastrointestinal tract. When administered at chronically high doses, as is often required for Vitamin D repletion, these products have significant, and often severe, limitations.

Abnormalities of Vitamin D signaling and metabolism exist in a wide variety of tumors (Krishnan et al., (2012). *Rheum Dis Clin North Am* 38, 161-178) and are thought to be due to increased expression of CYP24 (Luo et al., (2013) *J Steroid Biochem Mol Biol* 136, 252-257). Cancer patients generally exhibit vitamin D insufficiency, therefore, calcium resorption from bone calcium stores plays a dominant role in the normalization of blood calcium levels. Regardless of the cancer type, low serum levels of 25-hydroxyvitamin D and decreased VDR activation have been associated with increased metastasis. Cancer mortality is usually a consequence of metastasis. For certain types of cancer, notably breast and prostate, the bulk of tumor burden at the time of death is in bone. The impact of metastasis on bone metabolism and consequent morbidity is considerable and, depending on the origin of the primary tumor, is either osteolytic (e.g., breast, myeloma) or osteoblastic (e.g., prostate) in nature. However, since bone formation and bone resorption are coupled, "osteolytic" and "osteoblastic" categorizations correspond to the net balance of bone metabolism associated with metastases. A number of factors released from tumors can affect net balance of bone metabolism, including parathyroid hormone related peptide (PTHrP), transforming growth factor-β (TGF-β), insulin-like growth factors (IGF), bone morphogenetic factors (BMP) and platelet-derived growth factors (PDGF).

PTHrP is produced by certain types of cancer cells, such as breast, and can trigger net bone resorption by stimulating the production of the ligand for the receptor activator of NFκB (RANKL) (Rabbani, S. A. (2000). *Int J Oncol* 16, 197-206.; Soyfoo et al. (2013). *Support Care Cancer* 21, 1415-1419). Like PTH, PTHrP can be regulated by activating the Vitamin D signaling pathway (Bhatia et al. (2009). *Mol Cancer Ther* 8, 1787-1798; El Abdaimi et al. (1999). *Cancer Res* 59, 3325-3328.). Consequently, the use of Vitamin D and related analogs has been proposed to help control excessive hypercalcemia caused by PTHrP overexpression in breast and prostate cancers (Richard et al. (2005) *Crit Rev Eukaryot Gene Expr* 15, 115-132.). The majority of instances of hypercalcemia in cancer patients are thought to be related to the production of PTHrP (Motellon et al. (2000) *Clin Chim Acta* 290, 189-197.). In some cases, hypercalcemia of malignancies has been associated with the use of Vitamin D or calcifediol and is related to elevated PTHrP expression. Like PTH, PTHrP expression can increase expression of CYP27B1, the kidney enzyme responsible for activating calcifediol. Therefore, a cancer patient with vitamin D insufficiency and higher than normal levels of PTHrP could potentially express increased levels of unoccupied CYP27B1; a sudden bolus of calcifediol could cause a surge in 1,25-dihydroxyvitamin D and potentially result in hypercalcemic episodes (Motelion et al 2000, supra; Sato et al. (1993). *Intern Med* 32, 886-890.) and further upregulation of CYP24. These hypercalcemic episodes, in contrast to those caused by PTHrP stimulation of RANKL, are due to increased rate of intestinal absorption of Ca.

The relationship between the progression of tumor metastases and bone catabolism is determined to a large extent on the tumor microenvironment within bone. In certain types of cancers, such as prostate cancer, bone formation can be stimulated by TGF-β, IGFs, PDGF and BMPs and these factors play an important role in establishing the bone microenvironment. These patients can suffer from hypocalcemia, which is the reduction of serum calcium levels in the blood. Severe hypocalcemia is sometimes referred to as "hungry bone" syndrome. Accordingly, the state of bone health may be an important determinant of the progression of the metastatic process, including the tumor cell invasion of bone, the angiogenic response, and tumor cell proliferation, as well as differentiation of bone cell precursors into osteoblasts and osteoclasts. There is evidence that vitamin D status may have an influence on each of these parameters, suggesting that vitamin D adequacy may be essential to minimize the progression of bone metastases. Although numerous clinical studies have attempted to raise Vitamin D levels for the treatment of various cancers, currently available therapies do not safely raise 25-hydroxyvitamin D levels high enough to establish the impact 25-hydroxyvitamin D has on tumor growth and metastasis or associated morbidities.

Because bone resorption is a common pathophysiology of bone metastases regardless of primary tumor type, patients are typically treated with bone antiresorptive agents, which inhibit bone resorption by targeting bone osteoclasts to decrease their osteolytic activity. Antiresorptive therapies, also known as bone-sparing agents, reduce the impact of cancer-related increases in bone resorption. Antiresorptive agents can prevent or delay skeletal related events (SRE). SRE are defined as pathological fractures, radiation or surgery to bone, and spinal cord compression, and are used to evaluate the clinical efficacy of antiresorptive agents because SRE are associated with poor prognosis and quality of life. Because antiresorptive agents can slow bone loss, they are also prescribed for patients with osteoporosis and other bone disorders. Examples of antiresorptive agents include bisphosphonates such as zoledronic acid, selective estrogen receptor modulators (SERMs), calcitonin, estrogen, and monoclonal antibodies such as denosumab. Treatment with antiresorptive agents also reduces the efficiency of PTH-stimulated resorption of bone, thus patients must rely on intestinal absorption of calcium for maintaining serum calcium levels.

One of the most important and immediate side effects of antiresorptive agents is hypocalcemia. Other therapeutic agents that can increase the risk of hypocalcemia include anticonvulsant agents, corticosteroids, antihypercalcemia agents, antimicrobial agents, and combinations thereof. Serum calcium is critical for the normal function of nerves and muscles in the body, and serum calcium levels are tightly regulated within narrow limits in healthy subjects. Hypocalcemia can be a significant source of morbidity and mortality. Severe hypocalcemia, in which serum calcium levels are reduced to below the lower limit of normal, can result in life-threatening consequences, including muscle tetany and cardiac arrest. Such treatment-induced, also known as iatrogenic, hypocalcemia, can be serious, even fatal, and therefore must be controlled.

Following administration of the antiresorptive agent denosumab, hypocalcemia is believed to result directly from the inhibitory effects of denosumab on the activity and numbers of bone-resorbing osteoclastic bone cells. Clinical studies have suggested reduced levels of calcium in the blood as soon as one day after initiation of denosumab treatment. Similarly, in a recent study of patients with bone metastases treated with the antiresorptive agent zoledronic acid, 39% of the patients developed hypocalcemia (Zuradelli et al., (2009) *Oncologist* 14, 548-556). Hypocalcemia is one of the most common adverse reactions resulting in discontinuation of therapy with zoledronic acid or denosumab.

Another example of a therapeutic agent that can increase the risk of hypocalcemia is the antihypercalcemia agent cinacalcet (SENSIPAR, Amgen Inc., Thousand Oaks, Calif.). Cinacalcet activates calcium-sensing receptors in the body and lowers serum calcium. See, e.g., U.S. Pat. Nos. 6,001,884 and 6,211,244, incorporated herein by reference. Cinacalcet is currently indicated for treating secondary hyperparathyroidism in patients having Chronic Kidney Disease (CKD) on dialysis (i.e., CKD Stage 5) and hypercalcemia in patients with parathyroid carcinoma or primary hyperparathyroidism. Cinacalcet may cause significant reductions in serum calcium that can lead to hypocalcemia and/or seizures and is contraindicated for use in patients who are already hypocalcemic and also is not indicated for use in CKD patients who are not on dialysis due to the increased risk of hypocalcemia. It is contemplated that the compositions and methods herein can be useful in patients having CKD Stage 5, or in another embodiment in patients having CKD Stage 4. It is contemplated that the compositions and methods herein can be useful in patients having CKD and on dialysis, or in another embodiment, patients not on dialysis.

Vitamin D supplementation is therefore recommended for patients on antiresorptive therapy and/or therapy including an agent that increases the risk of hypocalcemia such as cinacalcet. The treatment protocols in published repeat-dose clinical studies for denosumab have uniformly called for denosumab-treated subjects to receive daily supplements of calcium (0.5 to 1.0 g or more) and at least 400 to 800 IU vitamin D (cholecalciferol and/or ergocalciferol) in order to prevent hypocalcemia. Recommendations for calcium and vitamin D supplementation of denosumab-treated subjects have been included in the FDA-approved labeling for denosumab. However, currently available oral vitamin D supplements are not optimal for increasing and maintaining serum levels of either 25-hydroxyvitamin D or 1,25-dihydroxyvitamin D at desirable levels. The inadequacy of currently available vitamin D supplements at completely mitigating hypocalcemia in denosumab-treated subjects is highlighted by a recent Advisory from Health Canada, which noted that postmarketing cases of severe symptomatic hypocalcemia have occurred in denosumab-treated subjects at an estimated rate of 1 to 2%, including some cases that were fatal.

Another side effect of antiresorptive agents and other agents that increase the risk of hypocalcemia is secondary hyperparathyroidism (SHPT). Decreases in serum calcium can result in increased production of PTH. Elevated PTH levels are common in patients undergoing treatment with antiresorptive agents, indicating an increased vitamin D requirement. Regulation of blood calcium requires adequate production of calcitriol, which stimulates intestinal absorption of dietary calcium and reabsorption of calcium by the kidney. Calcitriol, in concert with elevated PTH, also mobilizes calcium from bone. Adequate calcitriol production requires a sufficient supply of the precursor, calcifediol, and the first sign of inadequate calcitriol production is an increase in plasma PTH. PTH stimulates expression of CYP27B1 in the kidney and, thereby, increases conversion of calcifediol to calcitriol. When serum calcitriol levels are restored to adequate levels, PTH secretion decreases. If serum calcitriol levels cannot be corrected, as in the case of a calcifediol supply shortage (i.e., vitamin D insufficiency), plasma PTH remains elevated causing continuous mobilization of calcium from bone. A recent study (Berruti et al. (2012) *Oncologist* 17, 645-652) reported that 82% to 90% of subjects with prostate cancer metastatic to bone and receiving zoledronic acid exhibited elevated PTH, compared to 17% of patients receiving placebo. The elevated PTH was negatively associated with survival. The prevalence and persistence of SHPT in patients on antiresorptive therapies even though supplemented with Vitamin D and calcium indicates that appropriate supplementation regimens have not yet been clearly defined for this patient population, and the efficacy of antiresorptive agents can be limited by even mild hypocalcemia and/or SHPT.

Clearly, an alternative approach to currently available Vitamin D supplementation is needed in patients with cancer and in patients treated with an agent that increases the risk of hypocalcemia.

SUMMARY

The present disclosure relates to 25-hydroxyvitamin D therapy as adjunctive therapy and/or to treat cancer in a patient.

In one aspect, a method of treating or preventing iatrogenic hypocalcemia and/or secondary hyperparathyroidism in a patient treated with an agent that increases the risk of hypocalcemia comprises administering to the patient an effective amount of 25-hydroxyvitamin D, for example, administering a pharmaceutical formulation comprising (a) a 25-hydroxyvitamin D compound and (b) an agent that increases the risk of hypocalcemia, optionally cinacalcet or a salt thereof, described herein.

In another aspect, a method of increasing bone mineral density in a patient treated with an agent that increases the risk of hypocalcemia comprises administering to the patient an effective amount of 25-hydroxyvitamin D.

In another aspect, a method of decreasing the blood level of a bone resorption marker in a patient treated with an agent that increases the risk of hypocalcemia comprises administering to the patient an effective amount of 25-hydroxyvitamin D. In another aspect, a method of treating bone pain in a patient treated with an agent that increases the risk of hypocalcemia comprises administering to the patient an effective amount of 25-hydroxyvitamin D.

In another aspect, a method of increasing the time to the first post-treatment skeletal-related event in a patient treated with an agent that increases the risk of hypocalcemia comprises administering to the patient an effective amount of 25-hydroxyvitamin D. In another aspect, a method of treating a patient treated with an agent that increases the risk of hypocalcemia comprises administering to the patient an effective amount of 25-hydroxyvitamin D to effectively and safely restore blood 25-hydroxyvitamin D levels to at least 30 ng/mL and to maintain blood 25-hydroxyvitamin D levels at such optimal levels.

In any of the methods disclosed herein, the agent that increases the risk of hypocalcemia is optionally selected from the group consisting of an antiresorptive agent, an anti-convulsant agent, a corticosteroid, an antihypercalcemia agent, an antimicrobial agent, and combinations thereof. In one aspect, the agent that increases the risk of hypocalcemia is an antiresorptive agent, optionally selected from the group consisting of bisphosphonates (e.g., zoledronic acid, alendronate, risedronate, ibandronate, etidronate, and pamidronate), selective estrogen receptor modulators (e.g., raloxifene), calcitonin, hormones (e.g., estrogen), and monoclonal antibodies (e.g., denosumab). In another aspect, the agent that increases the risk of hypocalcemia is an antihypercalcemia agent, for example, cinacalcet.

In one aspect, a method of treating secondary hyperparathyroidism in Chronic Kidney Disease in a patient on dialysis comprises administering to said patient an effective amount of a 25-hydroxyvitamin D compound by modified release and an effective dose of cinacalcet or a salt thereof in an amount of less than about 360 mg daily, wherein said effective amount of cinacalcet or a salt thereof is a reduced dose compared to the effective dose of cinacalcet or a salt thereof in the absence of said 25-hydroxyvitamin D administration.

In another aspect, a method of treating hypercalcemia in a patient with parathyroid carcinoma comprises administering to said patient an effective amount of a 25-hydroxyvitamin D compound by modified release and an effective dose of cinacalcet or a salt thereof in an amount of less than about 360 mg daily, wherein said effective amount of cinacalcet or a salt thereof is a reduced dose compared to the effective dose of cinacalcet or a salt thereof in the absence of said 25-hydroxyvitamin D administration.

In still another aspect, a method of treating severe hypercalcemia in a patient with primary hyperparathyroidism who is unable to undergo parathyroidectomy comprises administering to said patient an effective amount of a 25-hydroxyvitamin D compound by modified release and an effective dose of cinacalcet or a salt thereof in an amount of less than about 360 mg daily, wherein said effective amount of cinacalcet or a salt thereof is a reduced dose compared to the effective dose of cinacalcet or a salt thereof in the absence of said 25-hydroxyvitamin D administration.

In another aspect, a method of lowering elevated serum parathyroid hormone levels in a patient having a bone metastasis and treated with an antiresorptive agent comprises administering an effective amount of 25-hydroxyvitamin D. In another aspect, a method of stabilizing serum calcium levels in a patient having a bone metastasis and treated with an antiresorptive agent comprises administering an effective amount of 25-hydroxyvitamin D. In still another aspect, a method of treating hungry bone syndrome comprises administering an effective amount of 25-hydroxyvitamin D to a patient in need of thereof.

In any of the methods of the present disclosure, the patient optionally has osteoporosis and/or cancer. In one aspect, a method of managing iatrogenic hypocalcemia and secondary hyperparathyroidism in a patient with a bone metastasis treated with an antiresorptive agent comprises administering an effective amount of 25-hydroxyvitamin D to prevent or reverse the iatrogenic hypocalcemia and lower the patient's serum parathyroid hormone level. In another aspect, a method of mitigating cancer progression and/or a skeletal related event in a patient with a bone tumor, optionally a bone metastasis from a solid tumor, comprises treating the patient with (a) an anticancer agent; (b) an antiresorptive agent; and (c) a 25-hydroxyvitamin D compound, wherein the combination of (a), (b), and (c) is effective to slow tumor growth and/or metastasis and/or increase the time to the first post-treatment skeletal-related event. In still another aspect, a method of treating a patient having cancer and a bone metastasis comprises the administration of (a) a prophylactic and continuing course of an effective amount of 25-hydroxyvitamin D to stabilize 25-hydroxyvitamin D levels and calcium levels in the patient without causing or exacerbating hypercalcemia; followed by (b) treatment with an agent known to increase the risk of iatrogenic hypocalcemia, wherein the treatment in step (a) prevents and/or treats the iatrogenic hypocalcemia in the patient.

In another aspect, a method of mitigating the progression of cancer in the bone in a patient comprises administering an effective amount of 25-hydroxyvitamin D. In another aspect, a method of inhibiting the proliferation and migration of cancer cells comprises administering an effective amount of 25-hydroxyvitamin D to a patient in need thereof. In another aspect, a method of treating cancer in a patient comprises administering to the patient an effective amount of a combination of 25-hydroxyvitamin D and an anticancer agent. In any of the foregoing methods, the patient optionally has a cancer selected from the group consisting of bone cancer, bladder cancer, breast cancer, colon cancer, endometrial cancer, kidney cancer, leukemia, lung cancer, lymphoma, pancreatic cancer, prostate cancer, skin cancer, thyroid cancer, and metastatic forms thereof.

The present disclosure also relates to the use of 25-hydroxyvitamin D, optionally in a modified release formulation, as adjunctive therapy to treat hypocalcemia in a patient in need thereof. In one aspect, the disclosure provides a pharmaceutical composition comprising (a) 25-hydroxyvitamin D and (b) an agent that increases the risk of hypocalcemia and/or an anticancer agent. In one aspect, the disclosure provides a pharmaceutical formulation for oral administration comprising (a) a 25-hydroxyvitamin D compound and (b) an agent that increases the risk of hypocalcemia, optionally cinacalcet or a salt thereof. For example, in one embodiment, the pharmaceutical formulation comprises a first region comprising a 25-hydroxyvitamin D compound and a second region comprising an agent that increases the risk of hypocalcemia, optionally cinacalcet or a salt thereof.

In another aspect, the disclosure provides a kit comprising (a) 25-hydroxyvitamin D; (b) an agent that increases the risk of hypocalcemia and/or an anticancer agent; and (c) instructions for co-administering effective amounts of (a) and (b) to a patient in need thereof.

In another aspect, a method or pharmaceutical formulation according to the present disclosure comprises 25-hydroxyvitamin D in a modified release formulation, optionally an oral modified release formulation. In another aspect, the 25-hydroxyvitamin D is administered in a sterile intravenous formulation. In various aspects, the 25-hydroxyvitamin D can be selected from the group consisting of 25-hydroxyvitamin $D_2$, 25-hydroxyvitamin $D_3$, 25-hydroxyvitamin $D_4$, 25-hydroxyvitamin $D_5$, 25-hydroxyvitamin $D_7$ and combinations thereof. In another aspect, a method or pharmaceutical formulation according to the present disclosure comprises cinacalcet or a salt thereof in an immediate release formulation, optionally an oral rapidly dissolving formulation.

For the compositions and methods described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative and is not intended to limit the invention to the specific embodiments described herein.

DETAILED DESCRIPTION

The present disclosure relates to 25-hydroxyvitamin D therapy as adjunctive therapy and in the treatment of cancer. In various embodiments, the disclosure provides methods for dosing a subject receiving treatment with an agent that increases the risk of hypocalcemia and/or an anticancer agent with an effective amount of 25-hydroxyvitamin D, optionally as a modified release oral formulation or administered in intravenous form. The administration of 25-hydroxyvitamin D to a patient, for example, in a pharmaceutical formulation comprising 25-hydroxyvitamin D and an agent that increases the risk of hypocalcemia, such as cinacalcet or a salt thereof, according to the present disclosure effectively achieves one or more of the following: (a) treats or prevents hypocalcemia, e.g., iatrogenic hypocalcemia; (2) treats or prevents secondary hyperparathyroidism, e.g., in a patient having Chronic Kidney Disease; (3) increases bone mineral density; (4) decreases the blood level of a bone resorption marker; (5) decreases bone pain; (6) increases the time to the first post-treatment skeletal related event; (6) safely restores blood 25-hydroxyvitamin D levels to optimal levels (defined for human subjects as greater than 30 ng/mL) and maintains blood 25-hydroxyvitamin D levels at such optimal levels without causing hypocalcemia or hypercalcemia; (7) lowers elevated serum parathyroid hormone levels; (8) stabilizes serum calcium levels; (9) treats hungry bone syndrome; (10) manages iatrogenic hypocalcemia and secondary hyperparathyroidism in a patient with a bone tumor; (11) mitigates cancer progression, i.e., by inhibiting the proliferation and/or migration of cancer cells; (12) restores or maintains serum calcium levels to at least 8.0 mg/dL, optionally at least 8.3 mg/dL or 8.5 mg/dL, further optionally up to 11.6 mg/dL, e.g. in a range of 8.3 mg/dL and 11.6 mg/dL, corrected for serum albumin; (13) safely increases serum levels of 1,25-dihydroxyvitamin D, optionally to at least 50 pg/mL; (14) achieves or maintains safe serum phosphorus levels and prevents or treats hypophosphatemia; (15) has a positive effect on the serum level of a marker of bone formation; (16) maintains or decreases tumor burden; and/or (17) treats hypercalcemia, e.g., in a patient with parathyroid carcinoma or primary hyperparathyroidism, optionally a patient who is unable to undergo parathyroidectomy.

The present disclosure also relates to the use of 25-hydroxyvitamin D as adjunctive therapy to treat hypocalcemia, and compositions and kits comprising (a) 25-hydroxyvitamin D and (b) an agent that causes hypocalcemia, such as cinacalcet, and/or an anticancer agent.

The methods, compositions, and kits of the present disclosure are contemplated to include embodiments including any combination of one or more of the additional optional elements, features, and steps further described below, unless stated otherwise.

In jurisdictions that forbid the patenting of methods that are practiced on the human body, the meaning of "administering" a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, "administering" compositions includes both methods practiced on the human body and also the foregoing activities.

As used herein, the following definitions may be useful in aiding the skilled practitioner in understanding the invention:

As used herein, the term "comprising" indicates the potential inclusion of other agents, elements, steps, or features, in addition to those specified.

As used herein, the term "25-hydroxyvitamin D" refers to one or more of 25-hydroxyvitamin $D_2$, 25-hydroxyvitamin $D_3$, 25-hydroxyvitamin $D_4$, 25-hydroxyvitamin $D_5$, 25-hydroxyvitamin $D_7$, analogs of the foregoing, and combinations thereof. It is specifically contemplated that in any embodiment described herein, 25-hydroxyvitamin D can include 25-hydroxyvitamin $D_3$, 25-hydroxyvitamin $D_2$, or a combination of 25-hydroxyvitamin $D_3$ and 25-hydroxyvitamin $D_2$. For example, it is specifically contemplated that in any embodiment described herein, 25-hydroxyvitamin D can include 25-hydroxyvitamin $D_3$. Serum total 25-hydroxyvitamin D refers to the total of all such 25-hydroxyvitamin D forms measured by assay, unless a particular 25-hydroxyvitamin D form is referred to.

As used herein, the term "1,25-dihydroxyvitamin D" refers to one or more of 1,25-dihydroxyvitamin $D_2$, 1,25-dihydroxyvitamin $D_3$, 1,25-dihydroxyvitamin $D_4$, 1,25-dihydroxyvitamin $D_5$, 1,25-dihydroxyvitamin $D_7$, analogs of the foregoing, and combinations thereof. For example, 1,25-dihydroxyvitamin D can include 1,25-dihydroxyvitamin $D_2$, 1,25-dihydroxyvitamin $D_3$, or a combination of 1,25-dihydroxyvitamin $D_2$ and 1,25-dihydroxyvitamin $D_3$. Serum total 1,25-dihydroxyvitamin D will be understood to refer to the total of all such 1,25-dihydroxyvitamin D forms by assay, unless a reference is made to a particular 1,25-dihydroxyvitamin D form.

As used herein, the term "cinacalcet" refers to the compound N-[1(R)-(-)-(1-naphthyl)ethyl]-3-[3-(trifluoromethyl)phenyl]-1-aminopropane ($C_{22}H_{22}F_3N$) or a salt thereof, including, but not limited to, a cinacalcet salt comprising any one or more of acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate, for example, cinacalcet HCl. The cinacalcet or salt thereof can be in any form, including, for example, amorphous solids and/or crystalline solids, including polymorphs, pseudopolymorphs, and combinations thereof.

As used herein, the term "adjunctive therapy" refers to administration of 25-hydroxyvitamin D to a patient who is (a) currently receiving; (b) has previously received; or (c) will receive, treatment with a therapeutic agent that is not 25-hydroxyvitamin D. In one aspect, adjunctive therapy refers to the administration of 25-hydroxyvitamin D to a patient before administration with the therapeutic agent that is not 25-hydroxyvitamin D. In another aspect, adjunctive therapy refers to the administration of 25-hydroxyvitamin D to a patient concomitant with administration with the therapeutic agent that is not 25-hydroxyvitamin D. In another aspect, adjunctive therapy refers to the administration of 25-hydroxyvitamin D to a patient after administration with the therapeutic agent that is not 25-hydroxyvitamin D. The therapeutic agent that is not 25-hydroxyvitamin D is optionally an agent that increases the risk of hypocalcemia, such as cinacalcet, or an anticancer agent.

As used herein, the term "antiresorptive agent" refers to a compound that inhibits bone resorption, i.e., a "bone-sparing" agent. Examples of antiresorptive agents include, but are not limited to, bisphosphonates (e.g., zoledronic acid, alendronate, risedronate, ibandronate, etidronate, and pamidronate), selective estrogen receptor modulators (e.g., raloxifene), calcitonin, hormones (e.g., estrogen), and monoclonal antibodies (e.g., denosumab).

As used herein, the terms "co-administer" and "combination therapy" refer to administering an agent that increases the risk of hypocalcemia, such as cinacalcet, or an anticancer agent and 25-hydroxyvitamin D to a subject in a manner that permits the agents to exert their respective pharmacological effects during an overlapping period of time and is a form of adjunctive therapy. The co-administered agent and 25-hydroxyvitamin D can be administered by the same or different routes, and in the same or different compositions. The co-administered agent and 25-hydroxyvitamin D can be administered at the same time, or at different times during a course of treatment (e.g., on alternating days or at different times in the same day). For example, it is contemplated that co-administration can include administration of both an antiresorptive agent or another agent that increases the risk of hypocalcemia, such as cinacalcet, and a 25-hydroxyvitamin D compound within six months or less of each other, or within three months or less of each other, or within one month or less of each other, or within two weeks or less of each other, or within one week or less of each other, or within two days or less of each other, or on the same day. A course of the agent that increases the risk of hypocalcemia or an anticancer agent can include a relatively longer dose interval, e.g., every six months, while 25-hydroxyvitamin D treatment can be on a shorter interval, e.g., daily.

As used herein, the term "substantially constant" with respect to the serum or blood level of 25-hydroxyvitamin D means that the release profile of any formulation administered as detailed herein should not include transient increases in total serum or blood levels of 25-hydroxyvitamin $D_3$ or 25-hydroxyvitamin $D_2$ of greater than approximately 3 ng/mL after administration of a unit dose.

As used herein, the term "modified release" refers to any modification of release from an immediate release profile and can include controlled or sustained release and/or delayed release characteristics. As used herein, the term "controlled release" and "sustained release" are used interchangeably and refer to the release of the administered 25-hydroxyvitamin D from a composition for an extended period of time, e.g., 4 to 24 hours or even longer.

As used herein, the term "rapid release" or "rapidly dissolving" refers to the release of more than 50% of an agent that increases the risk of hypocalcemia from a pharmaceutical formulation within the first 30 minutes after the formulation is administered to a patient.

As used herein, the term "Vitamin D toxicity" refers to the side effects associated with excessive administration of 25-hydroxyvitamin D and excessively elevated 25-hydroxyvitamin D blood levels, including, but not limited to, nausea, vomiting, polyuria, hypercalciuria, hypercalcemia and hyperphosphatemia.

As used herein, the term "hypocalcemia" refers to a condition wherein a patient has a corrected serum levels of calcium below about 8.3 mg/dL or below about 8.5 mg/dL. Severe hypocalcemia refers to a condition wherein the patient has a corrected serum level of calcium below about 7 mg/dL. Normal and safe corrected serum levels of calcium for a human are in a range of about 8.3 to about 11.6 mg/dL. Corrected serum levels of calcium refer to values corrected for serum albumin less than 4.0 g/dL. The term "iatrogenic hypocalcemia" refers to hypocalcemia that occurs following treatment with a therapeutic agent, i.e., an agent that increases the risk of hypocalcemia. Examples of agents that increase the risk of hypocalcemia include, but are not limited to, antiresorptive agents, anticonvulsant agents, corticosteroids, antihypercalcemia agents, antimicrobial agents, and combinations thereof.

As used herein, the term "hypercalcemia" refers to a condition in a patient wherein the patient has corrected serum levels of calcium above about 11.6 mg/dL.

As used herein, the term "hypophosphatemia" refers to a condition wherein a patient has a serum phosphorous level below about 2.5 mg/dL. Normal and safe values for serum phosphorous in a human are in a range of about 2.5 mg/dL to about 4.5 mg/dL.

As used herein, the term "hyperphosphatemia" refers to a condition in a patient wherein the patient has serum phosphorous levels above about 4.5 mg/dL.

As used herein, the term "supraphysiologic" in reference to intralumenal, intracellular and/or blood concentrations of 25-hydroxyvitamin D refers to a combined concentration of 25-hydroxyvitamin D forms during a 24-hour post-dose period which is more than 5 ng/mL greater than the generally stable levels observed over the course of the preceding 24-hour period by laboratory measurement. "Supraphysiologic" in reference to intralumenal, intracellular and/or blood concentrations of 1,25-dihydroxyvitamin D refers to a combined concentration of 1,25-dihydroxyvitamin D forms more than 5 pg/mL greater than the generally stable levels observed over the course of the preceding 24-hour period by laboratory measurement.

As used herein, the term "Vitamin D insufficiency and deficiency" is generally defined in humans as having a serum 25-hydroxyvitamin D level below 30 ng/mL (National Kidney Foundation guidelines, NKF, *Am. J. Kidney Dis.* 42:S1-S202 (2003), incorporated herein by reference).

As used herein, the term "granular form" refers to a mixture of solid particles having a particle size at the 50$^{th}$ percentile of a particle size distribution of the mixture (granule $D_{50}$) in a range from about 50 μm to about 150 μm, for example, about 50 μm, about 60 μm, about 70 μm, about 80 μm, about 90 μm, about 100 μm, about 110 μm, about 120 μm, about 130 μm, about 140 μm, or about 150 μm. The granule $D_{50}$ can be determined using methods known in the art such as sieve analysis, e.g., as described in U.S. Pat. No. 7,829,595.

As used herein, the term "nonpareil" refers to a solid particle having, e.g., a spherical, spheroidal, cubic or cuboidal shape made from a pharmaceutically acceptable material, e.g., sugar and/or starch, having a particle size in a range of 10 μm to 1000 μm.

It is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

In one aspect, the disclosure provides methods of adjunctive therapy using 25-hydroxyvitamin D is patients treated with an agent that increases the risk of hypocalcemia, such as cinacalcet, and/or an anticancer agent. The disclosed methods provide dual unexpected benefits with continued regular administration over a prolonged period of time of unsurpassed effectiveness in restoring blood 25-hydroxyvitamin D to optimal levels and unsurpassed safety relative to currently available formulations of Vitamin D or 25-hydroxyvitamin D. The methods of the present disclosure can include providing a gradual, sustained and direct release of an effective amount of 25-hydroxyvitamin D, preferentially to circulating DBP (rather than to chylomicrons), such that blood, intralumenal and intracellular 25-hydroxyvitamin D concentration spikes, and related unwanted catabolism are mitigated or eliminated. Administration of 25-hydroxyvitamin D according to the present disclosure enhances the intestinal absorption of calcium and reduces PTH-mediated bone resorption. This reduces the likelihood of hypocalcemic events and at the same time, reduces the expression of PTH, thereby mitigating the metastatic impact on resorption of bone. Raising 25-hydroxyvitamin levels in patients as described herein can stabilize serum calcium levels and have an impact on bone microenvironment, cancer progression, and skeletal related events.

Adjunctive therapy comprising 25-hydroxyvitamin D according to the present disclosure improves the efficacy of a co-administered agent that increases the risk of hypocalcemia (e.g., an antiresorptive agent or an antihypercalcemia agent such as cinacalcet) by one or more measures. In one embodiment, co-administering an agent that increases the risk of hypocalcemia and an effective amount of 25-hydroxyvitamin D is effect to treat or prevent iatrogenic hypocalcemia and SHPT. In another embodiment, co-administering an agent that increases the risk of hypocalcemia and an effective amount of 25-hydroxyvitamin D is effective to increase bone mineral density. In another embodiment, co-administering an agent that increases the risk of hypocalcemia and an effective amount of 25-hydroxyvitamin D is effect to decrease bone pain. In another embodiment, co-administering an agent that increases the risk of hypocalcemia and an effective amount of 25-hydroxyvitamin D is effective to treat secondary hyperparathyroidism by lowering elevated plasma PTH levels, optionally by at least 30%. In another embodiment, co-administering an agent that increases the risk of hypocalcemia and an effective amount of 25-hydroxyvitamin D is effective to decrease the incidence or risk of hypocalcemia. In another embodiment, co-administering an agent that increases the risk of hypocalcemia and an effective amount of 25-hydroxyvitamin D is effective to stabilize serum calcium levels, optionally at a level in a range of 8.3 mg/dL and 11.6 mg/dL, corrected for serum albumin. In another embodiment, co-administering an agent that increases the risk of hypocalcemia and an effective amount of 25-hydroxyvitamin D is effective to increase blood levels of a bone formation marker. In another embodiment, co-administering an agent that increases the risk of hypocalcemia and an effective amount of 25-hydroxyvitamin D is effective to decrease blood levels of a bone resorption marker. In another embodiment, co-administering an agent that increases the risk of hypocalcemia and an effective amount of 25-hydroxyvitamin D is effective to delay the time to the first post-treatment SRE. In another embodiment, co-administering an agent that increases the risk of hypocalcemia and an effective amount of 25-hydroxyvitamin D is effective to delay the time to further bone metastasis. In another embodiment, co-administering an agent that increases the risk of hypocalcemia and an effective amount of 25-hydroxyvitamin D is effective to safely increase serum total 25-hydroxyvitamin D levels to at least 30 ng/mL, optionally to supraphysiologic levels. In another embodiment, co-administering an agent that increases the risk of hypocalcemia and an effective amount of 25-hydroxyvitamin D is effective to safely increase serum total 1,25-hydroxyvitamin D levels, optionally to supraphysiologic levels. In another embodiment, co-administering an agent that increases the risk of hypocalcemia and an effective amount of 25-hydroxyvitamin D will be effective to attenuate or halt cancer progression, e.g., by inhibiting the proliferation and migration of cancer cells or maintaining or decreasing tumor burden. In another embodiment, co-administering an agent that increases the risk of hypocalcemia and an effective amount of 25-hydroxyvitamin D will be effective to treat hypercalcemia, e.g., severe hypercalcemia, in a patient with parathyroid carcinoma or primary hyperparathyroidism, optionally a patient who is unable to undergo parathyroidectomy.

In one embodiment, an effective amount of 25-hydroxyvitamin D is administered to a patient that is receiving or has previously received treatment with an agent that increases the risk of hypocalcemia. For example, in one embodiment, 25-hydroxyvitamin D is administered following administration of an agent that increases the risk of hypocalcemia, e.g., an antiresorptive agent or antihypercalcemia agent such as cinacalcet. In another embodiment, 25-hydroxyvitamin D is administered prophylactically to a patient before treatment with an agent that increases the risk of hypocalcemia is undertaken. In still another embodiment, 25-hydroxyvitamin D is co-administered, e.g., in a single composition or separate compositions, with an agent that increases the risk of hypocalcemia. In various embodiments, the agent that increases the risk of hypocalcemia is optionally selected from the group consisting of an antiresorptive agent, an anticonvulsant agent, a corticosteroid, an antihypercalcemia agent, an antimicrobial agent, and combinations thereof. For example, in one embodiment, the agent that increases the risk of hypocalcemia is an antihypercalcemia agent, such as cinacalcet. In another embodiment, the agent that increases the risk of hypocalcemia is an antiresorptive agent, optionally selected from the group consisting of bisphosphonates (e.g., zoledronic acid), RANKL inhibitors (e.g., denosumab), monoclonal antibodies (e.g., denosumab), and combinations thereof.

Another aspect of the present disclosure is treatment of cancer in a patient. Most cancer patients exhibit vitamin D insufficiency (i.e., serum total 25-hydroxyvitamin D less than 30 ng/mL). Although there are a number of possible causes, including diet and reduced exposure to sunlight, recent evidence suggests that accelerated vitamin D catabolism may also be a contributor. Genome amplification at the 20q.13 chromosomal locus that encodes CYP24A1 (Albertson et al. (2000) *Nat Genet* 25, 144-146) has been identified in a number of tumor types (Krishnan et al., supra). Overexpression of CYP24A1 mRNA is reported in a wide variety of human cancers, including breast (Friedrich et al. (2003) *Recent Results Cancer Res* 164, 239-246), lung (Parise et al. (2006) *Int J Cancer* 119, 1819-1828) and colorectal, and in some cases, is linked to a poor prognosis and overall reduced survival (Mimori et al. (2004) *Ann Oncol* 15, 236-241). Overexpression of CYP24A1 increases the growth potential of tumor cells and lowers the responsiveness of tumors to the anti-cancer effects of endogenous calcitriol (Anderson et al. (2006) *Cancer Chemother Pharmacol* 57, 234-240; Friedrich et al., supra). Higher levels of 25-hydroxyvitamin D may therefore be required to achieve vitamin D adequacy for normal cellular and physiological functions and to exert optimal antitumor effects. Administration of 25-hydroxyvitamin D as described herein acts through activation of the Vitamin D receptor pathway to maintain normal calcium homeostasis and can thereby target a variety of tumor types.

Administration of 25-hydroxyvitamin D to a patient having cancer and adjunctive therapy comprising 25-hydroxyvitamin D and an anticancer agent is contemplated to have a therapeutic effect by one or more measures. In one embodiment, administering an effective amount of 25-hydroxyvitamin D, optionally with an anticancer agent and/or agent that increases the risk of hypocalcemia, to the patient is effective to treat cancer, e.g., by inhibiting the proliferation and migration of cancer cells. In another embodiment, administering an effective amount of 25-hydroxyvitamin D, optionally with an anticancer agent and/or agent that increases the risk of hypocalcemia, is effective to maintain or decrease the patient's tumor burden. In another embodiment, administering an effective amount of 25-hydroxyvitamin D, optionally with an anticancer agent and/or agent that increases the risk of hypocalcemia, is effective to mitigate the progression of cancer in the bone. In another embodiment, administering an effective amount of 25-hydroxyvitamin D, optionally with an anticancer agent and/or agent that increases the risk of hypocalcemia, is effective to slow tumor growth and/or metastasis and increase the time to the first-post-treatment SRE in a patient with a bone tumor, optionally a bone metastasis from a solid tumor. In another embodiment, administration of a prophylactic and continuing course of an effective amount of 25-hydroxyvitamin D to the patient to stabilize serum 25-hydroxyvitamin D and calcium levels followed by treatment with an agent known to increase the risk of iatrogenic hypocalcemia is effective to prevent or treat the iatrogenic hypocalcemia.

In any of the methods disclosed herein, administration of 25-hydroxyvitamin D to a patient, e.g., a patient treated with an agent that increases the risk of hypocalcemia or an anticancer agent, as described can be characterized by one or more measures described below, individually or in combination. In one aspect, the amount of 25-hydroxyvitamin D or combination therapy comprising 25-hydroxyvitamin D and an agent that increases the risk of hypocalcemia administered is effective to restore or maintain the patient's corrected serum calcium level to at least about 8.0 mg/dL, optionally in a range of about 8.3 mg/dL to about 11.6 mg/dL. In another aspect, the amount of 25-hydroxyvitamin D or combination therapy comprising 25-hydroxyvitamin D and an agent that increases the risk of hypocalcemia administered can be effective to restore or maintain the patient's corrected serum calcium level to at least about 8.3 mg/dL, 8.5 mg/dL, at least about 9.0 mg/dL, at least about 9.5 mg/dL, at least about 10 mg/dL, at least about 10.5 mg/dL, or at least about 11.0 mg/dL, optionally in a range of about 8.5 mg/dL to about 11.0 mg/dL, about 8.3 mg/dL to about 10.2 mg/dL, about 8.3 mg/dL to about 11.0 mg/dL, or about 8.5 mg/dL to about 10.2 mg/dL, for example.

In another aspect, the amount of 25-hydroxyvitamin D or combination therapy comprising 25-hydroxyvitamin D and an agent that increases the risk of hypocalcemia administered can be effective to safely increase the patient's serum level of 25-hydroxyvitamin D to at least about 30 ng/mL, optionally in a range of about 30 ng/mL to about 100 ng/mL, about 35 ng/mL to about 90 ng/mL, about 40 ng/mL to about 100 ng/mL, or about 50 ng/mL to about 100 ng/mL. In another aspect, the amount of 25-hydroxyvitamin D or combination therapy comprising 25-hydroxyvitamin D and an agent that increases the risk of hypocalcemia administered can be effective to safely increase the patient's serum level of 25-hydroxyvitamin D to at least about 35 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least about 150 ng/mL, at least about 200 ng/mL, at least about 250 ng/mL, or at least about 300 ng/mL.

In another aspect, the amount of 25-hydroxyvitamin D or combination therapy comprising 25-hydroxyvitamin D and an agent that increases the risk of hypocalcemia administered can be effective to decrease the patient's serum parathyroid hormone level, optionally by at least about 10%, at least about 20%, at least about 30%, at least about 40%, or at least about 50%. In another aspect, the amount of 25-hydroxyvitamin D or combination therapy comprising 25-hydroxyvitamin D and an agent that increases the risk of hypocalcemia administered can be effective to decrease the patient's serum parathyroid hormone related peptide (PTHrP) level, optionally by at least about 10%, at least about 20%, at least about 30%, at least about 40%, or at least about 50%.

In another aspect, the amount of 25-hydroxyvitamin D or combination therapy comprising 25-hydroxyvitamin D and an agent that increases the risk of hypocalcemia administered can be effective to safely increase the patient's serum level of 1,25-dihydroxyvitamin D, optionally to at least about 50 pg/mL, at least about 60 pg/mL, at least about 70 pg/mL, at least about 80 pg/mL, at least about 90 pg/mL, or at least about 100 pg/mL.

In another aspect, the amount of 25-hydroxyvitamin D or combination therapy comprising 25-hydroxyvitamin D and an agent that increases the risk of hypocalcemia administered can be effective to achieve or maintain safe serum phosphorous levels, and prevent hypophosphatemia. In another aspect, the amount of 25-hydroxyvitamin D or combination therapy comprising 25-hydroxyvitamin D and an agent that increases the risk of hypocalcemia administered can be effective to achieve or maintain serum phosphorus levels above about 2.5 mg/dL, above about 3.0 mg/dL, above about 3.5 mg/dL, above about 4.0 mg/dL, or above about 4.5 mg/dL, optionally in a range between about 2.5 mg/dL and about 4.5 mg/dL.

In another aspect, the amount of 25-hydroxyvitamin D or combination therapy comprising 25-hydroxyvitamin D and an agent that increases the risk of hypocalcemia administered can be effective to have a positive effect on the patient's serum level of a marker of bone formation compared to no treatment or treatment with an antiresorptive agent alone. For example, the amount of 25-hydroxyvitamin D or combination therapy comprising 25-hydroxyvitamin D and an agent that increases the risk of hypocalcemia administered can be effective to increase the patient's serum level of a marker of bone formation, e.g., bone morphogenetic protein or osteocalcin, by at least about 10%, at least about 20%, at least about 30%, at least about 40%, or at least about 50%, compared to no treatment or treatment with an antiresorptive agent alone. In another aspect, the amount of 25-hydroxyvitamin D or combination therapy comprising 25-hydroxyvitamin D and an agent that increases the risk of hypocalcemia administered can be effective to decrease the patient's serum level of a marker of bone resorption, optionally by at least 10%, at least 20%, at least about 30%, at least about 40%, or at least about 50%, compared to no treatment levels or treatment with an antiresorptive agent alone. In another aspect, the amount of 25-hydroxyvitamin D or combination therapy comprising 25-hydroxyvitamin D and an agent that increases the risk of hypocalcemia administered can effective to mitigate the increase in the patient's serum level of a marker of bone resorption compared to no treatment or treatment with an antiresorptive agent alone. In various embodiments, the marker of bone resorption is selected from the group consisting of PTHrP, FGF23, NTX, CTX, TRAC-5b, and combinations thereof.

In another aspect, the amount of 25-hydroxyvitamin D or combination therapy comprising 25-hydroxyvitamin D and an agent that increases the risk of hypocalcemia administered can be effective to decrease or increase the patient's serum level of an immune meditating cytokine, e.g. C-reactive protein (CRP), interleukin 12, or interleukin 10, optionally by at least about 10%, at least about 20%, at least about 30%, at least 40%, or at least about 50%. In another aspect, the amount of 25-hydroxyvitamin D can be effective to increase the spot calcium/creatinine (Ca/Cr) ratio.

In another aspect, the amount of 25-hydroxyvitamin D or combination therapy comprising 25-hydroxyvitamin D and an agent that increases the risk of hypocalcemia administered can be effective to maintain or decrease the patient's tumor burden. Tumor burden may be measured using assays known in the art, e.g., radiography, computed tomography (CT), or magnetic resonance imaging (MRI). Tumor burden may also be assessed by measuring one or more markers of tumor burden. In another aspect, the amount of 25-hydroxyvitamin D or combination therapy comprising 25-hydroxyvitamin D and an agent that increases the risk of hypocalcemia administered can be effective to decrease the patient's serum level of a marker of tumor burden, optionally by at least about 10%, at least about 20%, at least about 30%, at least about 40%, or at least about 50%, compared to no treatment or treatment with an anticancer agent and/or an agent that increases the risk of hypocalcemia alone. In another aspect, the amount of 25-hydroxyvitamin D or combination therapy comprising 25-hydroxyvitamin D and an agent that increases the risk of hypocalcemia administered can be effective to mitigate the increase in the patient's tumor burden or serum level of a marker of tumor burden, compared to no treatment or treatment with an anticancer agent and/or agent that increases the risk of hypocalcemia only. In embodiments, the marker of tumor burden can be optionally selected from the group consisting of CEA, CA 125, CA15-3, CA 27-29, prostate specific antigen (PSA), and combinations thereof.

In one aspect, combination therapy comprising an effective amount of 25-hydroxyvitamin D and an effective amount of an agent that increases the risk of hypocalcemia such as cinacalcet can be effective to treat secondary hyperparathyroidism in Chronic Kidney Disease, optionally in a patient on dialysis, wherein said effective amount of the agent that increases the risk of hypocalcemia is a reduced dose compared to the effective dose of the agent that increases the risk of hypocalcemia in the absence of said 25-hydroxyvitamin D administration. In another aspect, combination therapy comprising an effective amount of 25-hydroxyvitamin D and an effective amount of an agent that increases the risk of hypocalcemia such as cinacalcet can be effective to treat hypercalcemia, e.g., in a patient having parathyroid carcinoma or primary hyperparathyroidism, wherein said effective amount of the agent that increases the risk of hypocalcemia is a reduced dose compared to the effective dose of the agent that increases the risk of hypocalcemia in the absence of said 25-hydroxyvitamin D administration. For example, the effective amount of the agent that increases the risk of hypocalcemia co-administered with 25-hydroxyvitamin D can be about 5% less, about 10% less, about 15% less, about 20% less, about 25% less, about 30% less, about 35% less, about 40% less, about 45% less, or about 50% less, than the effective dose of the agent that increases the risk of hypocalcemia in the absence of said 25-hydroxyvitamin D co-administration. For example, in one embodiment, the effective amount of the agent that increases the risk of hypocalcemia co-administered with 25-hydroxyvitamin D is cinacalcet or a salt thereof in an amount of less than 360 mg daily, for example in a range of 30 mg to 90 mg, 30 mg to 60 mg, 20 mg to 60 mg, or 20 mg to 25 mg, administered once, twice, three, or four times daily.

In one class of embodiments, the effective amount of 25-hydroxyvitamin D is co-administered with an agent that increases the risk of hypocalcemia and/or an anticancer agent. In one embodiment, 25-hydroxyvitamin D is co-administered with cinacalcet or a salt thereof, optionally in a single formulation, e.g., a capsule comprising both agents.

The present disclosure also provides a kit comprising (a) 25-hydroxyvitamin D, (b) an agent that increases the risk of hypocalcemia and/or an anticancer agent, and (c) instructions for co-administering effective amounts of (a) and (b) to a patient in need thereof. The indications and usage of the agent(s) co-administered with 25-hydroxyvitamin D according to the present methods are not particularly limited, and can be equivalent to those already taught in the literature.

The methods of the present disclosure are suitable for treating patients having a condition responsive to administration of 25-hydroxyvitamin D as described. In one type of embodiment, the patient has osteoporosis. In another type of embodiment, the patient has hungry bone syndrome. In another type of embodiment, the patient has impaired renal function, e.g., a patient having Chronic Kidney Disease (CKD) Stage 1, 2, 3, 4, or 5. In one embodiment, the patient is receiving dialysis. In another embodiment, the patient has CKD, but is not on dialysis.

In another type of embodiment, the patient has cancer, optionally a cancer selected from the group consisting of bone cancer, bladder cancer, breast cancer, colon cancer, endometrial cancer, kidney cancer, leukemia, lung cancer, lymphoma, pancreatic cancer, parathyroid cancer, prostate cancer, skin cancer, thyroid cancer, and metastatic forms thereof. In one embodiment, the patient has cancer and a bone tumor, i.e., a bone metastasis from a solid tumor. For example, the patient may have metastatic bone cancer, metastatic prostate cancer, metastatic lung cancer, and/or metastatic breast cancer.

Optionally, the patient has cancer and is receiving, has previously received, or will receive, treatment with an anticancer agent. Exemplary classes of anticancer agents include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; a mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a Flt-3 inhibitor; an Hsp90 inhibitor; a kinesin spindle protein inhibitor; a MEK inhibitor; an antitumor antibiotic; a nitrosourea, a compound targeting/decreasing protein or lipid kinase activity, a compound targeting/decreasing protein or lipid phosphatase activity, an antiangiogenic compound, and combinations thereof. In various types of embodiments, the patient can be treated with an anticancer agent selected from the group consisting of azacitidine, axathioprine, bevacizumab, bleomycin, capecitabine, carboplatin, chlorabucil, cisplatin, cyclophosphamide, cytarabine, daunorubicin, docetaxel, doxifluridine, doxorubicin, epirubicin, etoposide, fluorouracil, gemcitabine, herceptin, idarubicin, mechlorethamine, melphalan, mercaptopurine, methotrexate, mitoxantrone, oxaliplatin, paclitaxel, tafluposide, teniposide, tioguanine, retinoic acid, valrubicin, vinblastine, vincristine, vindesine, vinorelbine, receptor tyrosine kinase inhibitors, and combinations thereof.

Optionally, the patient having a condition described above to be treated with 25-hydroxyvitamin D is receiving, has previously received, or will receive, treatment with an agent that increases the risk of hypocalcemia, optionally an agent selected from the group consisting of an antiresorptive agent, an anticonvulsant agent, a corticosteroid, an antihypercalcemia agent, an antimicrobial agent, and combinations thereof. In one type of embodiment, the agent that increases the risk of hypocalcemia is an antihypercalcemia agent, optionally the antihypercalcemia agent cinacalcet. In another type of embodiment, the agent that increases the risk of hypocalcemia is an antiresorptive agent, optionally selected from the group consisting of bisphosphonates, selective estrogen receptor modulators, calcitonin, hormones, and monoclonal antibodies. In one type of embodiment, the antiresorptive agent comprises a RANKL inhibitor, optionally the RANKL inhibitor denosumab. In another type of embodiment, the antiresorptive agent comprises a bisphosphonate, optionally the bisphosphonate zoledronic acid. Optionally, a patient having cancer is receiving, has previously received, or will receive, treatment with an agent that increases the risk of hypocalcemia and an anticancer agent.

For each of the foregoing measures, it is contemplated that adjunctive therapy with 25-hydroxyvitamin D will achieve such increases, decreases, and/or delays to a greater degree compared to administering the agent that increases the risk of hypocalcemia, e.g., cinacalcet, and/or anticancer agent alone. In another aspect, it is contemplated that the adjunctive therapy with 25-hydroxyvitamin D will achieve such increases, decreases, and/or delays to a greater degree compared to co-administering the agent that increases the risk of hypocalcemia with cholecalciferol, optionally with an anticancer agent. It is contemplated that the adjunctive therapy with 25-hydroxyvitamin D will achieve such increases, decreases, and/or delays to a greater degree compared to co-administering the agent that increases the risk of hypocalcemia with ergocalciferol, optionally with an anticancer agent. It is also contemplated that adjunctive therapy with 25-hydroxyvitamin D will mitigate, i.e., lessen the severity of, undesirable effect compared to administering the agent that increases the risk of hypocalcemia and/or anticancer agent alone or the antiresorptive agent with cholecalciferol or ergocalciferol, optionally with an anticancer agent. Examples of undesired effects include, but are not limited to, an increase or decrease of serum calcium or phosphorous to a level outside the normal range, a decrease in blood levels of a bone formation marker, an increase in blood levels of a bone resorption marker, and an increase in tumor burden (e.g., an increase in a marker of tumor progression).

The present disclosure also contemplates compositions comprising oral or intravenous formulations of 25-hydroxyvitamin D and related methods of administration. Such compositions and related methods of administration can be selected to have one or more features including increasing blood levels of 25-hydroxyvitamin D without the potential first-pass effects of 25-hydroxyvitamin D prohormones in the duodenum; without supraphysiological surges in intralumenal, intracellular and blood levels of 25-hydroxyvitamin D and their consequences; without causing substantially increased catabolism of the administered 25-hydroxyvitamin D; and without causing serious side effects associated with Vitamin D supplementation, namely Vitamin D toxicity.

In one type of embodiment, modified release compositions intended for oral administration in accordance with the present invention are designed to contain a dosage of 25-hydroxyvitamin D (e.g. 25-hydroxyvitamin $D_3$, or a combination of 25-hydroxyvitamin $D_2$ and 25-hydroxyvitamin $D_3$) of 1 to 1000 mcg per unit dose, or 1 to 500 mcg per unit dose or 1 to 100 mcg per dose, or 1 to 50 mcg per dose, or 10 to 40 mcg per dose, for example, 30 mcg, 60 mcg, 90 mcg, 100 mcg, 200 mcg, 300 mcg, 400 mcg, 500 mcg, 600 mcg, 700 mcg, 800 mcg, 900 mcg, or 1000 mcg 25-hydroxyvitamin D per unit dose, and are prepared in such a manner as to effect controlled or substantially constant release of the 25-hydroxyvitamin D into the gastrointestinal tract of a subject over an extended period of time. In one embodiment, the 25-hydroxyvitamin D is 25-hydroxyvitamin $D_3$. In another embodiment, the 25-hydroxyvitamin D is a combination of 25-hydroxyvitamin $D_3$ and 25-hydroxy vitamin $D_2$ and are useful in supporting both the Vitamin $D_3$ and Vitamin $D_2$ endocrine systems. Currently available oral Vitamin D supplements and the previously marketed oral formulation of 25-hydroxyvitamin $D_3$ have supported just one or the other system. In one type of embodiment, the release can be in the ileum or later, for example in the colon. In another type of embodiment, the composition can result in a substantially increased absorption of 25-hydroxyvitamin D via transport on DBP and decreased absorption via transport in chylomicrons. In another type of embodiment, the composition can result in maintenance of substantially constant blood levels of 25-hydroxyvitamin D during the 24-hour post-dosing period. Examples of modified release compositions of 25-hydroxyvitamin D are described in U.S. Pat. Nos. 8,207,149, 8,361,488, and 8,426,391, and U.S. patent application Ser. No. 14/213,285, incorporated herein by reference.

In one aspect, a composition of the present disclosure comprising 25-hydroxyvitamin D further comprises an agent that increases the risk of hypocalcemia. In one embodiment, a pharmaceutical formulation for oral administration of the present disclosure comprises (a) a 25-hydroxyvitamin D compound (e.g., 25-hydroxyvitamin $D_3$ and/or 25-hydroxyvitamin $D_2$) and (b) and agent that increases the risk of hypocalcemia (e.g., cinacalcet or cinacalcet HCl). In one embodiment, the pharmaceutical formulation comprises (a) and (b) in a single capsule, e.g., a hard shell or soft capsule, optionally a multi-layered or multi-chambered capsule. For example, in one embodiment, a pharmaceutical formulation of the present disclosure comprises a first region comprising the 25-hydroxyvitamin D compound and a second region comprising the agent that increases the risk of hypocalcemia, for example, in a multi-layered composition having a 25-hydroxyvitamin D core and an outer layer or surface coating comprising the agent that increases the risk of hypocalcemia or comprising the agent that increases the risk of hypocalcemia disposed in a first capsule shell and the 25-hydroxyvitamin D compound disposed in second capsule shell, the second capsule shell being disposed within the first capsule shell. In another embodiment, the pharmaceutical formulation comprises a multi-chambered composition comprising adjacent first and second, e.g., tandem, regions/chambers. In other embodiments, a pharmaceutical formulation comprises particles comprising the agent that increases the risk of hypocalcemia, e.g., cinacalcet, in granular form, for example, as described in U.S. Pat. No. 7,829,595, incorporated herein by reference, or nonpareils coated with the agent that increases the risk of hypocalcemia. The particles comprising the agent that increases the risk of hypocalcemia can be in a second region separate from a first region comprising 25-hydroxyvitamin D, or dispersed within a non-aqueous solution comprising 25-hydroxyvitamin D disposed within a capsule. In various embodiments, a composition of the present disclosure comprises 25-hydroxyvitamin D in an amount between 1 mcg to 1000 mcg per unit dose, or 1 mcg to 500 mcg per unit dose, or 1 mcg to 100 mcg per dose, or 1 mcg to 50 mcg per dose, or 10 mcg to 40 mcg per dose, or 100 mcg to 300 mcg, for example, 30 mcg, 60 mcg, 90 mcg, 100 mcg, 200 mcg, 300 mcg, 400 mcg, 500 mcg, 600 mcg, 700 mcg, 800 mcg, 900 mcg, or 1000 mcg 25-hydroxyvitamin D per unit dose and cinacalcet in an amount between 1 mg to 500 mg per unit dose, or 1 mg to 100 mg per unit dose, or 100 mg to 400 mg per dose, or 1 mg to 50 mg per dose, or 10 mg to 40 mg per dose, for example, 10 mg, 15 mg, 20 mg, 25 mg, 30 mg, 60 mg, 90 mg, 100 mg, 150 mg, 200 mg, 250 mg, 300 mg, 350 mg, 400 mg, 450 mg, or 500 mg cinacalcet per unit dose. In any of the embodiments of the present disclosure, a pharmaceutical formulation optionally comprises (a) 25-hydroxyvitamin D and (b) an agent that increases the risk of hypocalcemia in an amount that is bioequivalent to a dosage described herein.

A pharmaceutical formulation of the present disclosure optionally comprises 25-hydroxyvitamin D in a modified release formulation as described herein and/or an agent that increases the risk of hypocalcemia, e.g. cinacalcet, in an immediate release formulation. For example, in one embodiment, the composition comprises a modified release composition of 25-hydroxyvitamin D as described herein or in U.S. Pat. Nos. 8,207,149, 8,361,488, and 8,426,391, and U.S. patent application Ser. No. 14/213,285, incorporated herein by reference, and/or cinacalcet in an immediate release formulation such as a rapidly dissolving formulation as described in U.S. Pat. No. 7,829,595, incorporated herein by reference. In one embodiment, a pharmaceutical formulation comprises a core region comprising 25-hydroxyvitamin D in a modified release formulation, and an outer layer, e.g., a surface coating, comprising cinacalcet in an immediate release formulation such as a rapidly dissolving formulation. In another embodiment, a pharmaceutical formulation comprises a first region comprising 25-hydroxyvitamin D in a modified release formulation and particles comprising cinacalcet dispersed within the first region or within a second region. In one type of embodiment, the co-formulated dosage form with 25-hydroxyvitamin D and cinacalcet HCl will deliver an amount of cinacalcet HCl that is bioequivalent to SENSIPAR, on a mg-per-mg basis.

In various embodiments, a pharmaceutical formulation of the present disclosure comprises a region (e.g., a layer, a chamber, a granule, or a coating on a capsule or nonpareil) comprising cinacalcet in an immediate release formulation further comprising one or more of a diluent, a binder, a disintegrant, and combinations thereof. Examples of pharmaceutically acceptable diluents include, but are not limited to, starch, microcrystalline cellulose, dicalcium phosphate, lactose, sorbitol, mannitol, sucrose, methyl dextrins, and combinations thereof. Examples of binders include, but are not limited to, povidone, hydroxypropyl methylcellulose, dihydroxy propylcellulose, sodium carboxylmethylcellulose, gelatin, acacia, tragacanth, alginic acid, cellulose, methyl cellulose, ethyl cellulose, hydroxypropyl cellulose, polyethylene glycol, polyvinyl alcohol, polymethacrylate, polyvinylcaprolactam, and combinations thereof. Examples of disintegrants include, but are not limited to, crospovidone, sodium starch glycolate, croscarmellose sodium, croscarmellose, sodium starch glycolate, cross linked cellulose, cross linked polymers, cross linked starches, and combinations thereof.

In one embodiment, a pharmaceutical formulation comprises a region comprising cinacalcet or a salt thereof in an immediate release formulation comprising from about 10% to about 40% by weight of cinacalcet or a salt thereof, from about 45% to about 85% by weight of at least one diluent, and from about 1% to about 10% by weight of at least one disintegrant, optionally further comprising from about 1% to about 5% by weight of at least one binder, wherein the percentage by weight is relative to the total weight of the region.

For example, in one embodiment, a composition according to the present disclosure comprises a region comprising cinacalcet or a salt thereof in an immediate release formulation comprising from about 10% to about 40% by weight of cinacalcet or a salt thereof, from about 40% to about 75% by weight of microcrystalline cellulose, from about 1% to about 5% by weight povidone, from about 5% to about 10% by weight of starch, and from about 1% to about 10% by weight of crosprovidone, optionally further comprising from about 0.05% to about 1.5% by weight of colloidal silicon dioxide and from about 0.05% to about 1.5% by weight of magnesium stearate, wherein the percentage by weight is relative to the total weight of the region.

In another embodiment, a composition according to the present disclosure comprises a region comprising cinacalcet or a salt thereof in an immediate release formulation comprising from about 10% to about 40% by weight of cinacalcet or a salt thereof, from about 40% to about 75% by weight of microcrystalline cellulose, from about 1% to about 5% by weight povidone, and from about 5% to about 35% by weight of starch, optionally further comprising from about 0.05% to about 1.5% by weight of colloidal silicon dioxide and from about 0.05% to about 1.5% by weight of magnesium stearate, wherein the percentage by weight is relative to the total weight of the region.

In another embodiment, a composition according to the present disclosure comprises a region comprising cinacalcet or a salt thereof in an immediate release formulation comprising from about 10% to about 40% by weight of cinacalcet or a salt thereof, from about 40% to about 75% by weight of microcrystalline cellulose, from about 15% to about 50% by weight of starch, and from about 1% to about 10% by weight of a disintegrant selected from croscarmellose, sodium starch glycolate, cross linked cellulose, cross linked polymers, cross linked starches, and combinations thereof, optionally further comprising from about 0.05% to about 1.5% by weight of colloidal silicon dioxide and from about 0.05% to about 1.5% by weight of magnesium stearate, wherein the percentage by weight is relative to the total weight of the region.

In another embodiment, a composition according to the present disclosure comprises a region comprising cinacalcet or a salt thereof in an immediate release formulation comprising from about 10% to about 40% by weight of cinacalcet or a salt thereof, from about 40% to about 75% by weight of microcrystalline cellulose, from about 1% to about 5% by weight of povidone, and from about 1% to about 10% by weight of a disintegrant selected from croscarmellose, sodium starch glycolate, cross linked cellulose, cross linked polymers, cross linked starches, and combinations thereof, optionally further comprising from about 0.05% to about 1.5% by weight of colloidal silicon dioxide and from about 0.05% to about 1.5% by weight of magnesium stearate, wherein the percentage by weight is relative to the total weight of the region.

In another embodiment, a composition according to the present disclosure comprises a region comprising cinacalcet or a salt thereof in an immediate release formulation comprising from about 10% to about 40% by weight of cinacalcet or a salt thereof, from about 40% to about 75% by weight of microcrystalline cellulose, from about 1% to about 5% by weight of a binder selected from the group consisting of gelatin, acacia, tragacanth, alginic acid, cellulose, methyl cellulose, ethyl cellulose, HPMC, HPC, sodium carboxy methyl cellulose, PEG, PVA, polymethacrylate, polyvinylcaprolactam, and combinations thereof, from about 5% to about 35% by weight of starch, and from about 1% to about 10% by weight of crospovidone, optionally further comprising from about 0.05% to about 1.5% by weight of colloidal silicon dioxide and from about 0.05% to about 1.5% by weight of magnesium stearate, wherein the percentage by weight is relative to the total weight of the region.

In one embodiment, the pharmaceutical formulation can be characterized by dissolution release profile providing a release of 25-hydroxyvitamin D of less than 30% at 2 hours, greater than 45% at 6 hours, and greater than 80% at 12 hours, and further optionally less than 60% at 6 hours. In another type of embodiment, the formulation can be characterized by an in vitro dissolution profile providing release of 25-hydroxyvitamin D of less than 30% at 100 to 140 minutes, greater than 45% at 5 to 7 hours, and greater than 80% at 11 to 13 hours. In another embodiment, the composition can be characterized by an in vitro dissolution profile providing release of 25-hydroxyvitamin D of less than 30% at 2 hours, greater than 45% at 6 hours, and greater than 80% at 12 hours. In these types of embodiments, optionally the release of vitamin D compound at 5 to 7 hours is less than 60%, or at 6 hours is less than 60%.

In another type of embodiment, the composition can be characterized by an in vitro dissolution profile providing release of 25-hydroxyvitamin D of about 20% to about 40% at 2 hours, at least 35% at 6 hours, and at least 70% at 12 hours. In another embodiment, the formulation can be characterized by an in vitro dissolution profile providing release of 25-hydroxyvitamin D compound of about 25% to about 35% at 2 hours, at least 40% at 6 hours, and at least 75% at 12 hours. In these embodiments, optionally the release of 25-hydroxyvitamin D is 75% or less at 6 hours, or 65% or less at 6 hours, or 60% or less at 6 hours, for example.

In any of the embodiments described herein, the composition can be characterized by an in vitro dissolution profile providing release of cinacalcet of about 50% to about 100% at 30 minutes or less. Optionally, the release of cinacalcet is at least 80% at 15 minutes, at least 90% at 30 minutes, at least 97% at 45 minutes, or at least 98% at 60 minutes. For example, in some embodiments, the release of cinacalcet is at least 85%, at least 90%, at least 95%, or at least 98% at 15 minutes.

The release of 25-hydroxyvitamin D or cinacalcet can be measured using a suitable in vitro dissolution method, such as one of the methods already known in the art. Any of the dissolution studies described in the United States Pharmacopeia, USP 29-NF 24, Dissolution <711> physical tests and determinations, United States Pharmacopeial Convention, Inc., Rockville, Md., 2006, pp. 2673-2682.; European Pharmacopoeia 2.9.3 Dissolution Test for Solid Dosage Forms, or the Japanese Pharmacopoeia 6.10 Dissolution Test, can be used to determine the in vitro dissolution profile in accordance with the present disclosure.

In one type of embodiment, the 25-hydroxyvitamin D is administered orally. For example, the 25-hydroxyvitamin D can be administered in an oral modified release formulation. In the alternative, the 25-hydroxyvitamin D can be administered in an oral immediate release formulation in multiple daily doses in order to produce a pharmacokinetic profile of serum 25-hydroxyvitamin D that is similar to that achieved by an oral modified or sustained release formulation.

The preparation of a modified release form of 25-hydroxyvitamin D suitable for oral administration can be carried out according to many different techniques. For example, one or more 25-hydroxyvitamin D compounds can be dispersed within a matrix, i.e., a unique mixture of rate controlling constituents and excipients in carefully selected ratios within the matrix, and optionally encased with a coating material. In another alternative, various coating techniques can be utilized to control the rate and/or the site of the release of the 25-hydroxyvitamin D from the pharmaceutical formulation. For example, the dissolution of the coating may be triggered by the pH of the surrounding media, and the resulting gradual dissolution of the coating over time exposes the matrix to the fluid of the local environment. In one type of embodiment, after the coating becomes permeable, 25-hydroxyvitamin D diffuses from the outer surface of the matrix. When this surface becomes exhausted or depleted of 25-hydroxyvitamin D, the underlying stores begin to be depleted by diffusion through the disintegrating matrix to the external solution. In another type of embodiment, release of 25-hydroxyvitamin D is by gradual disintegration or erosion of the matrix, e.g., via solubility of one or more components of the matrix and/or by lack of physical integrity.

In one aspect, a formulation in accordance with the present invention provides one or more 25-hydroxyvitamin D compounds within a matrix that releasably binds the ingredients for sustained release, e.g., when exposed to the contents of the ileum and/or colon.

Optionally, the 25-hydroxyvitamin D-containing matrix can be suitably covered with a coating that is resistant to disintegration in gastric juices. The coated modified release formulation of 25-hydroxyvitamin D is then administered orally to subjects, e.g., animals or human patients. As the formulation travels through the proximal portion of the small intestine, the enteric coating becomes progressively more permeable but, in a suitable embodiment, it provides a persisting structural framework around the 25-hydroxyvitamin D-containing matrix. The 25-hydroxyvitamin D-containing matrix becomes significantly exposed to intestinal fluids in the ileum through the permeable overcoating, and the 25-hydroxyvitamin D is then gradually released by simple diffusion and/or slow disintegration of the matrix.

Once released into the lumen of the ileum, the 25-hydroxyvitamin D is absorbed into the lymphatic system or into the portal bloodstream, where it is bound to and transported by the DBP. In this embodiment, the 25-hydroxyvitamin D is primarily absorbed at a point beyond the duodenum and jejunum. These proximal portions of the small intestine can respond to high intralumenal levels of 25-hydroxyvitamin D and in the process, can catabolize significant quantities of the 25-hydroxyvitamin D. By substantially delaying 25-hydroxyvitamin D release until the ileum and/or colon, the pharmaceutical composition described herein virtually eliminates these potential first-pass effects in the proximal intestine and reduces unwanted catabolism. Significant catabolism of administered 25-hydroxyvitamin D prior to absorption into the bloodstream significantly lowers its bioavailability. Elimination of first-pass effects reduces the risk of Vitamin D toxicity. Substantially delayed release of 25-hydroxyvitamin D (i.e., beyond the duodenum and jejunum) markedly decreases the amount of 25-hydroxyvitamin D that is incorporated and absorbed from the small intestine via chylomicrons (since chylomicron formation and absorption occurs primarily in the jejunum) and correspondingly increases the amount of 25-hydroxyvitamin D that is absorbed directly through the intestinal wall and onto DBP circulating in lymph or portal blood.

In one embodiment of the invention, a controlled release oral formulation of 25-hydroxyvitamin D is prepared generally according to the following procedure. A sufficient quantity of 25-hydroxyvitamin D is completely dissolved in a minimal volume of USP-grade absolute ethanol (or other suitable solvent) and mixed with appropriate amounts and types of pharmaceutical-grade excipients to form a matrix which is solid or semi-solid at both room temperature and at the normal temperature of the human body. The matrix is completely or almost entirely resistant to digestion in the stomach and upper small intestine, and it gradually disintegrates in the lower small intestine and/or colon.

In a suitable formulation, the matrix binds the 25-hydroxyvitamin D compound(s) and permits a slow, relatively steady, e.g. substantially constant, release of 25-hydroxyvitamin D over a period of four to eight hours or more, by simple diffusion and/or gradual disintegration, into the contents of the lumen of the lower small intestine and/or colon. The formulation optionally further has an enteric coating that partially dissolves in aqueous solutions having a pH of about 7.0 to 8.0, or simply dissolves slowly enough that significant release of 25-hydroxyvitamin D is delayed until after the formulation passes through the duodenum and jejunum.

As discussed above, the means for providing the controlled release of 25-hydroxyvitamin D may be selected from any suitable controlled release delivery system, including any of the known controlled release delivery systems of an active ingredient over a course of about four or more hours, including the wax matrix system, and the EUDRAGIT RS/RL system (Rohm Pharma, GmbH, Weiterstadt, Germany).

The wax matrix system provides a lipophilic matrix. The wax matrix system may utilize, for example, beeswax, white wax, cachalot wax or similar compositions. The active ingredient(s) are dispersed in the wax binder which slowly disintegrates in intestinal fluids to gradually release the active ingredient(s). The wax binder that is impregnated with 25-hydroxyvitamin D can be loaded into softgel capsules. A softgel capsule may comprise one or more gel-forming agents, e.g., gelatin, starch, carrageenan, and/or other pharmaceutically acceptable polymers. In one embodiment, partially crosslinked soft gelatin capsules are used. As another option, vegetable-based capsules can be used. The wax matrix system disperses the active ingredient(s) in a wax binder which softens at body temperature and slowly disintegrates in intestinal fluids to gradually release the active ingredient(s). The system suitably can include a mixture of waxes, with the optional addition of oils, to achieve a melting point which is higher than body temperature, but lower than the melting temperature of the selected formulations used to create the shell of a soft or hard capsule, or vegetable capsule shell, or other formulation used to create a shell casing or other coating.

Specifically, in one suitable embodiment, the waxes selected for the matrix are melted and thoroughly mixed. The desired quantity of oils is subsequently added, followed by sufficient mixing for homogenization. The waxy mixture is then gradually cooled to a temperature just above its melting point. The desired amount of 25-hydroxyvitamin D, dissolved in ethanol, is uniformly distributed into the molten matrix, and the matrix is loaded into capsules, for example vegetable-based or gelatin-based capsules. The filled capsules optionally are treated for appropriate periods of time with a solution containing an aldehyde, such as acetaldehyde, to partially crosslink a polymer, e.g., gelatin, in the capsule shell, when used. The capsule shell becomes increasingly crosslinked, over a period of several weeks and, thereby, more resistant to dissolution in the contents of stomach and upper intestine. When properly constructed, this gelatin shell will gradually dissolve after oral administration and become sufficiently porous (without fully disintegrating) by the time it reaches the ileum to allow the 25-hydroxyvitamin D to diffuse slowly from the wax matrix into the contents of the lower small intestine and/or colon.

Examples of other lipid matrices suitable for use with the methods of the invention include one or more of glycerides, fatty acids and alcohols, and fatty acid esters.

In one embodiment, a formulation may comprise an oily vehicle for the 25-hydroxyvitamin D compound. Any pharmaceutically-acceptable oil can be used. Examples include animal (e.g., fish), vegetable (e.g., soybean), and mineral oils. The oil preferably will readily dissolve the 25-hydroxyvitamin D compound used. Oily vehicles can include non-digestible oils, such as mineral oils, particularly liquid paraffins, and squalene. The ratio between the wax matrix and the oily vehicle can be optimized in order to achieve the desired rate of release of the 25-hydroxyvitamin D compound. Thus, if a heavier oil component is used, relatively less of the wax matrix can be used, and if a lighter oil component is used, then relatively more wax matrix can be used. In one embodiment, the particular choice of oily vehicle provides a controlled release so that absorption of 25-hydroxyvitamin D is delayed until the formulation reaches the ileum and/or colon.

Another suitable controlled-release oral drug delivery system is the EUDRAGIT RL/RS system in which the active 25-hydroxyvitamin D ingredient is formed into granules having a dimension of 25/30 mesh. The granules are then uniformly coated with a thin polymeric lacquer, which is water-insoluble but slowly water-permeable. The coated granules can be mixed with optional additives including one or more of antioxidants, stabilizers, binders, lubricants, processing aids and the like. The mixture may be compacted into a tablet which, prior to use, is hard and dry and can be further coated, or it may be poured into a capsule. After the tablet or capsule is swallowed and comes into contact with the aqueous intestinal fluids, the thin lacquer begins to swell and slowly allows permeation by intestinal fluids. As the intestinal fluid slowly permeates the lacquer coating, the contained 25-hydroxyvitamin D is slowly released. By the time the tablet or capsule has passed through the small intestine, about four to eight hours or more later, the 25-hydroxyvitamin D will have been slowly, but completely, released. Accordingly, the ingested tablet will release a stream of 25-hydroxyvitamin D, as well as any other active ingredient.

The EUDRAGIT system is comprised of high permeability lacquers (RL) and low permeability lacquers (RS). RS is a water-insoluble film former based on neutral swellable methacrylic acids esters with a small proportion of trimethylammonioethyl methacrylate chlorides; the molar ratio of the quaternary ammonium groups to the neutral ester group is about 1:40. RL is also a water insoluble swellable film former based on neutral methacrylic acid esters with a small portion of trimethylammonioethyl methacrylate chloride, the molar ratio of quaternary ammonium groups to neutral ester groups is about 1:20. The permeability of the coating and thus the time course of drug release can be titrated by varying the proportion of RS to RL coating material. For further details of the Eudragit RL/RS system, reference is made to technical publications available from Rohm Tech, Inc. 195 Canal Street, Maiden, Mass., 02146 and K. Lehmann, D. Dreher "Coating of tablets and small particles with acrylic resins by fluid bed technology," *Int. J. Pharm. Tech. & Prod. Mfr.* 2(r), 31-43 (1981), incorporated herein by reference.

Other examples of insoluble polymers include polyvinyl esters, polyvinyl acetals, polyacrylic acid esters, butadiene styrene copolymers and the like.

In one embodiment, once the coated granules are either formed into a tablet or put into a capsule, the tablet or capsule is coated with an enteric-coating material which dissolves at a pH of 7.0 to 8.0. One such pH-dependent enteric-coating material is EUDRAGIT L/S which dissolves in intestinal fluid, but not in the gastric juices. Other enteric-coating materials may be used such as cellulose acetate phthalate (CAP), which is resistant to dissolution by gastric juices, but readily disintegrates due to the hydrolytic effect of the intestinal esterases.

In one embodiment, the particular choice of enteric-coating material and controlled release coating material provides a controlled and substantially constant release over a period of 4 to 8 hours or more so that substantial release is delayed until the formulation reaches the ileum. Optionally, a controlled release composition in accordance with the present disclosure, when administered once a day, can suitably provide substantially constant intralumenal, intracellular and blood 25-hydroxyvitamin D levels compared to an equal dose of an immediate release composition of 25-hydroxyvitamin D administered once a day.

The dosage forms may also contain adjuvants, such as preserving or stabilizing adjuvants. For example, a preferred formulation includes 25-hydroxyvitamin D (e.g., about 30 mcg, about 60 mcg, or about 90 mcg 25-hydroxyvitamin $D_3$), about 2 wt % anhydrous ethanol, about 10 wt % lauroyl polyoxylglycerides, about 20 wt % hard paraffin, about 23 wt % glycerol monostearate, about 35 wt % liquid paraffin or mineral oil, about 10 wt % hydroxypropyl methylcellulose, and optionally a small amount of preservative (e.g., butylated hydroxytoluene). Formulations according to the invention may also contain other therapeutically valuable substances or may contain more than one of the compounds specified herein and in the claims in admixture.

As an alternative to oral 25-hydroxyvitamin D, intravenous administration of 25-hydroxyvitamin D is also contemplated. In one embodiment, the 25-hydroxyvitamin D is administered as a sterile intravenous bolus, optionally a bolus injection of a composition that results in a sustained release profile. In another embodiment, the 25-hydroxyvitamin D is administered via gradual injection/infusion, e.g., over a period of 1 to 5 hours, to effect controlled or substantially constant release of the 25-hydroxyvitamin D directly to DBP in the blood of the patient. For example, the composition may be injected or infused over a course of at least about 1 hour, at least about 2 hours, at least about 3 hours, at least about 4 hours, at least about 5 hours, or at least about 6 hours. In one embodiment, the composition intended for intravenous administration in accordance with the present invention is designed to contain a concentration of the 25-hydroxyvitamin D compound(s) of 1 to 100 mcg per unit dose. Sterile, isotonic formulations of 25-hydroxyvitamin D may be prepared by dissolving 25-hydroxyvitamin D in absolute ethanol, propylene glycol or another suitable solvent, and combining the resulting solution with one or more surfactants, salts and preservatives in appropriate volumes of water for injection. Such formulations can be administered slowly from syringes, for example, via heparin locks, or by addition to larger volumes of sterile solutions (e.g., saline solution) being steadily infused over time. In one embodiment, the composition can be co-injected or co-infused with an anticancer agent.

In another aspect, administration of an effective amount of a composition of the present disclosure can be effective to safely achieve supraphysiologic levels of 25-hydroxyvitamin D and/or 1,25-dihydroxyvitamin D i.e., without causing hypercalcemia and/or hyperphosphatemia.

Advantageously, adjunctive therapy comprising 25-hydroxyvitamin D and an agent that increases the risk of hypocalcemia and/or an anticancer agent, optionally together with other therapeutic agents, can be orally or intravenously administered in accordance with the above described embodiments in dosage amounts of from 1 to 1000 mcg 25-hydroxyvitamin D per day, with the preferred dosage amounts of from 5 mcg to 50 mcg, from 30 mcg to 90 mcg, from 100 mcg to 500 mcg, from 600 mcg to 900 mcg, from 200 mcg to 700 mcg, or from 500 mcg to 1000 mcg 25-hydroxyvitamin D per day. If the 25-hydroxyvitamin D and an agent that increases the risk of hypocalcemia and/or an anticancer agent are co-administered in combination with other therapeutic agents, the proportions of each of the compounds in the combination being administered will be dependent on the particular disease state being addressed. For example, one may choose to orally administer 25-hydroxyvitamin D with one or more calcium salts (intended as a calcium supplement or dietary phosphate binder), calcimimetics, nicotinic acid, iron, phosphate binders, cholecalciferol, ergocalciferol, active Vitamin D sterols, or glycemic and hypertension control agents. In addition, one may choose to intravenously administer 25-hydroxyvitamin D with cholecalciferol, ergocalciferol, active Vitamin D sterols, or glycemic and hypertension control agents. In practice, higher doses of the compounds of the present disclosure are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

The present invention is further explained by the following examples which should not be construed by way of limiting the scope of the present invention.

EXAMPLE 1

One Embodiment of a Modified Release Formulation for Oral Administration

Purified yellow beeswax and fractionated coconut oil are combined in a ratio of 1:1 and heated with continuous mixing to 75 degrees Celsius until a uniform mixture is obtained. The wax mixture is continuously homogenized while cooled to approximately 45 degrees Celsius. The active compounds, 25-hydroxyvitamin $D_2$ and 25-hydroxyvitamin $D_3$, in a ratio of 1:1, are dissolved in absolute ethanol and the ethanolic solution is added, with continuous homogenization, to the molten wax mixture. The amount of ethanol added is in the range of 1 to 2 v/v %. Mixing is continued until the mixture is uniform. The uniform mixture is loaded into soft gelatin capsules. The capsules are immediately rinsed to remove any processing lubricant(s) and briefly immersed in an aqueous solution of acetaldehyde in order to crosslink the gelatin shell. The concentration of the acetaldehyde solution and the immersion time is selected to achieve crosslinking to the desired degree, as determined by near-infrared spectrophotometry. The finished capsules are washed, dried and packaged.

EXAMPLE 2

One Embodiment of a Formulation for Intravenous Administration

TWEEN Polysorbate 20 is warmed to approximately 50 to 60 degrees Fahrenheit, and 25-hydroxyvitamin $D_3$, dissolved in a minimal volume of absolute ethanol, is added with continuous stirring. The resulting uniform solution of 25-hydroxyvitamin $D_3$, absolute ethanol and TWEEN Polysorbate 20 is transferred to a suitable volume of water for injection, which has been thoroughly sparged with nitrogen to remove all dissolved oxygen. Sodium chloride, sodium ascorbate, sodium phosphate (dibasic and monobasic), and disodium edetate are added, followed by sufficient stirring under a protective nitrogen atmosphere, to produce an isotonic homogeneous mixture containing, per 2 mL unit volume: 20 mcg of 25-hydroxyvitamin $D_3$; less than 0.01% absolute ethanol; 0.40% (w/v) TWEEN Polysorbate 20; 0.15% (w/v) sodium chloride; 1.00% (w/v) sodium ascorbate; 0.75% (w/v) sodium phosphate dibasic anhydrous; 0.18% (w/v) sodium phosphate monobasic monohydrate; and, 0.11% (w/v) disodium edetate. The mixture is sterilized by filtration and filled, with suitable protection from oxygen contamination, into amber glass ampules having an oxygen headspace of less than 1%.

EXAMPLE 3

Pharmacokinetics Testing in Dogs

Twenty male beagle dogs are divided randomly into two comparable groups and receive no supplemental Vitamin D for the next 30 days. At the end of this time, each dog in Group #1 receives a single softgel capsule containing 25 mcg of 25-hydroxyvitamin $D_2$ prepared in a controlled release formulation similar to the one disclosed in Example 1. Each dog in the other group (Group #2) receives a single immediate-release softgel capsule containing 25 mcg of 25-hydroxyvitamin $D_2$ dissolved in medium chain triglyceride oil. All dogs have received no food for at least 8 hours prior to dosing. Blood is drawn from each dog at 0, 0.5, 1, 1.5, 2, 3, 4, 6, 9, 15, 24, 36, and 72 hours after dose administration. The collected blood is analyzed for the contained levels of 25-hydroxyvitamin D, and the data are analyzed by treatment group. Dogs in Group #1 show a slower rise and a lower maximum (C) in mean blood levels of 25-hydroxyvitamin D than dogs in Group #2. However, dogs in Group #1 show a more prolonged elevation of mean blood levels of 25-hydroxyvitamin $D_2$ relative to dogs in Group #2, despite the fact that the $C_{max}$ recorded in Group #1 is lower. The mean area under the curve (AUC), corrected for predose background levels (recorded at t=0), is substantially greater for Group #1 for 25-hydroxyvitamin D. These procedures demonstrate that administration of 25-hydroxyvitamin $D_2$ in the formulation described in this invention to dogs results in blood levels of 25-hydroxyvitamin D which rise much more gradually and remain more stable than after dosing with the same amount of 25-hydroxyvitamin $D_2$ formulated for immediate release (in medium chain triglyceride oil). The greater AUC calculated for blood levels of 25-hydroxyvitamin D in Group #1 demonstrates that the bioavailability of 25-hydroxyvitamin $D_2$ formulated as described herein is markedly improved.

EXAMPLE 4

Pharmacokinetics Testing in Healthy Normal Volunteers

Sixteen healthy non-obese adults, aged 18 to 24 years, participate in an 11-week pharmacokinetic study in which they receive successively, and in a double-blinded fashion, two formulations of 25-hydroxyvitamin $D_2$. One of the formulations (Formulation #1) is a softgel capsule containing 100 mcg of 25-hydroxyvitamin $D_2$ prepared in a controlled release formulation similar to the one disclosed in Example 1. The other formulation (Formulation #2) is an immediate-release softgel capsule of identical appearance containing 100 mcg of 25-hydroxyvitamin $D_2$ dissolved in medium chain triglyceride oil. For 60 days prior to study start and continuing through study termination, the subjects abstain from taking other Vitamin D supplements. On Days 1, 3 and 5 of the study, all subjects provide fasting morning blood samples to establish pre-treatment baseline values. On the morning of Day 8, the subjects provide an additional fasting blood sample (t=0), and are randomly assigned to one of two treatment groups. Both groups are dosed with a single test capsule prior to eating breakfast: One group receives a capsule of Formulation #1 and the other group receives a capsule of Formulation #2. Blood is drawn from each subject at 0.5, 1, 1.5, 2, 3, 4, 6, 8, 10, 12, 15, 24, 36, 48, 72 and 108 hours after dose administration. On the morning of Day 70, the subjects provide additional fasting morning blood samples (t=0) and are dosed with a single capsule of the other test formulation prior to eating breakfast. Blood is again drawn from each subject at 0.5, 1, 1.5, 2, 3, 4, 6, 8, 10, 12, 15, 24, 36, 48, 72 and 108 hours after dose administration. All collected blood is analyzed for the contained levels of 25-hydroxyvitamin D, and the data are analyzed by treatment formulation after correction for baseline content. Formulation #1 is found to produce a slower rise and a lower $C_{max}$ in mean blood levels of 25-hydroxyvitamin D than Formulation #2. However, Formulation #1 also produces a more prolonged elevation of mean blood levels of 25-hydroxyvitamin $D_2$ relative to Formulation #2, despite the fact that the recorded $C_{max}$ is lower. The mean AUC for 25-hydroxyvitamin $D_2$ is substantially greater after administration of Formulation #1. These procedures demonstrate that administration of 25-hydroxyvitamin $D_2$ in the formulation described in this invention to healthy human adults results in blood levels of 25-hydroxyvitamin $D_2$ which rise much more gradually and remain more stable than after dosing with the same amount of 25-hydroxyvitamin $D_2$ formulated for immediate release (in medium chain triglyceride oil). The greater AUC calculated for blood levels of 25-hydroxyvitamin $D_2$ after dosing with Formulation #1 demonstrates that the bioavailability of 25-hydroxyvitamin $D_2$ formulated as described herein is better.

EXAMPLE 5

Efficacy Study in Healthy Adult Male Volunteers With Vitamin D Insufficiency

The effectiveness of three different formulations of Vitamin D in restoring serum total 25-hydroxyvitamin D to optimal levels (>30 ng/mL) is examined in a 23-day study of healthy non-obese men diagnosed with Vitamin D insufficiency. One of the formulations (Formulation #1) is a sustained release softgel capsule containing 30 mcg of 25-hydroxyvitamin $D_3$ prepared as illustrated in this disclosure. The second formulation (Formulation #2) is an immediate-release softgel capsule of identical appearance containing 50,000 IU of ergocalciferol dissolved in medium chain triglyceride oil. The third formulation (Formulation #3) is an immediate-release softgel capsule, also of identical appearance, containing 50,000 IU of cholecalciferol dissolved in medium chain triglyceride oil. A total of 100 healthy Caucasian and African-American men participate in this study, all of whom are aged 30 to 45 years and have serum 25-hydroxyvitamin D levels between 15 and 29 ng/mL (inclusive). All subjects abstain from taking other Vitamin D supplements for 60 days before study start and continuing through study termination, and from significant sun exposure. On Day 1 and 2 of the study, all subjects provide fasting morning blood samples to establish pre-treatment baseline values of serum total 25-hydroxyvitamin D. On the morning of Day 3, the subjects provide an additional fasting blood sample (t=0), are randomly assigned to one of four treatment groups, and are dosed with a single test capsule prior to eating breakfast: The subjects in Group #1 each receive a single capsule of Formulation #1, and the subjects in Groups #2 and #3 each receive a single capsule of Formulation #2 or Formulation #3, respectively. Subjects in Group #4 receive a matching placebo capsule. Subjects in Group #1 each receive an additional capsule of Formulation #1 on the mornings of Days 4 through 22 before breakfast, but subjects in Groups #2, #3 and #4 receive no additional capsules. A fasting morning blood sample is drawn from each subject, irrespective of treatment group, on Days 4, 5, 6, 10, 17 and 23 (or 1, 2, 3, 7, 14 and 20 days after the start of dosing). All collected blood is analyzed for the contained levels of 25-hydroxyvitamin D, and the data are analyzed by treatment group after correction for baseline values. Subjects in all four treatment groups exhibit mean baseline serum 25-hydroxyvitamin D levels of approximately 16 to 18 ng/mL, based on analysis of fasting blood samples drawn on Days 1 through 3. Subjects in Group #4 (control group) show no significant changes in mean serum total 25-hydroxyvitamin D over the course of the study. Subjects in Group #1 show a steadily increasing mean serum total 25-hydroxyvitamin D reaching at least 30 ng/mL by Day 23. In marked contrast, subjects in Group #2 exhibit marked increases in mean serum 25-hydroxyvitamin D for the first few days post-dosing, reaching a maximum of just above 25 ng/mL, and then rapidly declining thereafter. By study end, serum total 25-hydroxyvitamin D is significantly lower than baseline in Group #2. Subjects in Group #3 exhibit continuing increases in mean serum total 25-hydroxyvitamin D through the first 2 weeks after dosing with gradual, but progressive, decreases occurring thereafter. By study end, mean serum total 25-hydroxyvitamin D is below 30 ng/mL. The data from this study demonstrate that administration of 600 mcg of 25-hydroxyvitamin $D_3$, formulated as described herein and administered at a dose of 30 mcg per day for 20 days, is substantially more effective in restoring low serum levels of 25-hydroxyvitamin D to optimal levels than immediate-release formulations of 50,000 IU of either ergocalciferol or cholecalciferol administered in single doses, as currently recommended by the NKF and other leading experts on oral Vitamin D replacement therapy.

EXAMPLE 6

Efficacy Study in Osteoporosis Patients Treated with an Antiresorptive Agent

The effectiveness of oral modified release 25-hydroxyvitamin $D_3$ in restoring serum total 25-hydroxyvitamin D to optimal levels (>30 ng/mL), and thereby optimizing the effectiveness of an antiresorptive agent at increasing bone mineral density, is examined in a 24-month study of adult male and female patients with osteoporosis. In a randomized, double-blind controlled study, patients are treated with denosumab (60 mg at the start of treatment and again every six months). All denosumab-treated patients are randomized to receive daily oral treatment with one softgel capsule containing either 30 mcg of 25-hydroxyvitamin $D_3$ in a modified release formulation or 400 IU of Vitamin $D_3$ (cholecalciferol) in an immediate release formulation. A total of 500 subjects participate in this study, 250 male and 250 female, all of whom are aged 60 to 85 years (inclusive), have bone mineral density T-scores between −2.0 and −4.0, and have serum total 25-hydroxyvitamin D levels less than 30 ng/mL at the time of enrollment. All subjects receive calcium supplements (500 mg/day) and abstain from taking other Vitamin D supplements for 60 days before study start and continuing through study termination, and from significant sun exposure. All subjects begin daily dosing with softgel capsules at the start of denosumab treatment. Serum total 25-hydroxyvitamin D, PTH, calcium, phosphorus, N- and C-telopeptides, and P1NP, and urinary calcium, phosphorus and creatinine, are measured monthly. Bone mineral density at four sites (total hip, femoral neck, ⅓ radius and lumbar spine) is determined at quarterly intervals.

After 3 months, the daily softgel capsule dosage is maintained unchanged in patients whose serum total 25-hydroxyvitamin D is between 50 and 90 ng/mL, and increased by one capsule in patients whose serum total 25-hydroxyvitamin D is below 50 ng/mL. The dosage is immediately lowered by one capsule per day in patients whose serum total 25-hydroxyvitamin D rises above 100 ng/mL or whose serum calcium is confirmed above 10.3 mg/dL. After 6 to 9 months, all subjects exhibit serum total 25-hydroxyvitamin D levels that remain essentially stable with continuing dosing and rise to approximately 50 to 100 ng/mL with 25-hydroxyvitamin $D_3$ treatment or to approximately 25 to 35 ng/mL with Vitamin $D_3$ treatment. In patients treated with 25-hydroxyvitamin $D_3$, the incidence of hypocalcemia and severity of secondary hyperparathyroidism is markedly reduced once stable dosing has been achieved. However, in patients treated with Vitamin $D_3$, hypocalcemia and secondary hyperparathyroidism occur more frequently. After 24 months of treatment, the patients treated with denosumab and 25-hydroxyvitamin $D_3$ are found to have higher and more consistent serum levels of 25-hydroxyvitamin $D_3$ and lower serum PTH levels than patients treated with denosumab and Vitamin $D_3$. Patients treated with denosumab and 25-hydroxyvitamin $D_3$ are also found to have larger increases in bone mineral density than patients treated with denosumab and Vitamin $D_3$. Data from this study demonstrate that the modified release formulation of 25-hydroxyvitamin $D_3$ is effective at increasing serum total 25-hydroxyvitamin D without causing unacceptable side effects related to calcium and PTH metabolism and at augmenting the increases in bone mineral density produced by denosumab.

EXAMPLE 7

Efficacy Study in Prostate Cancer Patients

The effectiveness of oral modified release 25-hydroxyvitamin $D_3$ in restoring serum total 25-hydroxyvitamin D to optimal levels (greater than 30 ng/mL), thereby mitigating iatrogenic hypocalcemia and secondary hyperparathyroidism, and optimizing the effectiveness of an antiresorptive agent at mitigating skeletal-related events in prostate cancer patients, is examined in a 24-month study of adult male patients with bone-metastasized castration-resistant prostate cancer. In a randomized, double-blind controlled study, patients are treated with denosumab (120 mg every four weeks). All denosumab-treated patients are randomized to receive daily oral treatment with one softgel capsule containing either 30 mcg of 25-hydroxyvitamin $D_3$ in a modified release formulation or 400 IU of Vitamin $D_3$ in an immediate release formulation. A total of 500 subjects participate in this study, all of whom are aged 18 years or older with histologically confirmed prostate cancer. Prior to study admission, patients had to have received treatment for prostate cancer (e.g., bilateral orchiectomy or androgen-deprivation therapy for at least 6 months), have total serum testosterone lower than 50 ng/dL, and have three consecutive increasing PSA tests separated by at least 2 weeks with the last two PSA measurements greater than or equal to 1.0 mcg/L.

All patients have serum total 25-hydroxyvitamin D levels less than 30 ng/mL at the time of enrollment. All patients receive a radioisotope bone scan during screening with subsequent imaging by CT, MRI, or plain radiograph if needed to confirm bone metastases. All subjects receive calcium supplements (500 mg/day) and abstain from taking other Vitamin D supplements for 60 days before study start and continuing through study termination, and from significant sun exposure.

All subjects begin daily dosing with softgel capsules at the start of denosumab treatment. Serum total 25-hydroxyvitamin D, PTH, calcium, phosphorus, N- and C-telopeptides, and P1NP, and urinary calcium, phosphorus and creatinine, are measured monthly. Radiographic bone scans are conducted every 6 months to detect skeletal metastases, with a second imaging modality (CT, MRI, or plain radiograph) used to confirm diagnosis of any metastases detected. Bone mineral density at four sites (total hip, femoral neck, ⅓ radius and lumbar spine) is determined at the start of the study and thereafter at yearly intervals. After 3 months, the daily dosage of 25-hydroxyvitamin $D_3$ capsules is maintained unchanged in patients whose serum total 25-hydroxyvitamin D is between 50 and 90 ng/mL, and increased by one 30 mcg capsule in patients whose serum total 25-hydroxyvitamin D is below 50 ng/mL. The dosage is immediately lowered by one 30 mcg capsule per day in patients whose serum total 25-hydroxyvitamin D rises above 100 ng/mL or whose serum calcium is confirmed above 10.3 mg/dL.

After 6 months to 9 months, all subjects exhibit serum total 25-hydroxyvitamin D levels essentially stable in a range of 50 ng/mL to 90 ng/mL with 25-hydroxyvitamin $D_3$ treatment or between approximately 25 ng/mL to 35 ng/mL with Vitamin $D_3$ treatment. In patients treated with 25-hydroxyvitamin $D_3$, the incidence of hypocalcemia and severity of SHPT and hypercalcemia is markedly reduced once stable dosing has been achieved. In contrast, patients treated with Vitamin $D_3$ exhibit hypercalcemia and SHPT more frequently. After 24 months of treatment, the patients treated with denosumab and 25-hydroxyvitamin $D_3$ are found to have higher and more consistent serum levels of 25-hydroxyvitamin $D_3$ and lower serum PTH levels than patients treated with denosumab and vitamin $D_3$. Patients treated with denosumab and 25-hydroxyvitamin $D_3$ are found to have a significantly lower incidence of hypocalcemia, reduced plasma PTH levels and larger increases in bone mineral density and to have a significantly delayed time to first post-treatment SRE, compared to patients treated with denosumab and Vitamin $D_3$. Data from this study demonstrate that the modified release formulation of 25-hydroxyvitamin $D_3$ is effective at increasing serum 25-hydroxyvitamin D without causing unacceptable side effects related to calcium and PTH metabolism, and at mitigating hypocalcemia and augmenting the increases in bone mineral density and delayed time to first bone metastasis produced by denosumab.

EXAMPLE 8

Efficacy Study in Breast Cancer Patients

The effectiveness of oral modified-release 25-hydroxyvitamin $D_3$ in restoring serum total 25-hydroxyvitamin D to optimal levels (greater than 30 ng/mL), thereby mitigating hypocalcemia and SHPT and optimizing the effectiveness of denosumab at mitigating SRE in breast cancer patients, is examined in a 24-month study of adult female patients with breast cancer. In a randomized, double-blind controlled study, patients are treated with denosumab (120 mg every four weeks). All denosumab-treated patients are randomized to receive daily oral treatment with one softgel capsule containing either 30 mcg of 25-hydroxyvitamin $D_3$ in a modified release formulation or 400 IU of cholecalciferol in an immediate release formulation. All subjects participating in this study are aged 18 years or older with histologically or cytologically confirmed breast adenocarcinoma and current or prior radiographic (x-ray, CT or MRI) evidence of at least one bone metastasis. All subjects receive calcium supplements (500 mg/day) and abstain from taking other Vitamin D supplements for 60 days before study start and continuing through study termination, and from significant sun exposure. All subjects begin daily dosing with softgel capsules at the start of denosumab treatment. Serum total 25-hydroxyvitamin D, PTH, calcium, phosphorus, N- and C-telopeptides, and P1NP, and urinary calcium, phosphorus and creatinine, are measured monthly. Radiographic bone scans are conducted every 6 months to monitor skeletal metastases, with a second imaging modality (CT, MRI, or plain radiograph) used to confirm any metastases detected. Bone mineral density at four sites (total hip, femoral neck, ⅓ radius and lumbar spine) is determined at the start of the study and thereafter at yearly intervals. After 3 months, the daily softgel capsule dosage is maintained unchanged in patients whose serum total 25-hydroxyvitamin D is between 50 and 90 ng/mL and increased by one mcg capsule in patients whose serum total 25-hydroxyvitamin D is below 50 ng/mL. The dosage is immediately lowered by one capsule per day in patients whose serum total 25-hydroxyvitamin D rises above 100 ng/mL or whose serum calcium is confirmed above 10.3 mg/dL. After 6 to 9 months, the subjects' serum total 25-hydroxyvitamin D levels remain essentially stable with continued dosing, and rise to a level between about 50 ng/mL and about 90 ng/mL with 25-hydroxyvitamin $D_3$ treatment or to approximately 25 to 35 ng/mL with cholecalciferol treatment.

In patients treated with 25-hydroxyvitamin $D_3$, the incidence of hypocalcemia and severity of secondary hyperparathyroidism are markedly reduced once stable dosing has been achieved. However, in patients treated with vitamin $D_3$, hypocalcemia and secondary hyperparathyroidism occur more frequently. After 24 months of treatment, the patients treated with denosumab and 25-hydroxyvitamin $D_3$ are found to have higher and more consistent serum levels of 25-hydroxyvitamin $D_3$ and lower serum PTH levels than are patients treated with denosumab and vitamin $D_3$. Patients treated with denosumab and 25-hydroxyvitamin $D_3$ are found to have a significantly lower incidence of hypocalcemia and larger increases in bone mineral density and to have a significantly delayed time to additional bone metastasis, compared to patients treated with denosumab and Vitamin $D_3$. Data from this study demonstrate that the modified release formulation of 25-hydroxyvitamin $D_3$ is effective at increasing serum total 25-hydroxyvitamin D without causing unacceptable side effects related to calcium and PTH metabolism, and at mitigating hypocalcemia and augmenting the increases in bone mineral density and delayed time to bone metastasis produced by denosumab.

EXAMPLE 9

Safety Study in Patients with Metastatic Bone Disease Receiving Treatment with an Antiresorptive Agent The safety and tolerability of oral modified release 25-hydroxyvitamin $D_3$ is examined in an open label, repeat-dose study of adult patients diagnosed with metastases in bone originating from breast or prostate cancer who are receiving ongoing treatment with denosumab or zoledronic acid for at least 3 months. At the start of the study, all patients have plasma PTH greater than 70 pg/mL as evidence of SHPT, serum calcium less than 9.8 mg/dL, spot urine Ca:Cr ratio≤0.25 (≤250 mg/g creatinine) and an estimated glomerular filtration rate greater than 15 mL/min/1.73 $m^2$. Twenty-four (24) patients diagnosed with bone metastases subsequent to breast or pancreatic carcinoma are treated for up to 52 weeks with one or more capsules containing 30 mcg of 25-hydroxyvitamin $D_3$ in a modified release formulation. Denosumab or zoledronic acid are administered according to the typical standard of care for each patient's condition. Patients whose typical standard of care requires calcium and/or vitamin D supplementation receive less than 1000 mg/day of elemental calcium and/or 2000 IU/day or less of vitamin D (ergocalciferol and/or cholecalciferol). Patients do not receive any other vitamin D analogs (e.g., calcitriol, paricalcitol, doxercalciferol, etc.).

The 52-week study consists of a 40 week dose escalation phase followed by a 12-week maintenance phase. At the end of the maintenance phase, there is a two-week follow up phase. At the start of the study, all patients receive an initial daily dose of 30 mcg 25-hydroxyvitamin $D_3$, which is increased at four-week intervals over the course of the dose escalation phase up to a maximum daily dose of 300 mcg. The daily dose achieved by the end of the dose escalation study is the daily dose administered during the maintenance phase. Patients exhibiting a serum calcium level ≤10.3 mg/dL of the course of the study thus receive a daily dose of: 30 mcg 25-hydroxyvitamin $D_3$ at the start of the study; 60 mcg 25-hydroxyvitamin $D_3$ after 4 weeks; 90 mcg 25-hydroxyvitamin $D_3$ at 8 weeks; 120 mcg 25-hydroxyvitamin $D_3$ at 12 weeks; 150 mcg 25-hydroxyvitamin $D_3$ at 16 weeks; 180 mcg 25-hydroxyvitamin $D_3$ at 20 weeks; 210 mcg 25-hydroxyvitamin $D_3$ at 24 weeks; 240 mcg 25-hydroxyvitamin $D_3$ at 28 weeks; 270 mcg 25-hydroxyvitamin $D_3$ at 32 weeks; and 300 mcg 25-hydroxyvitamin $D_3$ at 36 weeks and through the maintenance phase. Patients exhibiting a serum calcium level exceeding 10.3 mg/dL for two consecutive visits will suspend dosing until serum calcium returns to ≤10.0 mg/dL, and then resume treatment at a reduced daily dose and enter a 12-week maintenance phase, followed by a 2-week follow-up period.

Blood samples are collected at 2-week intervals for monitoring serum levels of calcium and phosphorus. Samples are collected at 4-week intervals for monitoring plasma levels of PTH and PTHrP and serum total 25-hydroxyvitamin D, 24,25-dihydroxyvitamin $D_3$, calcitriol, and free and total calcifediol. Serum vitamin D metabolites and markers of bone metabolism, immune function, and tumor burden are measured at the beginning of the dose escalation phase and at the beginning and end of the maintenance phase. Urine samples are collected at 4-week intervals for monitoring the Ca/Cr ratio and urine chemistry. The genotype of vitamin D binding protein is determined for each subject at the beginning of the dose escalation phase.

Serum calcium gradually rises in the dose escalation phase while plasma PTH decreases. When plasma PTH is overly suppressed, serum calcium rises more quickly with continued dose escalation, increasing the risk of hypercalcemia. Patients exhibit significant increases in serum total 25-hydroxyvitamin D, 1,25-dihydroxyvitamin D, and 24,25-dihydroxyvitamin D, and decreases in plasma PTH. Patients receiving the starting dose level of 30 mcg of 25-hydroxyvitamin $D_3$ exhibit mean serum 25-hydroxyvitamin D levels of about 50 ng/mL. Patients receiving the dose level of 90 mcg of 25-hydroxyvitamin $D_3$ exhibit mean serum 25-hydroxyvitamin D levels of about 100 mg/mL. Patients receiving the highest dose level of 300 mcg of 25-hydroxyvitamin $D_3$ exhibit mean serum 25-hydroxyvitamin D levels of about 200 to about 300 ng/mL, for example, about 230 ng/mL. Data from this study demonstrate that a modified release formulation of 25-hydroxyvitamin $D_3$ is effective at increasing serum total 25-hydroxyvitamin D without causing unacceptable side effects related to calcium and PTH metabolism.

EXAMPLE 10

Efficacy Study in Patients with Metastatic Bone Disease Receiving Treatment With an Antiresorptive Agent The effectiveness of oral modified-release 25-hydroxyvitamin $D_3$ in raising serum 25-hydroxyvitamin D and 1,25-dihydroxyvitamin D and delaying cancer progression is examined in a 6-month randomized, double-blind placebo-controlled study of adult patients diagnosed with metastases in bone originating from breast or prostate cancer who are receiving ongoing treatment with denosumab or zoledronic acid for at least 3 months. Patients are treated with one or more capsules containing 30 mcg of 25-hydroxyvitamin $D_3$ in a modified release formulation or placebo. Denosumab or zoledronic acid are administered according to the typical standard of care for each patient's condition. Patients whose typical standard of care requires calcium and/or vitamin D supplementation receive less than 1000 mg/day of elemental calcium and/or 2000 IU/day or less of vitamin D (ergocalciferol and/or cholecalciferol). Samples are collected at monthly intervals for monitoring serum and urine levels of calcium, plasma levels of PTH and serum total 25-hydroxyvitamin D. Serum markers of tumor burden and bone metabolism, as well as cancer progression are assessed at 3-month intervals.

Patients treated with 25-hydroxyvitamin $D_3$ are found to have a greater increase in serum calcium and decrease in plasma PTH, leading to reduced risk of hypocalcemia compared to patients receiving the placebo. Patients treated with denosumab or zoledronic acid and 25-hydroxyvitamin D exhibit an increased delay in time to additional bone metastasis, compared to patients receiving denosumab or zoledronic acid in combination with a placebo. Data from this study demonstrate that the modified release formulation of 25-hydroxyvitamin $D_3$ is effective at increasing serum total 25-hydroxyvitamin D 1,25-dihydroxyvitamin D and delaying cancer progression, without causing unacceptable side effects related to calcium and PTH metabolism.

EXAMPLE 11

Efficacy Study in Patients with Metastatic Bone Disease Receiving Treatment with an Antiresorptive Agent for Prevention of SREs The effectiveness of oral modified release 25-hydroxyvitamin $D_3$ in delaying the time to the first post-treatment SRE is examined in 24-month randomized, double-blind placebo-controlled studies of adult males with castration-resistant prostate cancer metastatic to bone or adult females with estrogen-independent breast cancer metastatic to bone, who are receiving ongoing treatment with denosumab or zoledronic acid for at least 3 months. Patients are treated with one or more capsules containing 30 mcg of 25-hydroxyvitamin $D_3$ in a modified release formulation or placebo. Denosumab or zoledronic acid are administered according to the typical standard of care for each patient's condition. Patients are monitored for SREs, including by appropriate non-invasive imaging techniques, and serum markers of tumor burden and bone metabolism at 3-month intervals, and at monthly intervals for serum and urine calcium levels and plasma PTH. Cancer progression is monitored at quarterly intervals.

Patients treated with 25-hydroxyvitamin $D_3$ are found to have a greater increase in serum calcium and decrease in plasma PTH, leading to reduced risk of hypocalcemia compared to patients receiving the placebo. Patients treated with denosumab or zoledronic acid and 25-hydroxyvitamin D exhibit an increased delay in time to additional bone metastasis or SRE, compared to patients receiving denosumab or zoledronic acid in combination with a placebo. Data from this study demonstrate that 25-hydroxyvitamin $D_3$ is effective at significantly increasing the observed time to a post-treatment SRE and inhibiting tumor progression compared to placebo.

EXAMPLE 12

Efficacy Study of Combination Therapy Comprising 25-Hydroxyvitamin D and Cinacalcet in Patients with CKD The effectiveness of a composition comprising modified release 25-hydroxyvitamin $D_3$ and immediate release cinacalcet in preventing and treating hypocalcemia and treating secondary hyperparathyroidism is examined in a randomized, double-blind study of adult patients having CKD. Patients having CKD on dialysis (i.e., having CKD Stage 5), and not on dialysis (i.e., having CKD Stage 1, 2, 3, or 4) are treated daily with combination therapy comprising at least one capsule comprising both 30 mcg to 100 mcg 25-hydroxyvitamin D and 1 mg to 100 mg cinacalcet HCl and are compared to patients receiving placebo or 25-hydroxyvitamin D or cinacalcet alone. All patients have serum total 25-hydroxyvitamin D levels less than 30 ng/mL at the time of enrollment. Serum total 25-hydroxyvitamin D, parathyroid hormone, calcium, and phosphorus, are measured before treatment and then monthly.

After one to three months, all patients receiving the combination therapy exhibit serum total 25-hydroxyvitamin D levels essentially stable in a range of 50 ng/mL to 90 ng/mL and the incidence of hypocalcemia and severity of secondary hyperparathyroidism is markedly reduced. Patients having CKD on dialysis exhibit improvements in serum 25-hydroxyvitamin D, calcium, and parathyroid hormone levels following treatment with the combination therapy, despite having very severely reduced or no kidney function. Patients having CKD not on dialysis receiving the combination therapy have an incidence of hypocalcemia comparable to patients having CKD not on dialysis, in contrast to previous reports indicating that cinacalcet-treated patients with CKD not on dialysis had an increased risk for hypocalcemia compared to cinacalcet-treat patient with CKD on dialysis.

The foregoing description has outlined, in general, the featured aspects of the invention. In reference to such, there is to be a clear understanding that the present invention is not limited to the method or detail of manufacture, chemical composition, or application of use described herein. Any other variation of manufacture, chemical composition, use, or application should be considered apparent as an alternative embodiment of the present invention. Other advantages and a fuller appreciation of the specific adaptations, compositional variations and chemical and physical attributes of this invention will be gained upon examination of the detailed description.

Also, it is understood that the phraseology and terminology used herein are for the purpose of description and should not be regarded as limiting. Throughout the specification and the claims which follow, unless the context requires otherwise, the use of "including," "having," and "comprising" and variations thereof herein is meant to encompass the stated integers and steps and equivalents thereof as well as additional items and equivalents thereof.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The foregoing description is given for clearness of understanding only, and no unnecessary limitations should be understood therefrom, as modifications within the scope of the invention may be apparent to those having ordinary skill in the art. All patents, publications and references cited herein are hereby fully incorporated by reference. In case of conflict between the present disclosure and incorporated patents, publications and references, the present disclosure should control.

What is claimed is:

1. A method of managing iatrogenic hypocalcemia and secondary hyperparathyroidism in a patient receiving therapy with cinacalcet or a salt thereof, comprising administering to said patient a pharmaceutical formulation comprising (a) a 25-hydroxyvitamin D compound and (b) an agent that increases the risk of hypocalcemia, optionally cinacalcet or a salt thereof.

2. The method of claim 1, wherein the patient has impaired renal function, optionally associated with Chronic Kidney Disease Stage 1, 2, 3, 4, or 5.

3. The method of claim 1, wherein the patient is receiving dialysis.

4. The method of claim 1, wherein the patient is not on dialysis.

5. The method of claim 1, wherein the effective amount of 25-hydroxyvitamin D is effective to restore or maintain the patient's serum calcium level to at least about 8.0 mg/dL, optionally in a range of about 8.3 mg/dL to about 11.6 mg/dL.

6. The method of claim 1, wherein the effective amount of 25-hydroxyvitamin D is effective to safely increase the patient's serum level of 25-hydroxyvitamin D to at least 30 ng/mL, optionally in a range of about 30 ng/mL to about 100 ng/mL.

7. The method of claim 1, wherein the effective amount of 25-hydroxyvitamin D is effective to decrease the patient's serum parathyroid hormone level, optionally by 30% or more.

8. The method of claim 1, wherein the effective amount of 25-hydroxyvitamin D is administered in an oral modified release formulation, optionally a sustained release formulation.

9. The method of claim 1, wherein the 25-hydroxyvitamin D is co-administered in an oral formulation comprising cinacalcet or a salt thereof.

10. The method of claim 1, wherein the 25-hydroxyvitamin D comprises 25-hydroxyvitamin $D_3$, 25-hydroxyvitamin $D_2$, or a combination thereof.

11. The method of claim 10, wherein the 25-hydroxyvitamin D comprises 25-hydroxyvitamin $D_3$.

12. The method of claim 1, wherein the 25-hydroxyvitamin D is administered in a dosage of 1 mcg to 1000 mcg per day.

13. The method of claim 1, wherein the cinacalcet or salt thereof comprises cinacalcet HCl.

14. The method of claim 1, wherein the patient is receiving cinacalcet administered in a dosage of 1 mg to 400 mg per day.

15. A method of treating secondary hyperparathyroidism in Chronic Kidney Disease in a patient on dialysis comprising administering to said patient an effective amount of a 25-hydroxyvitamin D compound by modified release and an effective dose of cinacalcet or a salt thereof in an amount of less than 360 mg daily, wherein said effective amount of cinacalcet is a reduced dose compared to the effective dose of cinacalcet in the absence of said 25-hydroxyvitamin D administration.

16. The method of claim 15, comprising an initial dose of cinacalcet in a range of about 20 mg to about 25 mg once daily.

17. A method of treating hypercalcemia in a patient with parathyroid carcinoma, comprising administering to said patient an effective amount of a 25-hydroxyvitamin D compound by modified release and an effective dose of cinacalcet or a salt thereof in an amount of less than 360 mg daily, wherein said effective amount of cinacalcet or a salt thereof is a reduced dose compared to the effective dose of cinacalcet in the absence of said 25-hydroxyvitamin D administration.

18. A method of treating severe hypercalcemia in a patient with primary hyperparathyroidism who is unable to undergo parathyroidectomy, comprising administering to said patient an effective amount of a 25-hydroxyvitamin D compound by modified release and an effective dose of cinacalcet or a salt thereof in an amount of less than 360 mg daily, wherein said effective amount of cinacalcet or a salt thereof is a reduced dose compared to the effective dose of cinacalcet in the absence of said 25-hydroxyvitamin D administration.

19. The method of claim 17, comprising an initial dose of cinacalcet in a range of about 20 mg to about 25 mg once daily.

20. The method of claim 1, wherein the effective amount of 25-hydroxyvitamin D is in a range of about 100 mcg to about 300 mcg.

21. A method of treating a patient treated with an agent that increases the risk of hypocalcemia to (i) increase bone mineral density, (ii) decrease the blood level of a bone resorption marker, (iii) treat bone pain, (iv) increase the time to the first post-treatments skeletal-related event, said method comprising administering to the patient an effective amount of 25-hydroxyvitamin D, optionally, wherein 25-hydroxyvitamin D is administered in an amount effective to effectively and safely restore blood 25-hydroxyvitamin D levels to at least 30 ng/mL and to maintain blood 25-hydroxyvitamin D levels at such optimal levels.

22. A method of lowering elevated serum parathyroid hormone levels and/or stabilizing serum calcium levels in a patient having a bone metastasis and treated with an anti-resorptive agent comprising administering an effective amount of 25-hydroxyvitamin D.

* * * * *